United States Patent
Buhler et al.

(10) Patent No.: US 9,690,963 B2
(45) Date of Patent: Jun. 27, 2017

(54) HAND-HELD DUAL SPHERICAL ANTENNA SYSTEM

(71) Applicant: Covidien LP, Mansfield, MA (US)

(72) Inventors: John T. Buhler, Carlsbad, CA (US); William A. Blair, Carlsbad, CA (US); David A. Poirier, Escondido, CA (US); Curtis Crump, Vista, CA (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 15/052,125

(22) Filed: Feb. 24, 2016

(65) Prior Publication Data

US 2016/0259954 A1    Sep. 8, 2016

Related U.S. Application Data

(60) Provisional application No. 62/127,130, filed on Mar. 2, 2015.

(51) Int. Cl.
*G06K 7/00* (2006.01)
*G06K 19/02* (2006.01)
(Continued)

(52) U.S. Cl.
CPC .......... *G06K 7/10386* (2013.01); *A61B 90/98* (2016.02); *G06K 7/10316* (2013.01);
(Continued)

(58) Field of Classification Search
CPC .......... G06K 7/10386; G06K 7/10316; G06K 7/10356; H01Q 7/00; H01Q 21/02;
(Continued)

(56) References Cited

U.S. PATENT DOCUMENTS

| 3,422,816 A | 1/1969 | Robinson et al. |
| 3,587,583 A | 6/1971 | Greenberg |

(Continued)

FOREIGN PATENT DOCUMENTS

| AU | 716011 B2 | 2/2000 |
| CN | 101460096 A | 6/2009 |

(Continued)

OTHER PUBLICATIONS

Barnes et al., "Method, Apparatus and Article for Detection of Transponder Tagged Objects, for Example During Surgery," U.S. Appl. No. 61/056,787, filed May 28, 2008, 60 pages.

(Continued)

*Primary Examiner* — Laura Gudorf

(57) ABSTRACT

A hand-held antenna system allows medical personnel to ascertain the presence or absence of objects (e.g., medical supplies) tagged with transponders in an environment in which medical procedures are performed. In use, the hand-held antenna system may be positioned proximate a patient at a time after a medical procedure, such as after childbirth, so the system can scan the patient's body to determine the presence of objects tagged with transponders. The antenna system includes two sets of three antenna elements arranged mutually orthogonal to each other to transmit and receive signals in at least three coordinate directions. A controller is coupled to the antenna elements to transmit signals to the transponders and to receive response signals. The antenna system may operate in a static scan mode wherein the antenna system is held in a fixed position by a user and a dynamic scan mode wherein the antenna system is moved by a user.

18 Claims, 22 Drawing Sheets

(51) Int. Cl.
*G06K 7/10* (2006.01)
*H01Q 21/24* (2006.01)
*A61B 90/98* (2016.01)
*H01Q 7/00* (2006.01)
*H01Q 1/22* (2006.01)
*H01F 5/02* (2006.01)
*A61B 90/00* (2016.01)
*A61B 34/20* (2016.01)

(52) U.S. Cl.
CPC ............ *H01Q 1/2208* (2013.01); *H01Q 7/00* (2013.01); *H01Q 21/24* (2013.01); *A61B 2034/2051* (2016.02); *A61B 2090/0804* (2016.02); *H01F 2005/027* (2013.01)

(58) Field of Classification Search
CPC H01Q 21/00; A61B 90/98; A61B 2034/2051; A61B 2090/0804; H01F 2005/027
USPC ........................................................ 235/492
See application file for complete search history.

(56) References Cited

U.S. PATENT DOCUMENTS

| | | |
|---|---|---|
| 3,717,876 A | 2/1973 | Volkers et al. |
| 4,034,297 A | 7/1977 | Giorgi et al. |
| 4,114,601 A | 9/1978 | Abels |
| 4,193,405 A | 3/1980 | Abels |
| 4,355,317 A | 10/1982 | Muzio |
| 4,422,548 A | 12/1983 | Cheesman et al. |
| 4,658,818 A | 4/1987 | Miller, Jr. et al. |
| 4,681,111 A | 7/1987 | Silvian |
| 4,893,118 A | 1/1990 | Lewiner et al. |
| 4,992,675 A | 2/1991 | Conner, Jr. et al. |
| 5,031,642 A | 7/1991 | Nosek |
| 5,057,095 A | 10/1991 | Fabian |
| 5,105,829 A | 4/1992 | Fabian et al. |
| 5,107,862 A | 4/1992 | Fabian et al. |
| 5,188,126 A | 2/1993 | Fabian et al. |
| 5,190,059 A | 3/1993 | Fabian et al. |
| 5,231,273 A | 7/1993 | Caswell et al. |
| 5,235,326 A | 8/1993 | Beigel et al. |
| 5,258,742 A | 11/1993 | Soldevila Domingo et al. |
| 5,281,941 A * | 1/1994 | Bernstein ................ H01F 5/02 336/188 |
| 5,329,944 A | 7/1994 | Fabian et al. |
| 5,353,011 A | 10/1994 | Wheeler et al. |
| 5,390,360 A | 2/1995 | Scop et al. |
| 5,446,447 A | 8/1995 | Carney et al. |
| 5,450,622 A | 9/1995 | Vandegraaf |
| 5,482,036 A | 1/1996 | Diab et al. |
| 5,629,498 A | 5/1997 | Pollock et al. |
| 5,650,596 A | 7/1997 | Morris et al. |
| 5,664,582 A | 9/1997 | Szymaitis |
| 5,923,001 A | 7/1999 | Morris et al. |
| 5,928,151 A | 7/1999 | Hossack et al. |
| 6,026,818 A | 2/2000 | Blair et al. |
| 6,075,797 A | 6/2000 | Thomas |
| 6,172,608 B1 | 1/2001 | Cole |
| 6,201,469 B1 | 3/2001 | Balch et al. |
| 6,211,666 B1 | 4/2001 | Acker |
| 6,215,437 B1 | 4/2001 | Schürmann et al. |
| 6,223,137 B1 | 4/2001 | McCay et al. |
| 6,232,878 B1 | 5/2001 | Rubin |
| 6,270,460 B1 | 8/2001 | McCartan et al. |
| 6,317,027 B1 | 11/2001 | Watkins |
| 6,349,234 B2 | 2/2002 | Pauly et al. |
| 6,353,406 B1 | 3/2002 | Lanzl et al. |
| 6,354,493 B1 | 3/2002 | Mon |
| 6,359,562 B2 | 3/2002 | Rubin |
| 6,366,206 B1 | 4/2002 | Ishikawa et al. |
| 6,401,722 B1 | 6/2002 | Krag |
| 6,557,752 B1 | 5/2003 | Yacoob |
| 6,566,997 B1 | 5/2003 | Bradin |
| 6,588,661 B2 | 7/2003 | Degrauwe et al. |
| 6,632,216 B2 | 10/2003 | Houzego et al. |
| 6,633,226 B1 | 10/2003 | Nysen |
| 6,641,039 B2 | 11/2003 | Southard |
| 6,648,223 B2 | 11/2003 | Boukhny et al. |
| 6,650,240 B2 | 11/2003 | Lee et al. |
| 6,696,954 B2 | 2/2004 | Chung |
| 6,722,783 B2 | 4/2004 | Jackson, Sr. |
| 6,734,795 B2 | 5/2004 | Price |
| 6,744,378 B1 | 6/2004 | Tyburski |
| 6,753,783 B2 | 6/2004 | Friedman et al. |
| 6,774,800 B2 | 8/2004 | Friedman et al. |
| 6,777,623 B2 | 8/2004 | Ballard |
| 6,786,405 B2 | 9/2004 | Wiedenhoefer |
| 6,812,824 B1 | 11/2004 | Goldinger et al. |
| 6,812,842 B2 | 11/2004 | Dimmer |
| 6,822,570 B2 | 11/2004 | Dimmer et al. |
| 6,838,990 B2 | 1/2005 | Dimmer |
| 6,861,954 B2 | 3/2005 | Levin |
| 6,879,300 B2 | 4/2005 | Rochelle et al. |
| 6,903,656 B1 | 6/2005 | Lee |
| 6,909,366 B1 | 6/2005 | Marsh et al. |
| 6,977,504 B2 | 12/2005 | Wright et al. |
| 6,998,541 B2 | 2/2006 | Morris et al. |
| 7,001,366 B2 | 2/2006 | Ballard |
| 7,019,650 B2 | 3/2006 | Volpi et al. |
| 7,026,924 B2 | 4/2006 | Degrauwe et al. |
| 7,026,927 B2 | 4/2006 | Wright et al. |
| 7,071,791 B1 | 7/2006 | Wilson, III |
| 7,098,793 B2 | 8/2006 | Chung |
| 7,098,866 B2 | 8/2006 | Desjeux et al. |
| 7,142,815 B2 | 11/2006 | Desjeux et al. |
| 7,158,030 B2 | 1/2007 | Chung |
| 7,158,754 B2 | 1/2007 | Anderson |
| 7,160,258 B2 | 1/2007 | Imran et al. |
| 7,176,798 B2 | 2/2007 | Dimmer et al. |
| 7,227,469 B2 | 6/2007 | Varner et al. |
| 7,245,893 B1 | 7/2007 | Husted et al. |
| 7,256,695 B2 | 8/2007 | Hamel et al. |
| 7,256,696 B2 | 8/2007 | Levin |
| 7,268,684 B2 | 9/2007 | Tethrake et al. |
| 7,299,981 B2 | 11/2007 | Hickle et al. |
| D557,421 S | 12/2007 | Fleck et al. |
| 7,319,396 B2 | 1/2008 | Homanfar et al. |
| 7,319,397 B2 | 1/2008 | Chung et al. |
| 7,319,398 B2 | 1/2008 | Marino |
| 7,325,723 B2 | 2/2008 | Desjeux |
| 7,333,013 B2 | 2/2008 | Berger |
| 7,342,497 B2 | 3/2008 | Chung et al. |
| 7,362,228 B2 | 4/2008 | Nycz et al. |
| 7,382,255 B2 | 6/2008 | Chung |
| 7,397,364 B2 | 7/2008 | Govari |
| 7,408,168 B1 | 8/2008 | Aufrichtig et al. |
| 7,420,468 B2 | 9/2008 | Fabian et al. |
| 7,423,535 B2 | 9/2008 | Chung et al. |
| 7,446,646 B2 | 11/2008 | Huomo |
| 7,464,713 B2 | 12/2008 | Fabian et al. |
| 7,492,257 B2 | 2/2009 | Tethrake et al. |
| 7,492,261 B2 | 2/2009 | Cambre et al. |
| 7,508,308 B2 | 3/2009 | Chung |
| 7,513,425 B2 | 4/2009 | Chung |
| 7,541,933 B2 | 6/2009 | Volpi et al. |
| 7,557,710 B2 | 7/2009 | Sanchez et al. |
| 7,644,016 B2 | 1/2010 | Nycz et al. |
| 7,696,877 B2 | 4/2010 | Barnes et al. |
| 7,769,422 B2 | 8/2010 | DiSilvestro et al. |
| 7,795,491 B2 | 9/2010 | Stewart et al. |
| 7,855,656 B2 | 12/2010 | Maschke |
| 7,876,097 B2 | 1/2011 | Greim |
| 7,898,420 B2 | 3/2011 | Blair et al. |
| 8,105,296 B2 | 1/2012 | Morris et al. |
| 8,106,660 B1 * | 1/2012 | Merewether ........... G01V 3/104 324/326 |
| 8,111,162 B2 | 2/2012 | Barnes et al. |
| 8,181,860 B2 | 5/2012 | Fleck et al. |
| 8,193,938 B2 | 6/2012 | Halberthal et al. |
| 8,256,674 B2 | 9/2012 | Fleck et al. |
| 8,279,068 B2 | 10/2012 | Morris et al. |
| 8,319,612 B2 | 11/2012 | Borcherding |

(56) References Cited

U.S. PATENT DOCUMENTS

| | | |
|---|---|---|
| 8,323,189 B2 | 12/2012 | Tran et al. |
| 8,358,212 B2 | 1/2013 | Blair |
| 8,477,077 B1 | 7/2013 | Nero, Jr. et al. |
| 8,479,989 B2 | 7/2013 | Fleck et al. |
| 8,576,076 B2 | 11/2013 | Morris et al. |
| 8,710,957 B2 | 4/2014 | Blair et al. |
| 8,872,662 B2 | 10/2014 | Halberthal et al. |
| 8,937,575 B2 | 1/2015 | Ward et al. |
| 8,985,446 B2 | 3/2015 | Fleck et al. |
| 8,994,358 B2 | 3/2015 | McElhinny et al. |
| 9,041,479 B2 | 5/2015 | Nero, Jr. et al. |
| 9,168,104 B2 | 10/2015 | Dein |
| 9,414,973 B2 | 8/2016 | Fleck et al. |
| 2001/0030610 A1 | 10/2001 | Rochelle et al. |
| 2002/0011932 A1 | 1/2002 | Rodgers et al. |
| 2002/0032435 A1 | 3/2002 | Levin et al. |
| 2002/0070863 A1 | 6/2002 | Brooking |
| 2002/0143320 A1 | 10/2002 | Levin |
| 2002/0165587 A1 | 11/2002 | Zhang et al. |
| 2002/0188259 A1 | 12/2002 | Hickle et al. |
| 2003/0004411 A1 | 1/2003 | Govari et al. |
| 2003/0105394 A1 | 6/2003 | Fabian et al. |
| 2004/0129279 A1 | 7/2004 | Fabian et al. |
| 2004/0137844 A1 | 7/2004 | Desjeux et al. |
| 2004/0250819 A1 | 12/2004 | Blair et al. |
| 2005/0110640 A1 | 5/2005 | Chung et al. |
| 2005/0131397 A1 | 6/2005 | Levin |
| 2005/0202827 A1 | 9/2005 | DeMarco et al. |
| 2005/0212673 A1 | 9/2005 | Forster |
| 2005/0247794 A1 | 11/2005 | Jones et al. |
| 2005/0249036 A1 | 11/2005 | Davies et al. |
| 2005/0267550 A1 | 12/2005 | Hess et al. |
| 2006/0055537 A1 | 3/2006 | Jackson |
| 2006/0106368 A1 | 5/2006 | Miller et al. |
| 2006/0109086 A1 | 5/2006 | Amtmann |
| 2006/0163350 A1 | 7/2006 | Melton et al. |
| 2006/0187044 A1 | 8/2006 | Fabian et al. |
| 2006/0235488 A1 | 10/2006 | Nyez et al. |
| 2006/0241396 A1 | 10/2006 | Fabian et al. |
| 2006/0241399 A1 | 10/2006 | Fabian |
| 2007/0004994 A1 | 1/2007 | Sherman |
| 2007/0005141 A1 | 1/2007 | Sherman |
| 2007/0069866 A1 | 3/2007 | Schuessler et al. |
| 2007/0109099 A1 | 5/2007 | Raphaeli et al. |
| 2007/0152823 A1 | 7/2007 | Hirahara et al. |
| 2007/0213837 A1 | 9/2007 | Ferreri et al. |
| 2007/0238982 A1 | 10/2007 | Caylor, III |
| 2007/0239289 A1 | 10/2007 | Cambre et al. |
| 2007/0265690 A1 | 11/2007 | Lichtenstein et al. |
| 2007/0270660 A1 | 11/2007 | Caylor, III et al. |
| 2007/0285249 A1 | 12/2007 | Blair et al. |
| 2008/0007411 A1 | 1/2008 | Levin |
| 2008/0024281 A1 | 1/2008 | Shimura |
| 2008/0051746 A1 | 2/2008 | Shen-Gunther |
| 2008/0126122 A1 | 5/2008 | Warner et al. |
| 2008/0132860 A1 | 6/2008 | Smith et al. |
| 2008/0136721 A1* | 6/2008 | Parsche ............ H01Q 7/00 343/742 |
| 2008/0231452 A1 | 9/2008 | Levin |
| 2008/0243404 A1 | 10/2008 | Banhegyesi |
| 2008/0272913 A1 | 11/2008 | Barnes et al. |
| 2008/0281190 A1 | 11/2008 | Petcavich et al. |
| 2008/0284570 A1 | 11/2008 | Ryoo et al. |
| 2008/0296373 A1 | 12/2008 | Zmood et al. |
| 2009/0008449 A1 | 1/2009 | Qing et al. |
| 2009/0015408 A1* | 1/2009 | Asai ............ G06K 7/10386 340/572.1 |
| 2009/0051485 A1 | 2/2009 | Corry et al. |
| 2009/0121965 A1* | 5/2009 | Palmade ............ H01Q 1/2208 343/867 |
| 2009/0132008 A1 | 5/2009 | Snitting et al. |
| 2009/0267765 A1 | 10/2009 | Greene et al. |
| 2009/0322485 A1 | 12/2009 | Barnes et al. |
| 2010/0109848 A1 | 5/2010 | Blair et al. |
| 2011/0063078 A1 | 3/2011 | Souma |
| 2011/0181394 A1 | 7/2011 | Blair |
| 2013/0023225 A1 | 1/2013 | Weber |
| 2015/0054625 A1 | 2/2015 | Blair et al. |
| 2015/0164603 A1 | 6/2015 | Fleck et al. |
| 2015/0216610 A1 | 8/2015 | Augustine |
| 2015/0272688 A1 | 10/2015 | Blair et al. |
| 2016/0157957 A1 | 6/2016 | Blair |
| 2016/0206399 A1 | 7/2016 | Blair |
| 2016/0210548 A1 | 7/2016 | Blair |
| 2016/0259954 A1 | 9/2016 | Buhler et al. |

FOREIGN PATENT DOCUMENTS

| | | |
|---|---|---|
| JP | 2009-539478 A | 11/2009 |
| WO | 86/02539 A1 | 5/1986 |
| WO | 02/39917 A1 | 5/2002 |
| WO | 03/073934 A1 | 9/2003 |
| WO | 2004/078039 A1 | 9/2004 |
| WO | 2004/086997 A | 10/2004 |
| WO | 2007/024348 A2 | 3/2007 |
| WO | 2007/120736 A2 | 10/2007 |
| WO | 2007/146091 A2 | 12/2007 |
| WO | 2008/008449 A2 | 1/2008 |
| WO | 2008/024921 A2 | 2/2008 |
| WO | 2008/106552 A1 | 9/2008 |
| WO | 2008/133634 A1 | 11/2008 |
| WO | 2009/154987 A2 | 12/2009 |
| WO | 2014/176072 A1 | 10/2014 |

OTHER PUBLICATIONS

Barnes et al., "Method, Apparatus and Article for Detection of Transponder Tagged Objects, for Example During Surgery," U.S. Appl. No. 61/091,667, filed Aug. 25, 2008, 76 pages.

Blair et al., "Improved Apparatus and Method for Detecting Objects Using Tags and Wideband Detection Device," U.S. Appl. No. 60/811,376, filed Jun. 6, 2006, 16 pages.

Blair et al., "Method and Apparatus to Detect Transponder Tagged Objects, for Example During Medical Procedures," U.S. Appl. No. 61/242,704, filed Sep. 15, 2009, 127 pages.

Blair et al., "Method and Apparatus to Detect Transponder Tagged Objects, for Example During Surgery," U.S. Appl. No. 61/109,104, filed Oct. 28, 2008, 73 pages.

Blair et al., "Method, Apparatus and Article for Detection of Transponder Tagged Objects, for Example During Surgery," U.S. Appl. No. 60/892,208, filed Feb. 28, 2007, 50 pages.

Blair et al., "Tag and Detection Device," U.S. Appl. No. 60/458,222, filed Mar. 27, 2003, 23 pages.

Blair, "Detectable Surgical Objects and Methods of Making Same," U.S. Appl. No. 61/109,142, filed Oct. 28, 2008, 47 pages.

Blair, "Method and Apparatus to Account for Transponder Tagged Objects Used During Medical Procedures," U.S. Appl. No. 61/263,726, filed Nov. 23, 2009, 78 pages.

Blair, "Transponder Device to Mark Implements, Such As Surgical Implements, and Method of Manufacturing and Using Same," U.S. Appl. No. 61/086,727, filed Aug. 6, 2008, 30 pages.

Blair, "Transponder Device to Mark Implements, Such As Surgical Implements, and Method of Manufacturing and Using Same," U.S. Appl. No. 61/220,452, filed Jun. 25, 2009, 46 pages.

Blair, "Method and Apparatus to Detect Transponder Tagged Objects, for Example During Surgery," U.S. Appl. No. 61/222,443, file Jul. 1, 2009, 95 pages.

Clearcount Medical Solutions, "The SmartSponge System," Downloaded from http://clearcount.com on Oct. 20, 2009, 7 pages.

Haldor Advanced Technologies, "Haldor Advanced Technologies Releases a Breakthrough New Sponge Management Solution: Modular, Mobile, Wireless, and Tailored per Use-case and Requirements," Sep. 8, 2015, retrieved from http://ww1.prweb.om/prfiles/2015/09/06/12938762/ORLocate%205 Sponge%20Solution-September%202015.pdf, 2 pages.

Macario et al., "Initial Clinical Evaluation of a Handheld Device for Detecting Retained Surgical Gauze Sponges Using Radiofrequency Identification Technology," Arch Surg 141:659-662, Jul. 2006.

(56) References Cited

OTHER PUBLICATIONS

Barnes et al., "Design for a FET based 1 MHz, 10kV Pulse Generator," Pulsed Power Conference, Digest of Technical Papers, Tenth IEEE International, 2:1335-1340, 1995.
Black, "Method and Apparatus to Account for Transponder Tagged Objects During Clinical Procedures, Employing a Trocar," U.S. Appl. No. 62/360,869, filed Jul. 11, 2016, 99 pages.
Black, "Method and Apparatus to Account for Transponder Tagged Objects Used During Clinical Procedures, Employing a Trocar," U.S. Appl. No. 62/378,515, filed Aug. 23, 2016, 103 pages.
Extended European Search Report, dated Jul. 14, 2016, for corresponding European Application No. 16158315.8, 7 pages.
Hansen et al., "Method and Apparatus to Account for Transponder Tagged Objects Used During Clinical Procedures, Employing a Shielded Receptacle," U.S. Appl. No. 62/360,864, filed Jul. 11, 2016, 99 pages.
Hansen et al., "Method and Apparatus to Account for Transponder Tagged Objects Used During Clinical Procedures Employing a Shielded Receptacle With Antenna," U.S. Appl. No. 62/360,866, filed Jul. 11, 2016, 154 pages.
International Search Report, mailed Jan. 4, 2010, for PCT/US2009/045312, 3 pages.
International Search Report, mailed Mar. 24, 2015, for PCT/US2014/070547, 3 pages.
Poirier et al., "Method and Apparatus to Account for Transponder Tagged Objects Used During Clinical Procedures, for Example Including Count in and/or Count Out and Presence Detection," U.S. Appl. No. 62/360,868, filed Jul. 11, 2016, 113 pages.
Poirier et al., "Method and Apparatus to Account for Transponder Tagged Objects Used During Clinical Procedures, for Example Including Count in and/or Count Out and Presence Detection," U.S. Appl. No. 62/378,511, filed Aug. 23, 2016, 114 pages.
Reza et al., "RFID Transponder Collision Control Algorithm," *Wireless Pers. Commun.* 59:689-711, 2011.
Written Opinion, mailed Jan. 4, 2010, for PCT/US2009/045312, 3 pages.

\* cited by examiner

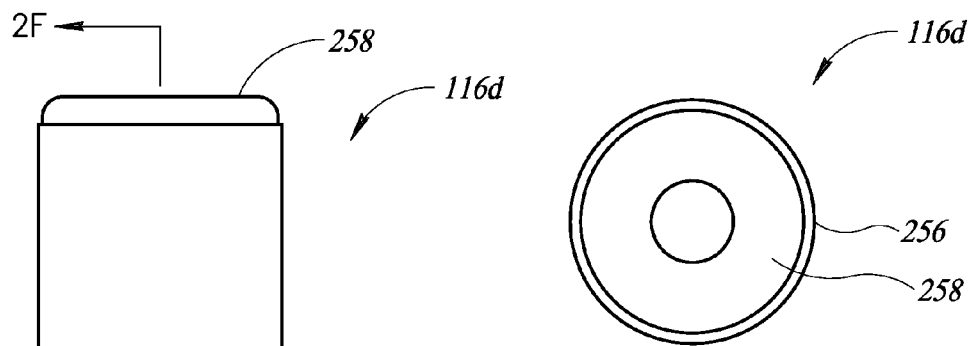
FIG. 2D
FIG. 2E
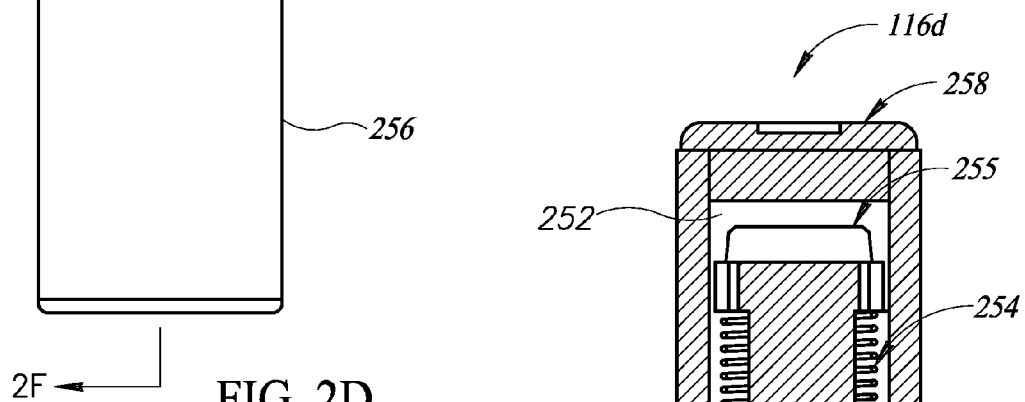
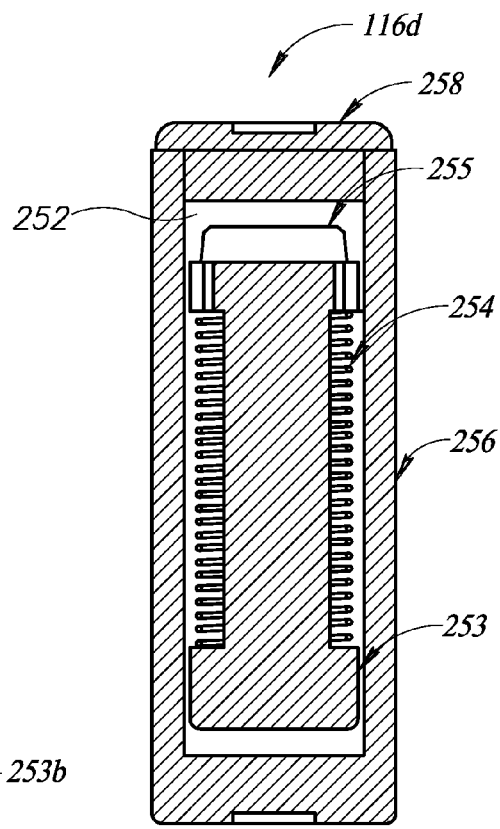
FIG. 2F
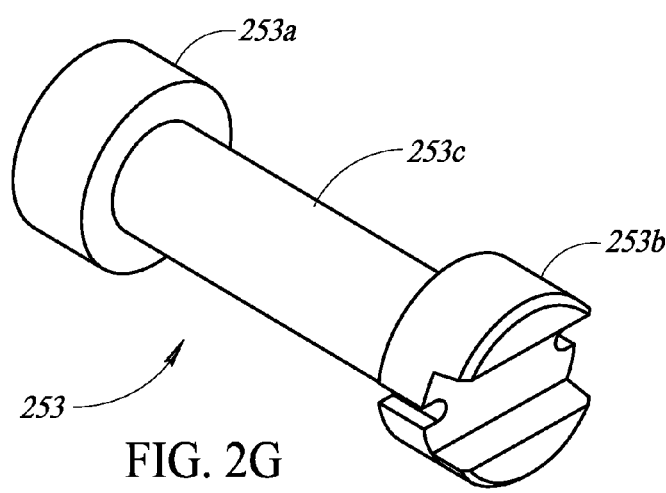
FIG. 2G

HAND-HELD DUAL SPHERICAL ANTENNA SYSTEM

CROSS-REFERENCE TO RELATED APPLICATIONS

This application claims the benefit of and priority to U.S. Provisional Patent Application No. 62/127,130 filed Mar. 2, 2015, the entire disclosure of which is incorporated by reference herein.

BACKGROUND

Field

This disclosure generally relates to the detection of the presence or absence of objects tagged with transponders, which may, for example, allow the detection of retained medical supplies during medical procedures.

Description of the Related Art

It is often useful or important to be able to determine the presence or absence of an object.

For example, it is important to determine whether objects associated with surgery are present in a patient's body before completion of the surgery. Such objects may take a variety of forms. For example, the objects may take the form of instruments, for instance scalpels, scissors, forceps, hemostats, and/or clamps. Also for example, the objects may take the form of related accessories and/or disposable objects, for instance surgical sponges, gauzes, and/or pads. Failure to locate an object before closing the patient may require additional surgery, and in some instances may have serious adverse medical consequences.

Some hospitals have instituted procedures which include checklists or requiring multiple counts to be performed to track the use and return of objects during surgery. Such a manual approach is inefficient, requiring the time of highly trained personnel, and is prone to error.

Another approach employs transponders and a wireless interrogation and detection system. Such an approach employs wireless transponders which are attached to various objects used during surgery. The interrogation and detection system includes a transmitter that emits pulsed wideband wireless signals (e.g., radio or microwave frequency) and a detector for detecting wireless signals returned by the transponders in response to the emitted pulsed wideband signals. Such an automated system may advantageously increase accuracy while reducing the amount of time required of highly trained and highly compensated personnel. Examples of such an approach are discussed in U.S. Pat. No. 6,026,818, issued Feb. 22, 2000, and U.S. Patent Publication No. US 2004/0250819, published Dec. 16, 2004.

Commercial implementation of such an automated system requires that the overall system be cost competitive and highly accurate. In particular, false negatives must be avoided to ensure that objects are not mistakenly left in the patient. Some facilities may wish to install a single interrogation and detection system in each surgery theater, while other facilities may move an interrogation and detection system between multiple surgical theaters. In either case, the overall system will require a large number of transponders, since at least one transponder is carried, attached or otherwise coupled to each object which may or will be used in surgery. Consequently, the transponders must be inexpensive. However, inexpensive transponders typically have a relatively large variation in the frequency of signals they emit, making it difficult to accurately detect the signals returned by the transponders. This may be particularly difficult in some environments which are noisy with respect to the particular resonant frequencies of the transponders. Consequently, a new approach to detection of the presence and absence of transponder that facilitates the use of inexpensive transponders is highly desirable.

BRIEF SUMMARY

A transponder detection device to detect surgical objects in a work area, the surgical objects marked by respective resonant tag elements that produce return signals in response to energization, may be summarized as including a hand-held probe comprising: a housing having a cavity therein; and a first coil assembly and a second coil assembly received within the cavity of the housing spaced from each other, wherein each of the first and the second coil assemblies respectively includes: a substantially spherically shaped coil form that includes three coil support channels, each of the three coil support channels which define an outer coil support surface; a first antenna element comprising a first electrical conductor wound around the outer coil support surface of a first one of the three coil support channels, the first antenna element arranged to transmit and receive signals generally in a first coordinate direction; a second antenna element comprising a second electrical conductor wound around the outer coil support surface of a second one of the three coil support channels over the first electrical conductor, the second antenna element arranged to transmit and receive signals generally in a second coordinate direction orthogonal to the first coordinate direction; and a third antenna element comprising a third electrical conductor wound around the outer coil support surface of a third one of the three coil support channels over the first electrical conductor and the second electrical conductor, the third antenna element arranged to transmit and receive signals generally in a third coordinate direction orthogonal to the first coordinate direction and the second coordinate direction. The cavity of the housing may be defined by a first body portion that receives the first coil assembly, a second body portion that receives the second coil assembly, and a handle portion disposed between the first body portion and the second body portion. The handle portion may be disposed between the first body portion and the second body portion to allow the first body portion and the second body portion to at least partially surround a human joint during use.

The handle portion may include a handle portion cavity, and the hand-held probe may further include a circuit board disposed within the handle portion cavity and electrically coupled to the respective first antenna elements, the second antenna elements and the third antenna elements of the first and the second coil assemblies. At least one of the first, the second or the third antenna elements of the first coil assembly may be arranged to transmit and receive signals generally in a coordinate direction which is the same as a coordinate direction in which at least one of the first, the second or the third antenna elements of the second coil assembly is arranged to transmit and receive signals. Each of the first, the second and the third antenna elements of the first coil assembly may be arranged to transmit and receive signals generally in a coordinate direction which is the same as a coordinate direction in which a different one of the first, the second or the third antenna elements of the second coil assembly is arranged to transmit and receive signals. At least one of the first, the second or the third antenna elements of the first coil assembly may be coplanar with at least one of the first, the second or the third antenna elements of the second coil assembly. For each of the respective coil forms of the first and the second coil assemblies, each of the three coil support channels may be shaped as a spherical zone of a virtual sphere. For each of the respective coil forms of the first and the second coil assemblies, each of the three coil support channels may be shaped as a spherical zone of a virtual sphere centered on a great circle of the virtual sphere. For each of the respective coil forms of the first and the second coil assemblies, the three coil support channels may be shaped as a spherical zone of the substantially spherically shaped coil form centered on respective orthogonal great circles of the coil form.

The transponder detection device may further include a light source coupled to the housing that provides a visual indication of at least a status of the transponder detection device.

The transponder detection device may further include a processor operatively coupled to the respective first antenna elements, the second antenna elements, and the third antenna elements of the first and the second coil assemblies; and a nontransitory processor-readable medium communicatively coupled to the processor and that stores at least one of instructions or data executable by the processor, which cause the processor to: control each of the first antenna elements, the second antenna elements and the third antenna elements of the first and the second coil assemblies to emit wideband interrogation signals; receive any of the return signals from any of the resonant tag elements; and determine from a receipt of any of the return signals whether any of the resonant tag elements are present in the work area. The processor may control each of the respective first antenna elements, the second antenna elements and the third antenna elements of the first and the second coil assemblies to emit wideband interrogation signals in time-wise succession during a transmit portion of respective transmit and receive cycles, and controls each of the first antenna elements, the second antenna elements and the third antenna elements of the first and the second coil assemblies to not emit wideband interrogation signals during a receive portion of respective transmit and receive cycles. The processor may receive any of the return signals from any of the resonant tag elements during a receive portion of respective transmit and receive cycles. The processor may filter the any received return signals from noise to determine whether any of the resonant tag elements are present in the work area.

The processor may further receive a selection of at least one of a dynamic scan mode and a static scan mode; in response to receiving a selection of the static scan mode, may control each of the first antenna elements, the second antenna elements and the third antenna elements to emit wideband interrogation signals according to a static instrument scan cycle having a static instrument scan cycle duration; and in response to receiving a selection of the dynamic scan mode, may control each of the first antenna elements, the second antenna elements and the third antenna elements to emit wideband interrogation signals according to a dynamic instrument scan cycle having a dynamic instrument scan cycle duration that is less than the static instrument scan cycle duration. Tn response to receiving a selection of the static scan mode, the processor may control each of the first antenna elements, the second antenna elements and the third antenna elements to emit wideband interrogation signals centered on a first frequency, and further controls each of the first antenna elements, the second antenna elements and the third antenna elements to emit wideband interrogation signals centered on a second frequency, the second frequency different from the first frequency. The static instrument scan cycle duration may be less than fifteen (15) seconds and the dynamic instrument scan cycle duration mb less than five (5) seconds.

The processor may further determine from a receipt of any of the return signals whether any of the resonant tag elements are present in the work area based at least in part on a frequency of the return signals received being within a defined frequency range. The defined frequency range may include the frequency range of about 137 kHz to about 160 kHz.

The processor may further determine whether any of the resonant tag elements are present in the work area based at least in part on a Q value of the return signals received.

The processor may further determine whether any of the resonant tag elements are present in the work area based at least in part on a Q value of the return signals received being at least equal to a threshold Q value. The threshold Q value may be 35.

The processor may further determine whether any of the resonant tag elements are present in the work area based at least in part on a signal detection threshold.

The processor may further receive electromagnetic signals during a noise detection portion; determine a noise value indicative of a noise level that corresponds to a number of measurements of the electromagnetic signals received during the noise detection portion; adjust a signal detection threshold based at least in part on the determined noise value; and determine whether any of the resonant tag elements are present in the work area based at least in part on a number of measurements of the return signals received and the adjusted signal detection threshold.

The processor may further compare a maximum value of a plurality of matched filter outputs with the adjusted signal detection threshold.

The processor may further adjust the signal detection threshold to be approximately twice the determined noise value.

The processor may further determine if an output of at least one matched filter during the noise detection portion exceeds a noise fault threshold indicative of a noise fault. The wideband interrogation signals may be centered in at least one of a 136 kHz band, a 139 kHz band, a 142 kHz band, a 145 kHz band, a 148 kHz band, a 151 kHz band or a 154 kHz band.

A method to detect surgical objects in a work area, the surgical objects marked by respective resonant tag elements that produce return signals in response to energization, may be summarized as including providing a transponder detection device that includes a hand-held probe comprising a housing having a cavity therein; a first coil assembly and a second coil assembly received within the cavity of the housing spaced from each other, wherein each of the first and the second coil assemblies respectively includes: a substantially spherically shaped coil form that includes three coil support channels, each of the three coil support channels which define an outer coil support surface; a first antenna element comprising a first electrical conductor wound around the outer coil support surface of a first one of the three coil support channels, the first antenna element arranged to transmit and receive signals generally in a first coordinate direction; a second antenna element comprising a second electrical conductor wound around the outer coil support surface of a second one of the three coil support channels over the first electrical conductor, the second antenna element arranged to transmit and receive signals generally in a second coordinate direction orthogonal to the first coordinate direction; and a third antenna element comprising a third electrical conductor wound around the outer coil support surface of a third one of the three coil support channels over the first electrical conductor and the second electrical conductor, the third antenna element arranged to transmit and receive signals generally in a third coordinate direction orthogonal to the first coordinate direction and the second coordinate direction; emitting wideband interrogation signals via the respective first antenna elements, the second antenna elements and the third antenna elements of the first and the second coil assemblies; receiving any of the return signals from any of the resonant tag elements via at least one of the respective first antenna elements, the second antenna elements and the third antenna elements of the first and the second coil assemblies; and determining from a receipt of any of the return signals whether any of the resonant tag elements are present in the work area.

The method may further include positioning the handheld probe proximate a human body such that the first coil assembly and the second coil assembly at least partially surround a joint of the human body. Emitting wideband interrogation signals via the respective first antenna elements, the second antenna elements and the third antenna elements may include, for each of the first antenna elements, the second antenna elements and the third antenna elements, emitting a first wideband interrogation signal centered at a first frequency and emitting a second wideband interrogation signal centered at a second frequency, the second frequency different from the first frequency.

The method may further include controlling each of the first antenna elements, the second antenna elements and the third antenna elements to emit wideband interrogation signals in time-wise succession during a transmit portion of respective transmit and receive cycles and controlling each of the first antenna elements, the second antenna elements and the third antenna elements to not emit wideband interrogation signals during a receive portion of respective transmit and receive cycles.

The method may further include filtering the any received return signals from noise to determine whether any of the resonant tag elements are present in the work area.

The method may further include controlling each of the first antenna elements, the second antenna elements and the third antenna elements to emit wideband interrogation signals according to a static instrument scan cycle having a static instrument scan cycle duration; and controlling each of the first antenna elements, the second antenna elements and the third antenna elements to emit wideband interrogation signals according to a dynamic instrument scan cycle having a dynamic instrument scan cycle duration that is less than the static instrument scan cycle duration.

The method may further include receiving a selection of at least one of the dynamic instrument scan cycle and the static instrument scan cycle via the user interface.

The method may further include in response to receiving a selection of the static instrument scan cycle, controlling each of the first antenna elements, the second antenna elements and the third antenna elements to emit wideband interrogation signals centered on a first frequency; and controlling each of the first antenna elements, the second antenna elements and the third antenna elements to emit wideband interrogation signals centered on a second frequency, the second frequency different from the first frequency.

The method may further include determining from a receipt of any of the return signals whether any of the resonant tag elements are present in the work area based at least in part on a frequency of the return signals received being within a defined frequency range.

The method may further include determining whether any of the resonant tag elements are present in the work area based at least in part on a Q value of the return signals received.

The method may further include determining whether any of the resonant tag elements are present in the work area based at least in part on a Q value of the return signals received being at least equal to a threshold Q value.

The method may further include determining whether any of the resonant tag elements are present in the work area based at least in part on a signal detection threshold.

The method may further include receiving electromagnetic signals during a noise detection portion; determining a noise value indicative of a noise level that corresponds to a number of measurements of the electromagnetic signals received during the noise detection portion; adjusting a signal detection threshold based at least in part on the determined noise value; and determining whether any of the resonant tag elements are present in the work area based at least in part on a number of measurements of the return signals received and the adjusted signal detection threshold.

The method may further include comparing a maximum value of a plurality of matched filter outputs with the adjusted signal detection threshold.

The method may further include adjusting the signal detection threshold to be approximately twice the determined noise value.

The method may further include determining if an output of at least one matched filter during the noise detection portion exceeds a noise fault threshold indicative of a noise fault.

A transponder detection device may be summarized as including a first coil assembly and a second coil assembly spaced apart from each other, wherein each of the first and the second coil assemblies respectively includes: a coil form that includes three coil support channels, each of the coil support channels curved about a respective primary axis and curved about a respective secondary axis orthogonal to the respective primary axis, the primary axes orthogonal to one another.

The first and the second coil assemblies respectively may include a first antenna element comprising a first electrical conductor wound around a first one of the three coil support channels; a second antenna element comprising a second electrical conductor wound around a second one of the three coil support channels over the first electrical conductor; and a third antenna element comprising a third electrical conductor wound around a third one of the three coil support channels over the first electrical conductor and the second electrical conductor.

The transponder detection device may further include a processor operatively coupled to the respective first antenna elements, the second antenna element and the third antenna elements of the first and the second coil assemblies; and a nontransitory processor-readable medium communicatively coupled to the processor and that stores at least one of instructions or data executable by the processor, which cause the processor to: control each of the first antenna elements, the second antenna elements and the third antenna elements to emit wideband interrogation signals; receive return signals from one or more resonant tag elements; and determine from a receipt of any of the return signals whether any of the resonant tag elements are present in a work area. Curvatures of the three coil support channels about the respective primary axes may be equal to one another and equal to curvatures of the coil support channels about the respective secondary axes.

A transponder detection device may be summarized as including at least two coil forms spaced apart from each other, each of the coil forms respectively includes: a first coil support channel curved about a primary axis defined by a first axis and curved about a secondary axis defined by a second axis orthogonal to the first axis; a second coil support channel curved about a primary axis defined by third axis and curved about a secondary axis defined by the first axis, the third axis orthogonal to the first axis and the second axis; and a third coil support channel curved about a primary axis defined by the second axis and curved about a secondary axis defined by the first axis. Curvatures of the respective first, the second, and the third coil support channels about the respective primary axes may be equal to one another and equal to curvatures of the respective first, the second, and the third coil support channels about the respective secondary axes.

The transponder detection device may further include for each of the at least two coil forms, a first antenna element comprising a first electrical conductor wound around the first coil support channel; a second antenna element comprising a second electrical conductor wound around the second coil support channel over the first electrical conductor; and a third antenna element comprising a third electrical conductor wound around the third coil support channel over the first electrical conductor and the second electrical conductor.

The transponder detection device may further include a processor operatively coupled to the respective first antenna elements, the second antenna elements, and the third antenna elements; and a nontransitory processor-readable medium communicatively coupled to the processor and that stores at least one of instructions or data executable by the processor, which cause the processor to: control each of the first antenna elements, the second antenna elements and the third antenna elements to emit wideband interrogation signals; receive return signals from one or more resonant tag elements; and determine from a receipt of any of the return signals whether any of the resonant tag elements are present in a work area.

BRIEF DESCRIPTION OF THE SEVERAL VIEWS OF THE DRAWING(S)

In the drawings, identical reference numbers identify similar elements or acts. The sizes and relative positions of elements in the drawings are not necessarily drawn to scale. For example, the shapes of various elements and angles are not necessarily drawn to scale, and some of these elements may be arbitrarily enlarged and positioned to improve drawing legibility. Further, the particular shapes of the elements as drawn, are not necessarily intended to convey any information regarding the actual shape of the particular elements, and may have been solely selected for ease of recognition in the drawings.

FIG. 2D is a side elevational view of a transponder, according to yet a further illustrated implementation.

FIG. 2E is an end view of the transponder of FIG. 2D.

FIG. 2F is a cross-sectional view of the transponder of FIG. 2D, taken along section line 2F.

FIG. 2G is an isometric view of a ferrite core of the transponder of FIG. 2D.

Figure 8:
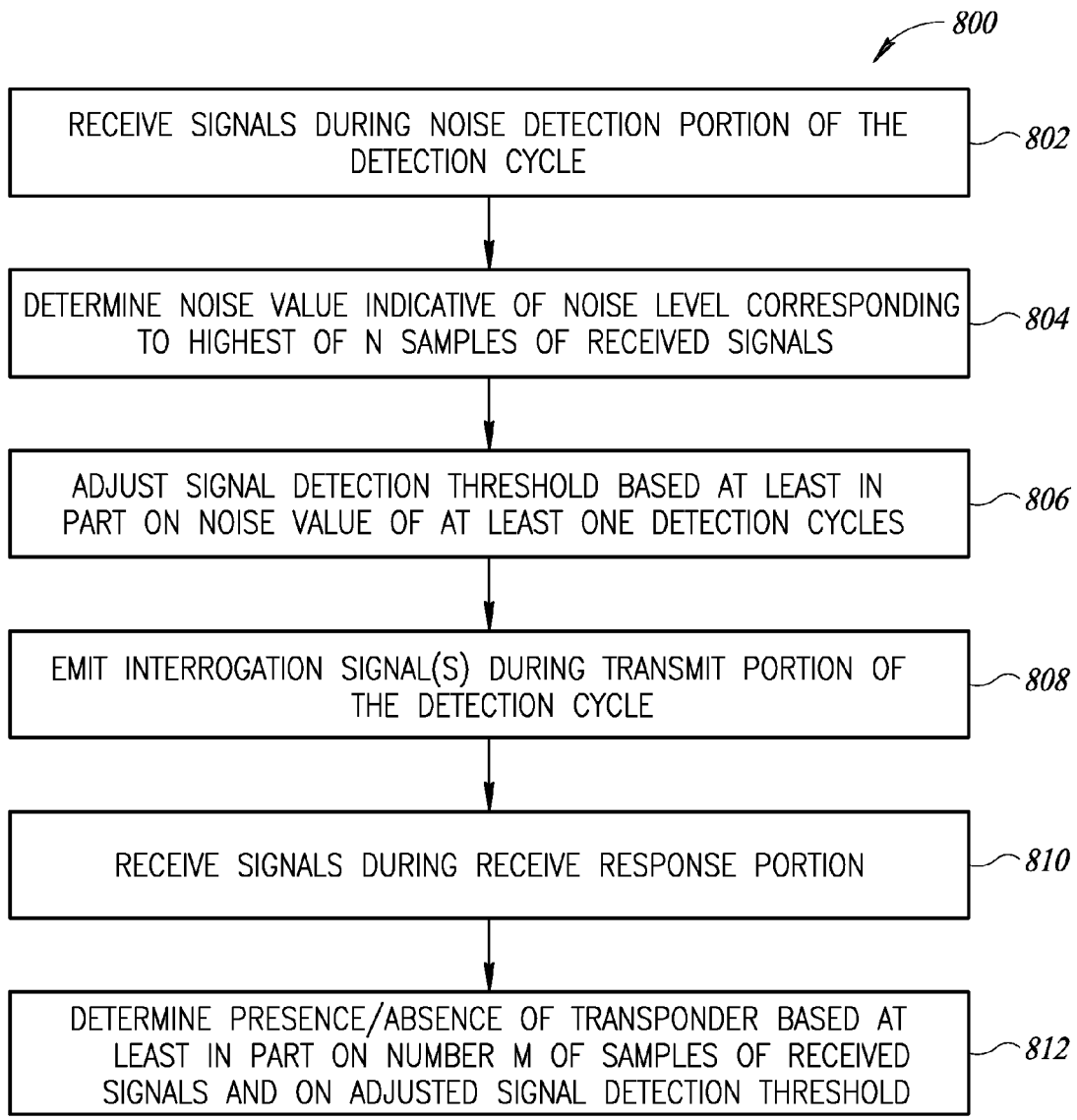

FIG. 8 is a flow diagram showing a method of operating an interrogation and detection system according to one illustrated implementation, including receiving electromagnetic signals, for example unmodulated electromagnetic signals, determining a noise value, adjusting signal detection threshold, emitting interrogations signals, receiving electromagnetic signals, and determining a presence or absence of a transponder based at least in part on the adjusted signal detection threshold.

Figure 9:
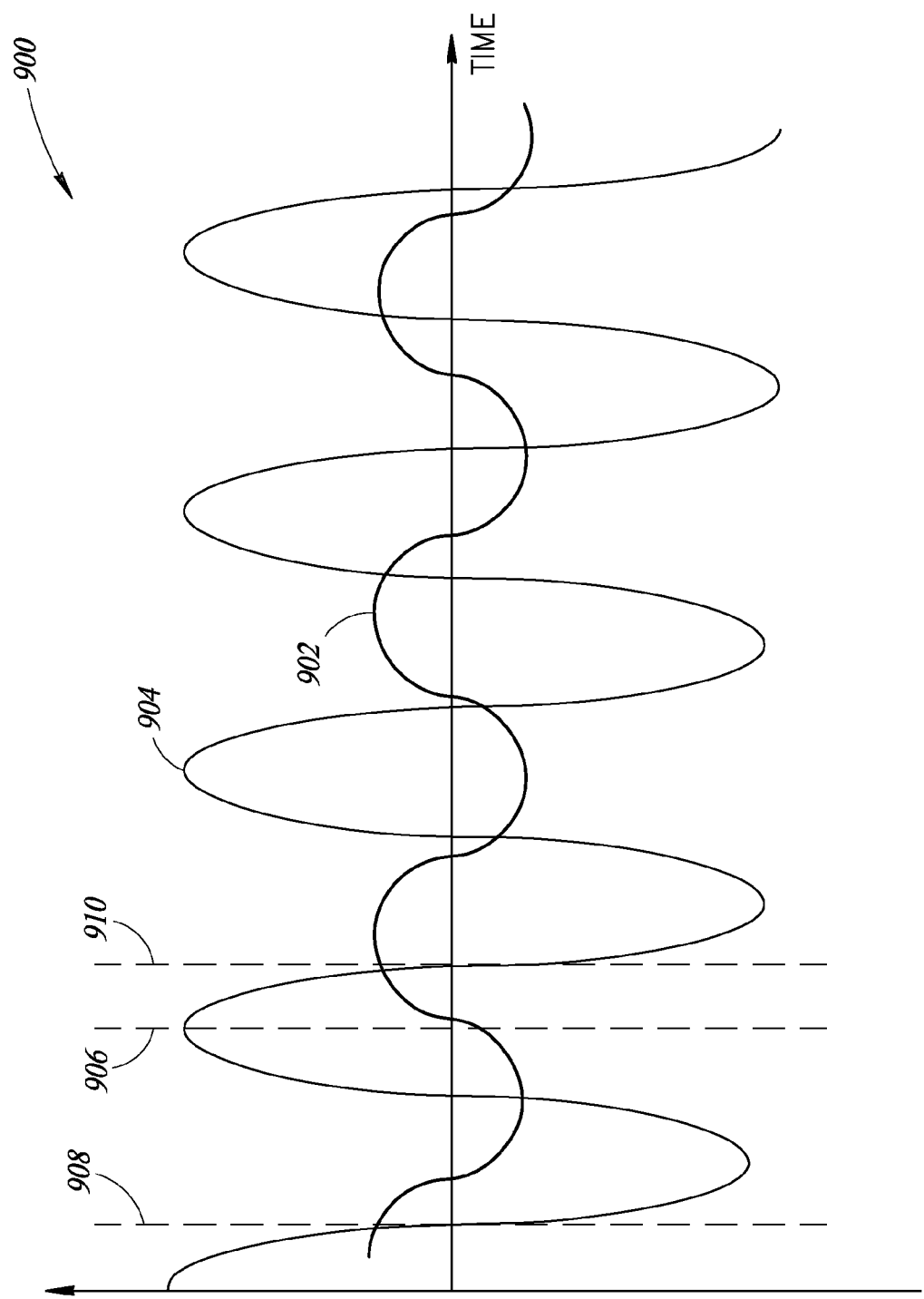

FIG. 9 is a graph showing noise and signal levels when the signal is sampled using subsample scan cycles, according to one illustrated implementation.

Figure 10:
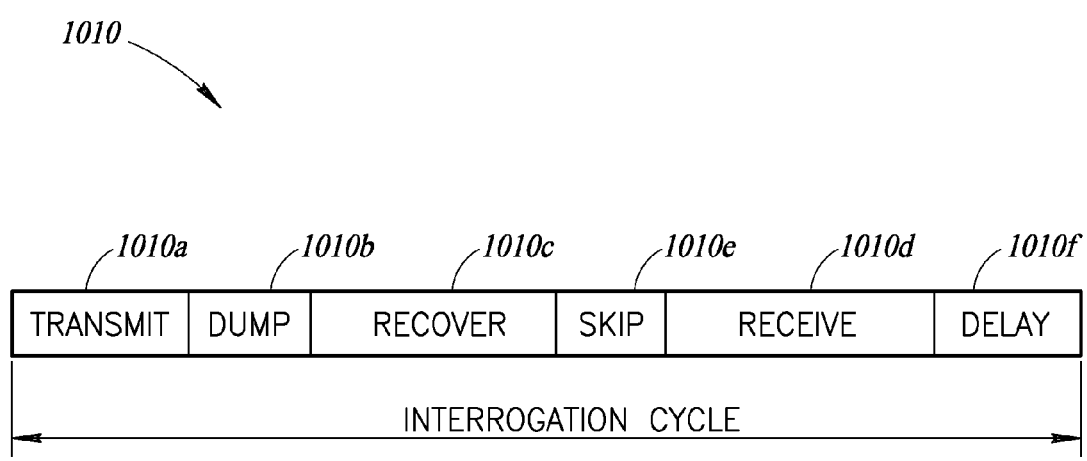

FIG. 10 is a timing diagram illustrating interrogation cycle timing, according to one illustrated implementation.

FIG. 11A is a timing diagram illustrating a scan cycle, according to one illustrated implementation.

FIG. 11B is a timing diagram illustrating a coil scan cycle, according to one illustrated implementation.

FIG. 11C is a timing diagram illustrating a frequency specific sample cycle, according to one illustrated implementation.

FIG. 11D is a timing diagram illustrating a subsample scan cycle, according to one illustrated implementation.

Figure 12:
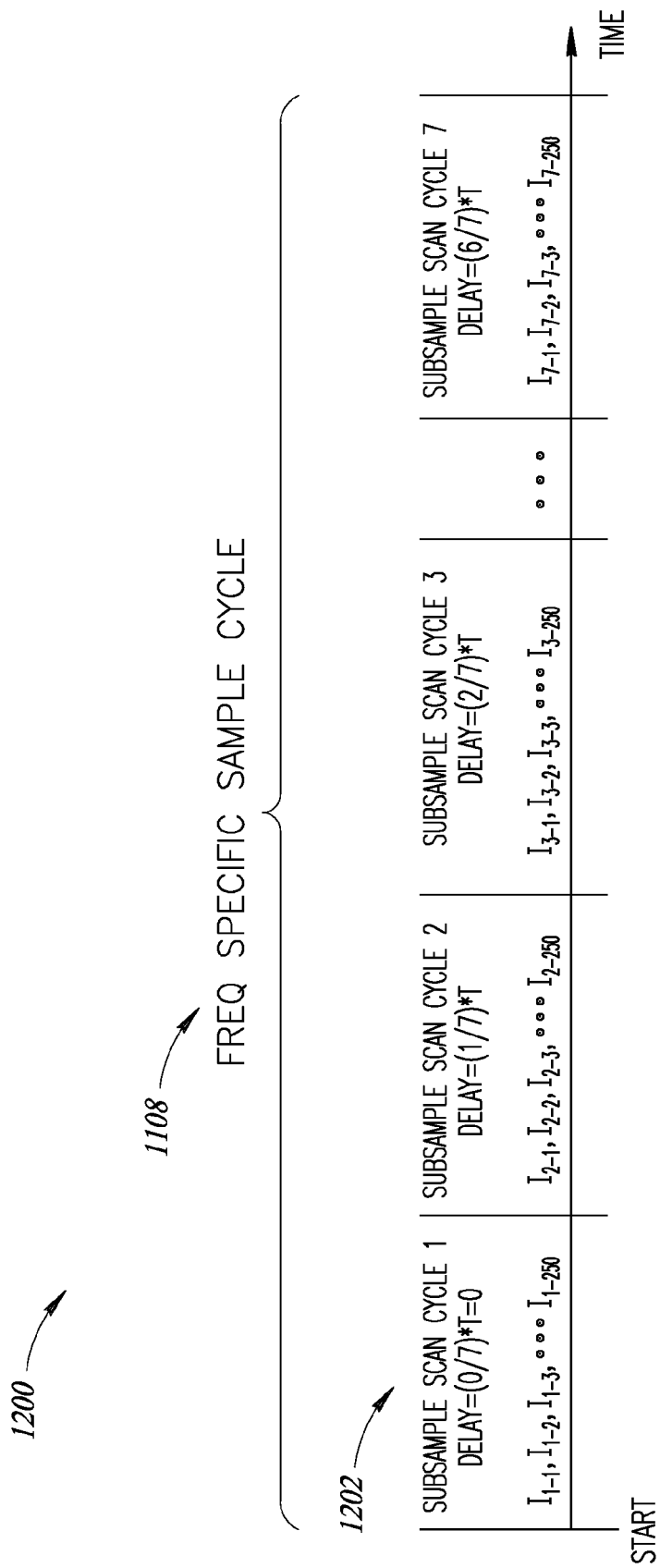

FIG. 12 is a timing diagram illustrating timing for obtaining subsamples utilizing subsample scan cycles, according to one illustrated implementation.

Figure 13:
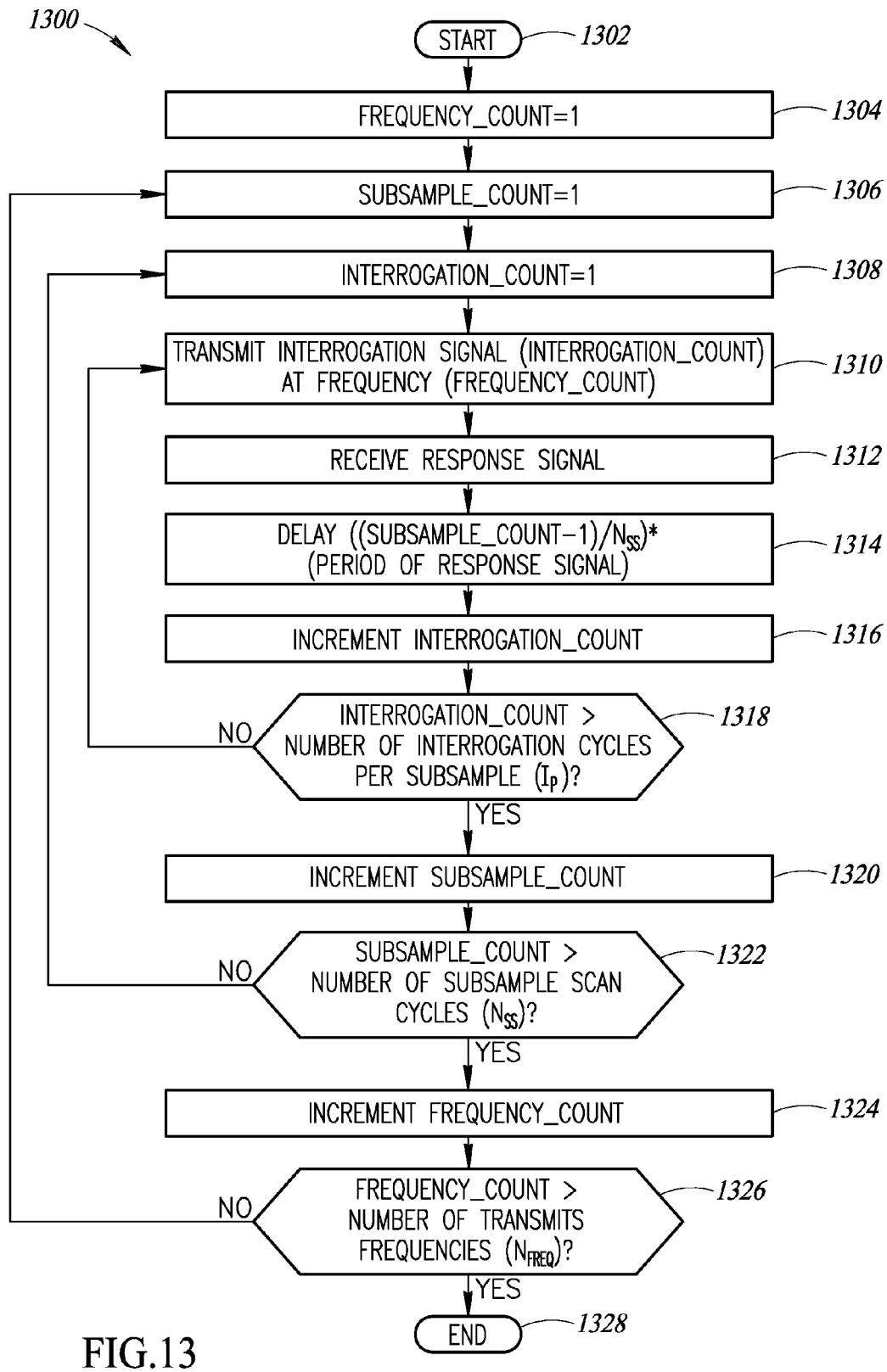

FIG. 13 is a flow diagram showing a process for a scanning method, according to one illustrated implementation.

Figure 14:
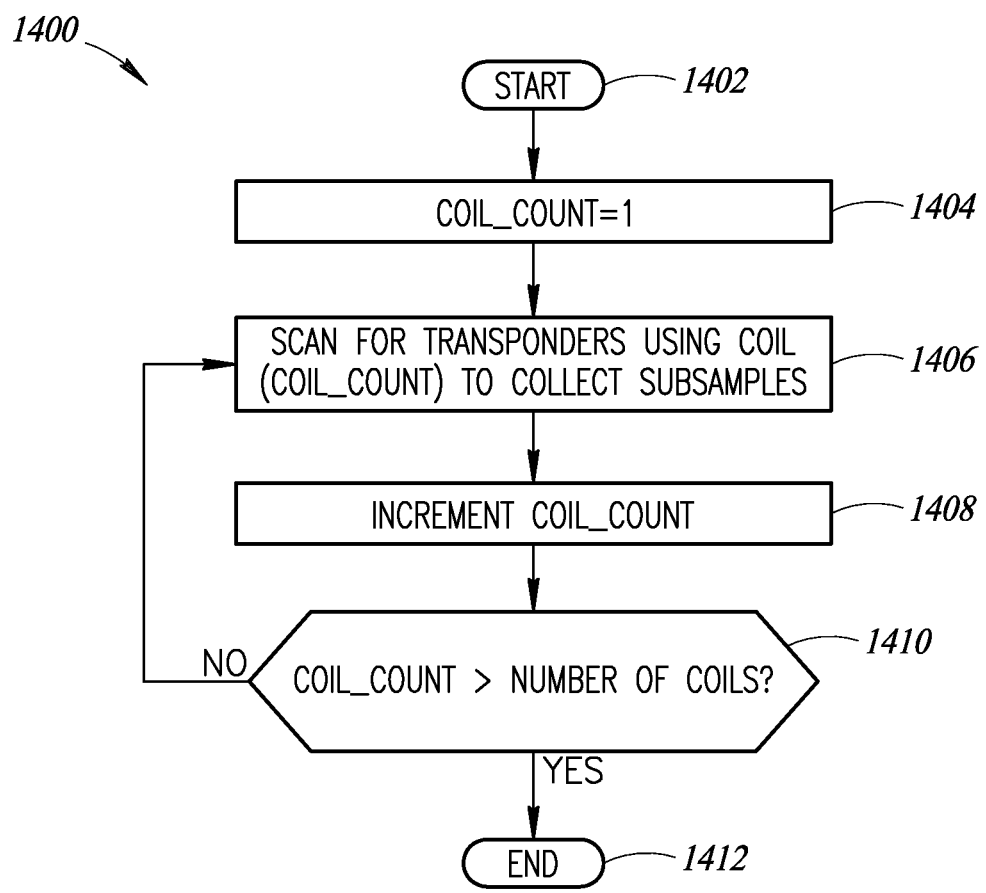

FIG. 14 is a flow diagram showing a process for a scanning method used with multiple coils, according to one illustrated implementation.

Figure 15:
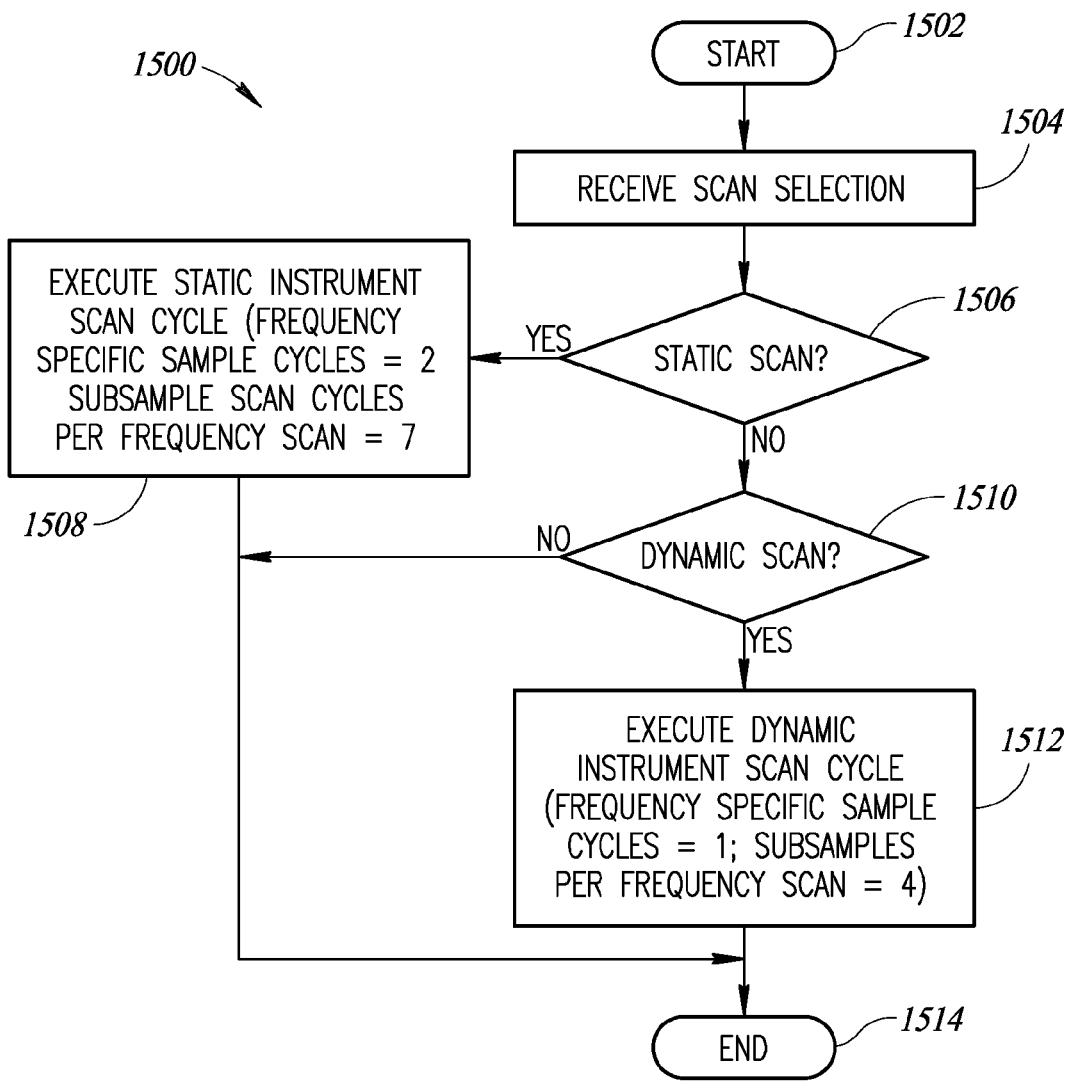

FIG. 15 is a flow diagram showing a process for implementing a dynamic instrument scan cycle and a static instrument scan cycle, according to one illustrated implementation.

Figure 16:
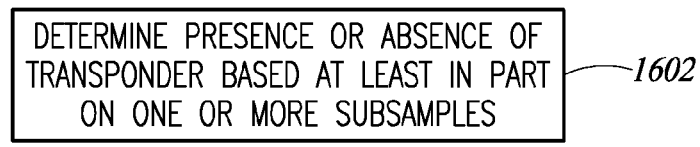

FIG. 16 is a flow diagram showing a method of determining the presence or absence of a transponder by evaluating one or more subsamples, according to one illustrated implementation.

Figure 3A:
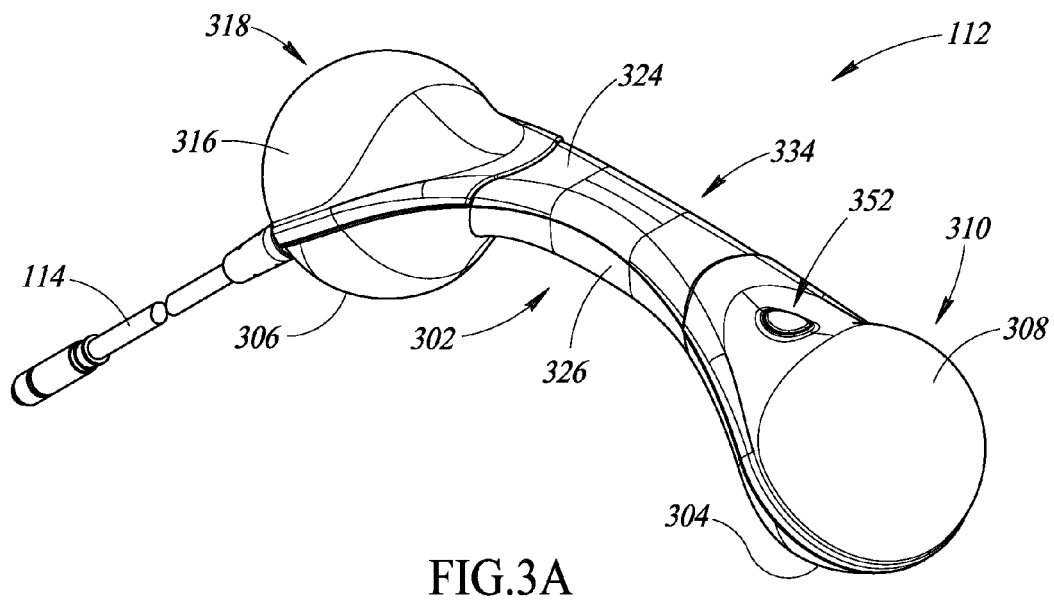
FIG. 3A is a top front isometric view of a probe of the interrogation and detection system, according to one illustrated implementation.
Figure 3B:
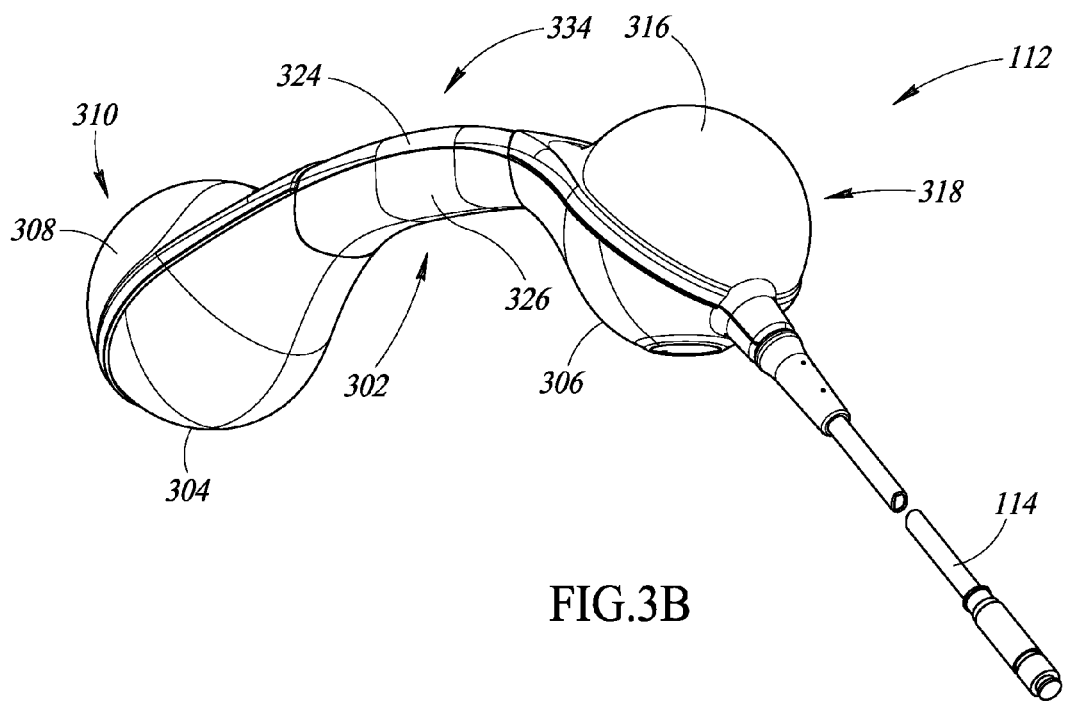
FIG. 3B is a bottom rear isometric view of the probe of the interrogation and detection system, according to one illustrated implementation.
Figure 3C:
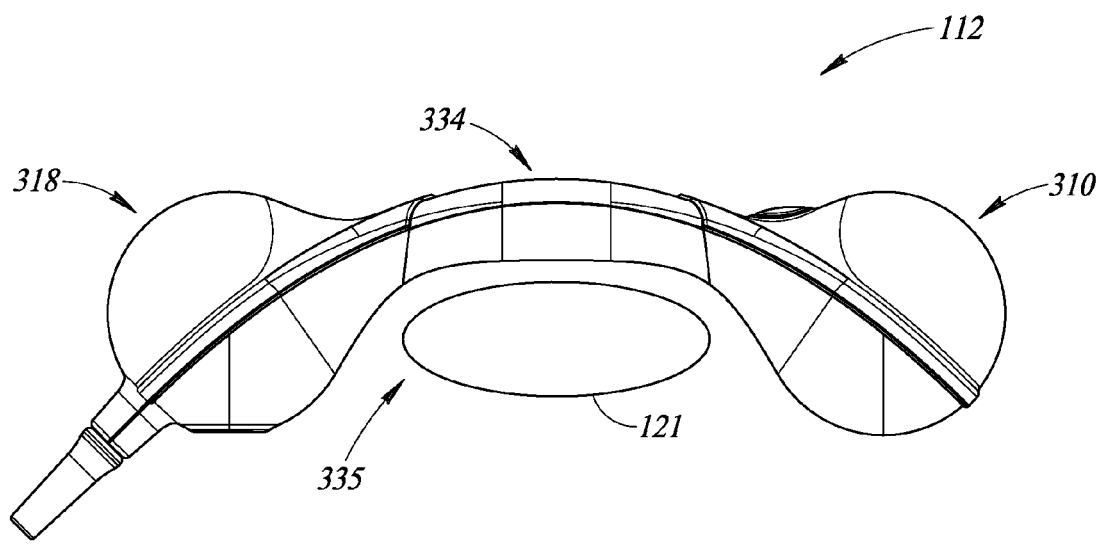
FIG. 3C is a right side elevational view of the probe of the interrogation and detection system, according to one illustrated implementation.
Figure 17:
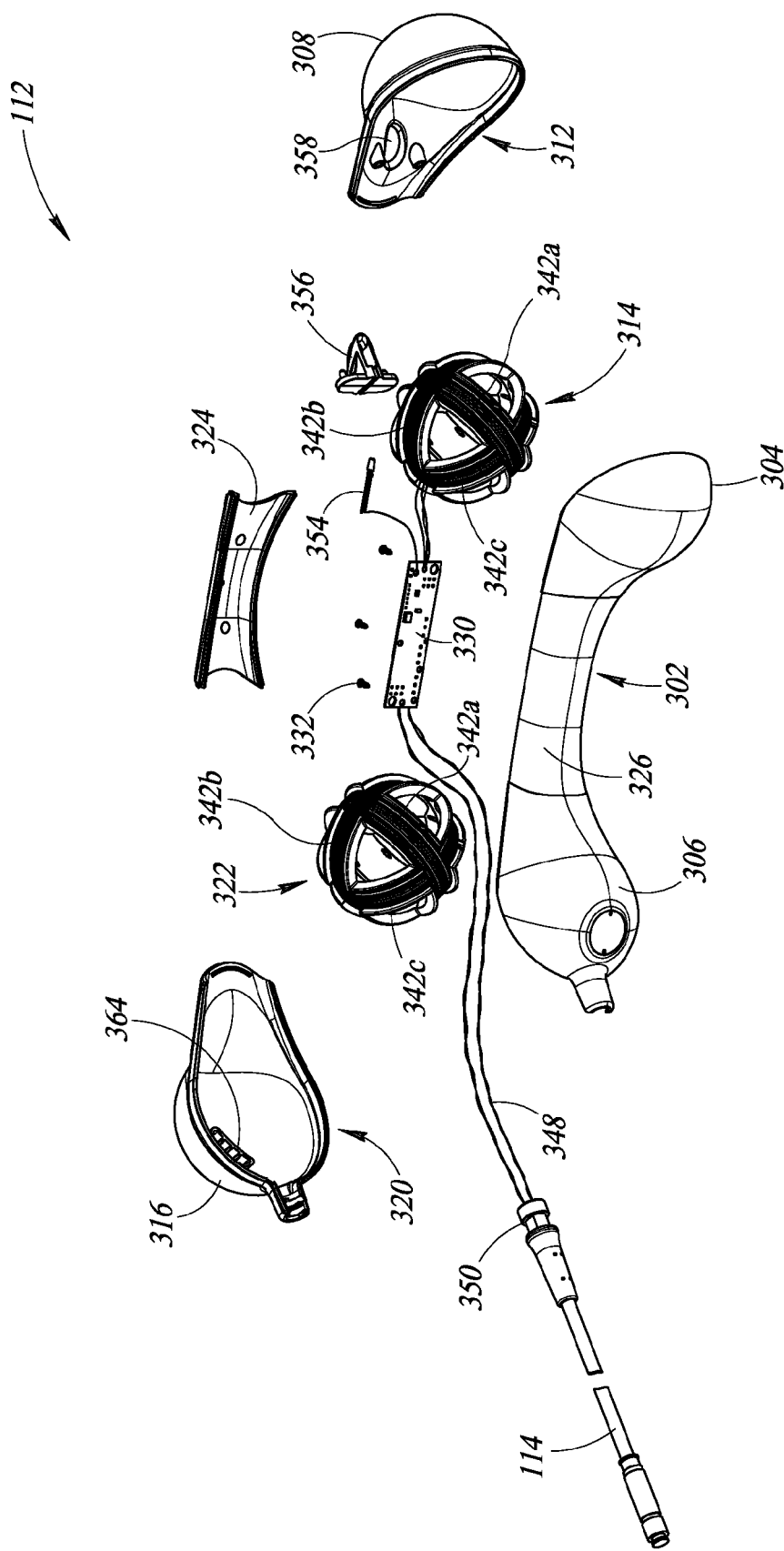

FIG. 17 is a bottom isometric, partially exploded view of the probe of the interrogation and detection system also shown in FIG. 3A.

Figure 18:
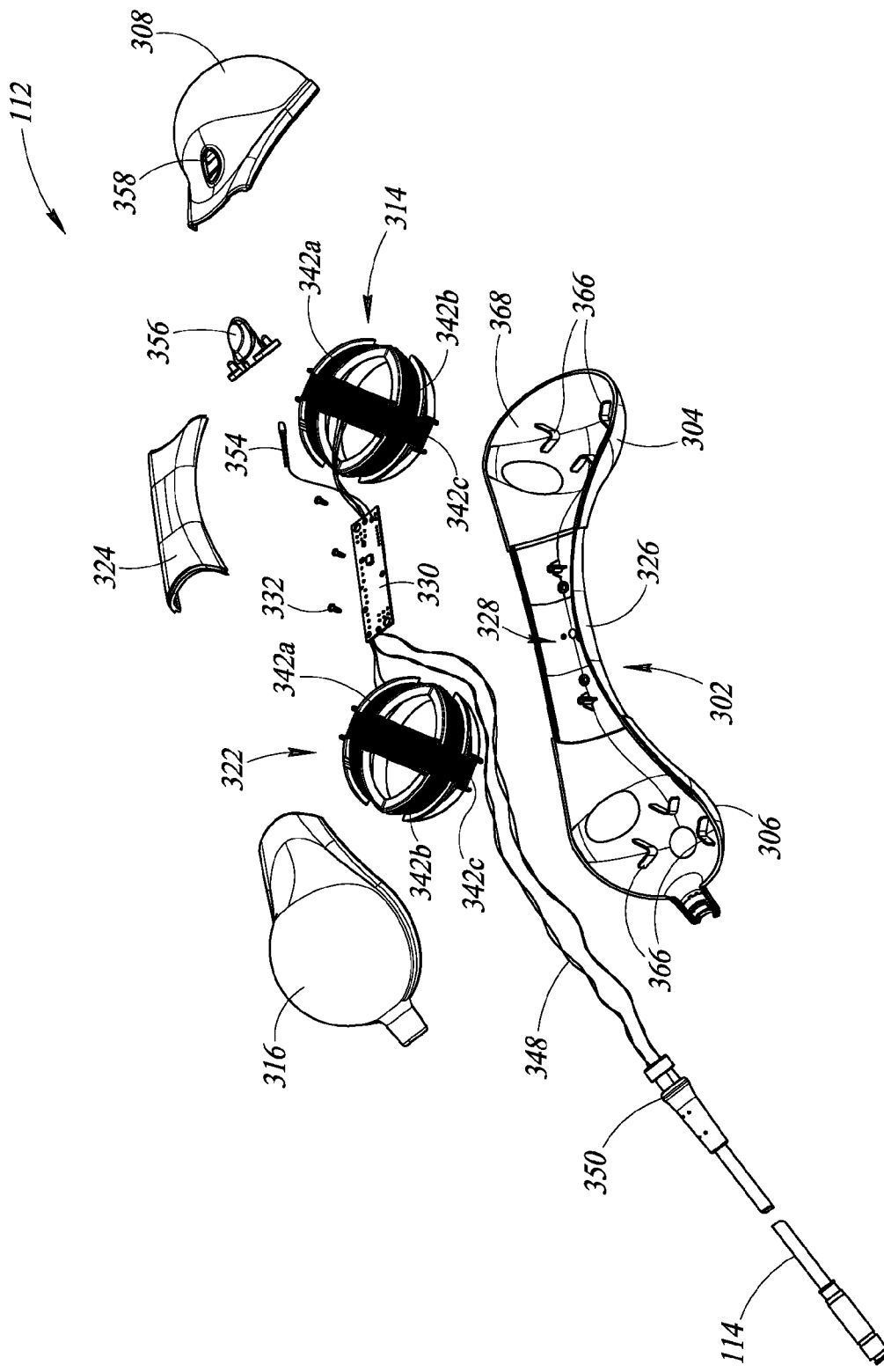

FIG. 18 is a top isometric, partially exploded view of the probe of the interrogation and detection system also shown in FIG. 3A.

Figure 19A:
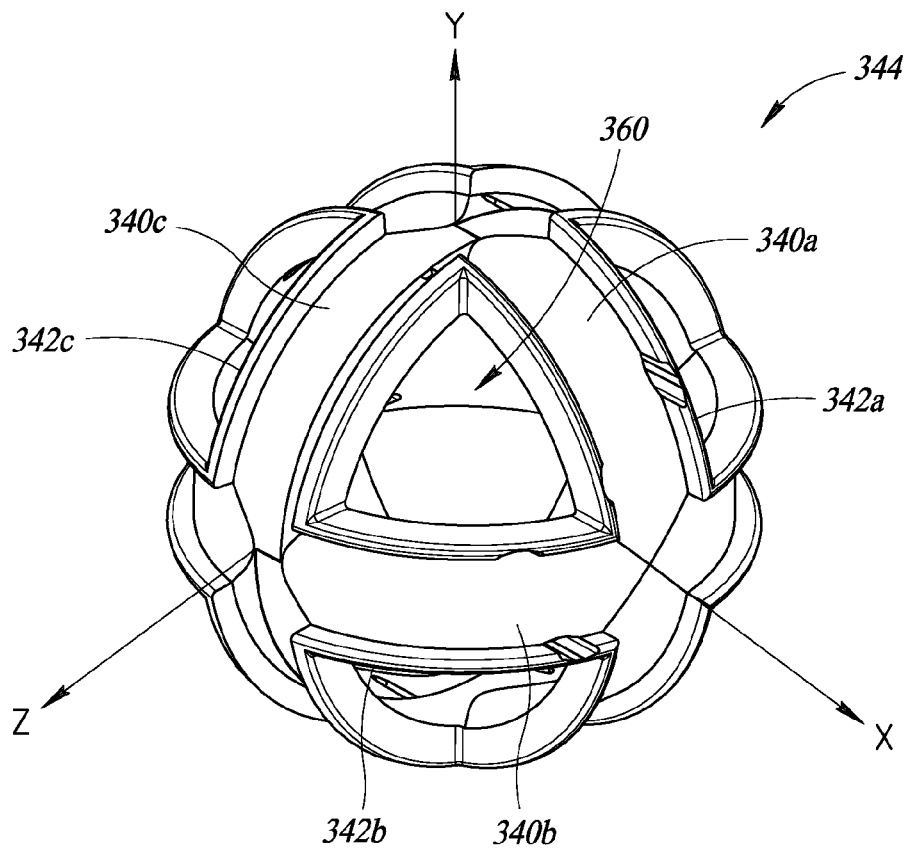

FIG. 19A is an isometric view of the coil form of the probe of the interrogation and detection system.

Figure 19B:
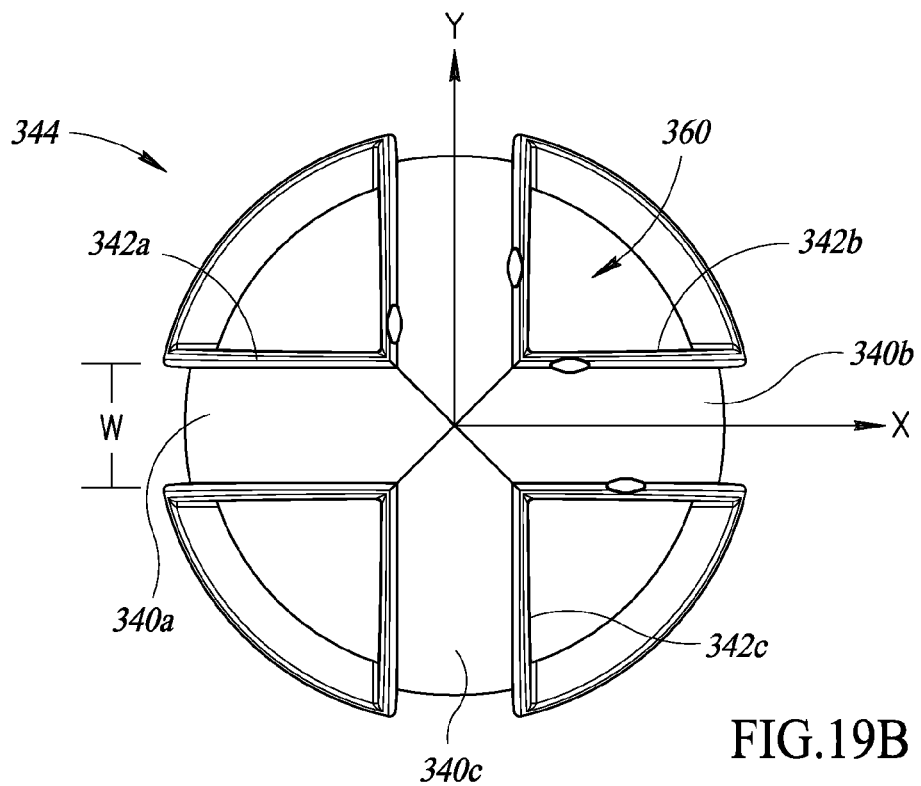

FIG. 19B is an elevational view of the coil form shown in FIG. 19A.

Figure 20:
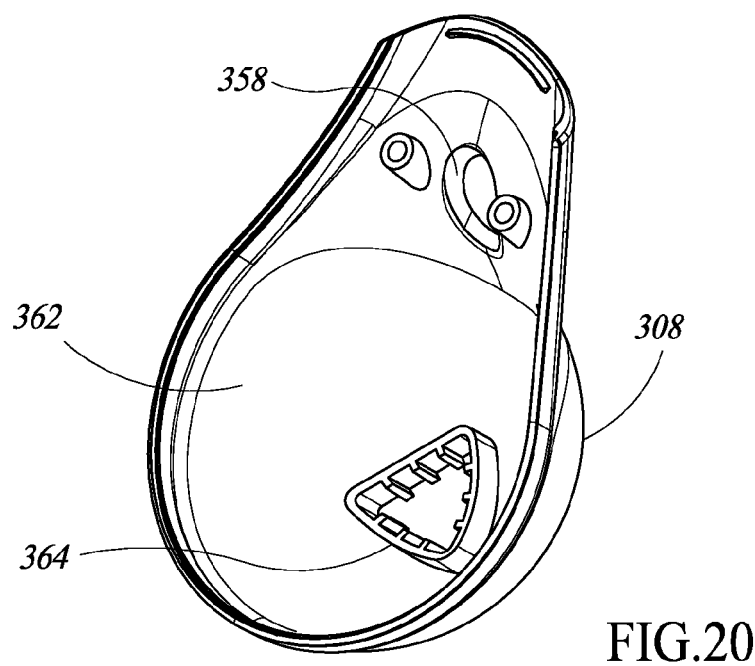

FIG. 20 is an isometric view of an inner surface of a right housing of the probe of the interrogation and detection system, illustrating an alignment rib.

Figure 21:
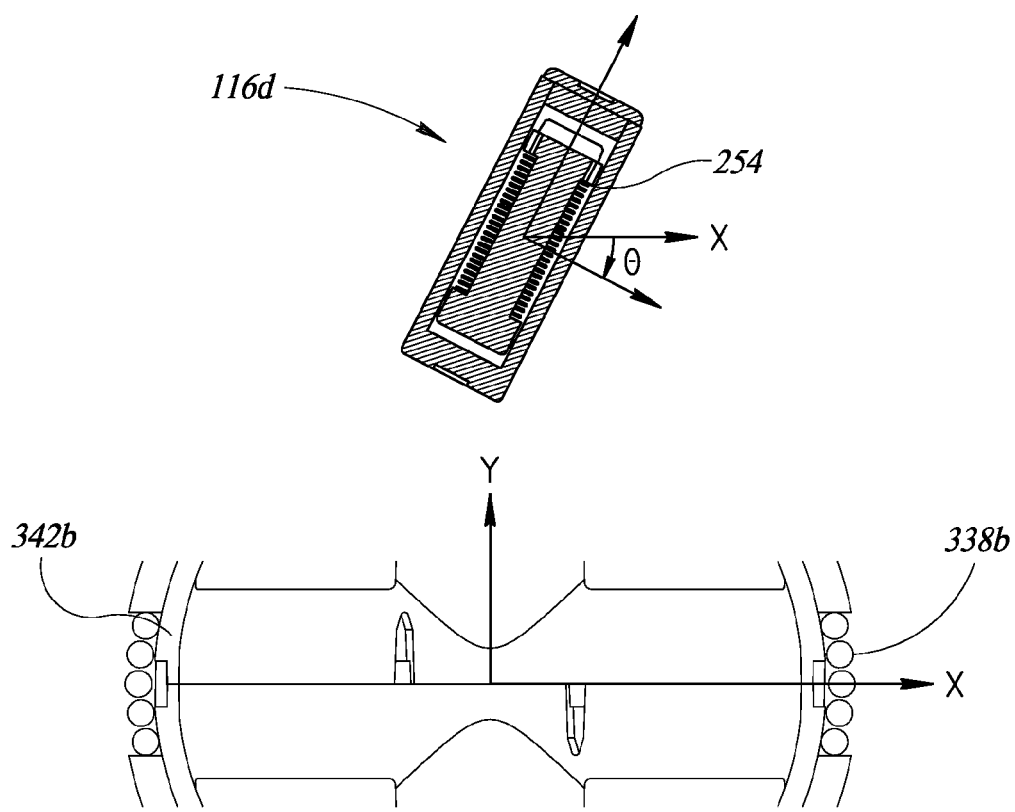

FIG. 21 is a sectional view of a coil of the probe, and a sectional view of a transponder disposed proximate to the coil.

Figure 22A:
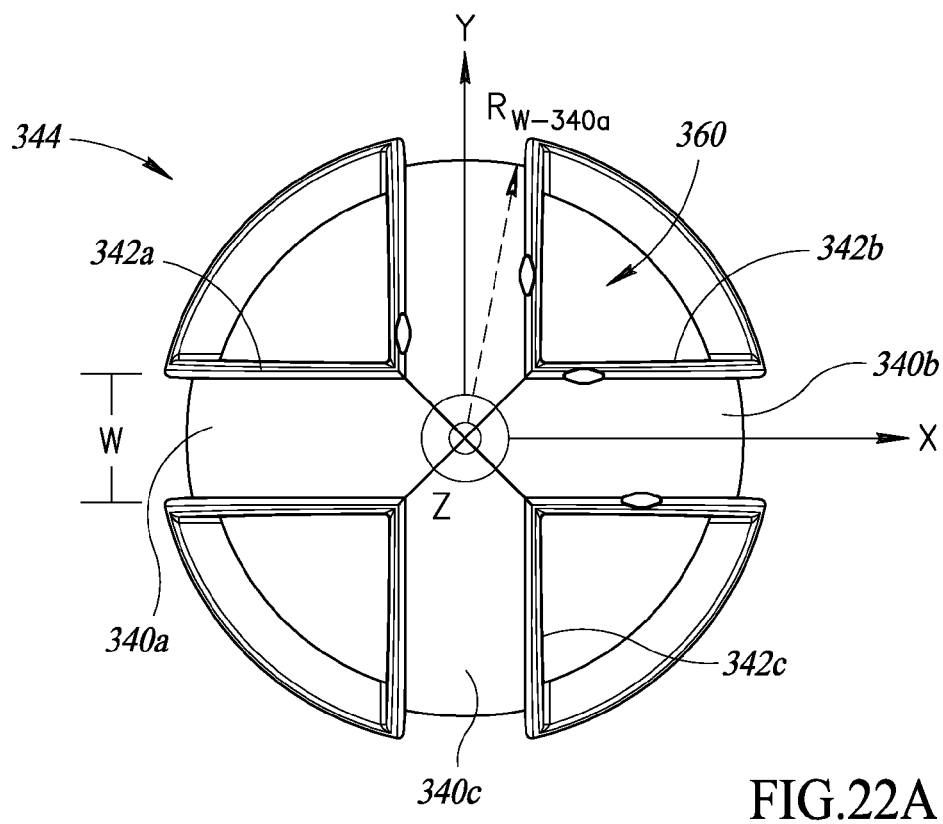

FIG. 22A is an elevational view of the coil form illustrating a radius of a length of an outer surface of a coil form channel.

Figure 22B:
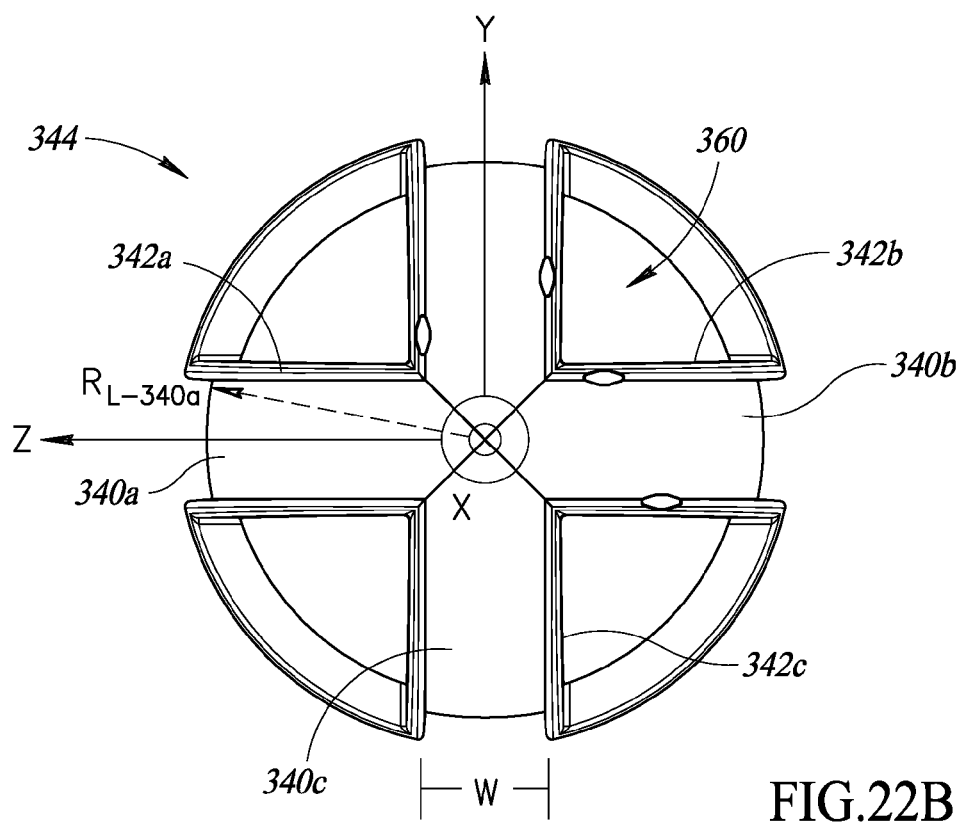

FIG. 22B is an elevational view of the coil form illustrating a radius of a width of an outer surface of a coil form channel.

DETAILED DESCRIPTION

In the following description, certain specific details are set forth in order to provide a thorough understanding of various disclosed implementations. However, one skilled in the relevant art will recognize that implementations may be practiced without one or more of these specific details, or with other methods, components, materials, etc. In other instances, well-known structures associated with transmitters, receivers, or transceivers have not been shown or described in detail to avoid unnecessarily obscuring descriptions of the implementations.

Unless the context requires otherwise, throughout the specification and claims that follow, the word "comprising" is synonymous with "including," and is inclusive or open-ended (i.e., does not exclude additional, unrecited elements or method acts).

Reference throughout this specification to "one implementation" or "an implementation" means that a particular feature, structure or characteristic described in connection with the implementation is included in at least one implementation. Thus, the appearances of the phrases "in one implementation" or "in an implementation" in various places throughout this specification are not necessarily all referring to the same implementation. Furthermore, the particular features, structures, or characteristics may be combined in any suitable manner in one or more implementations.

As used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The headings and Abstract of the Disclosure provided herein are for convenience only and do not interpret the scope or meaning of the implementations.

Figure 1A:
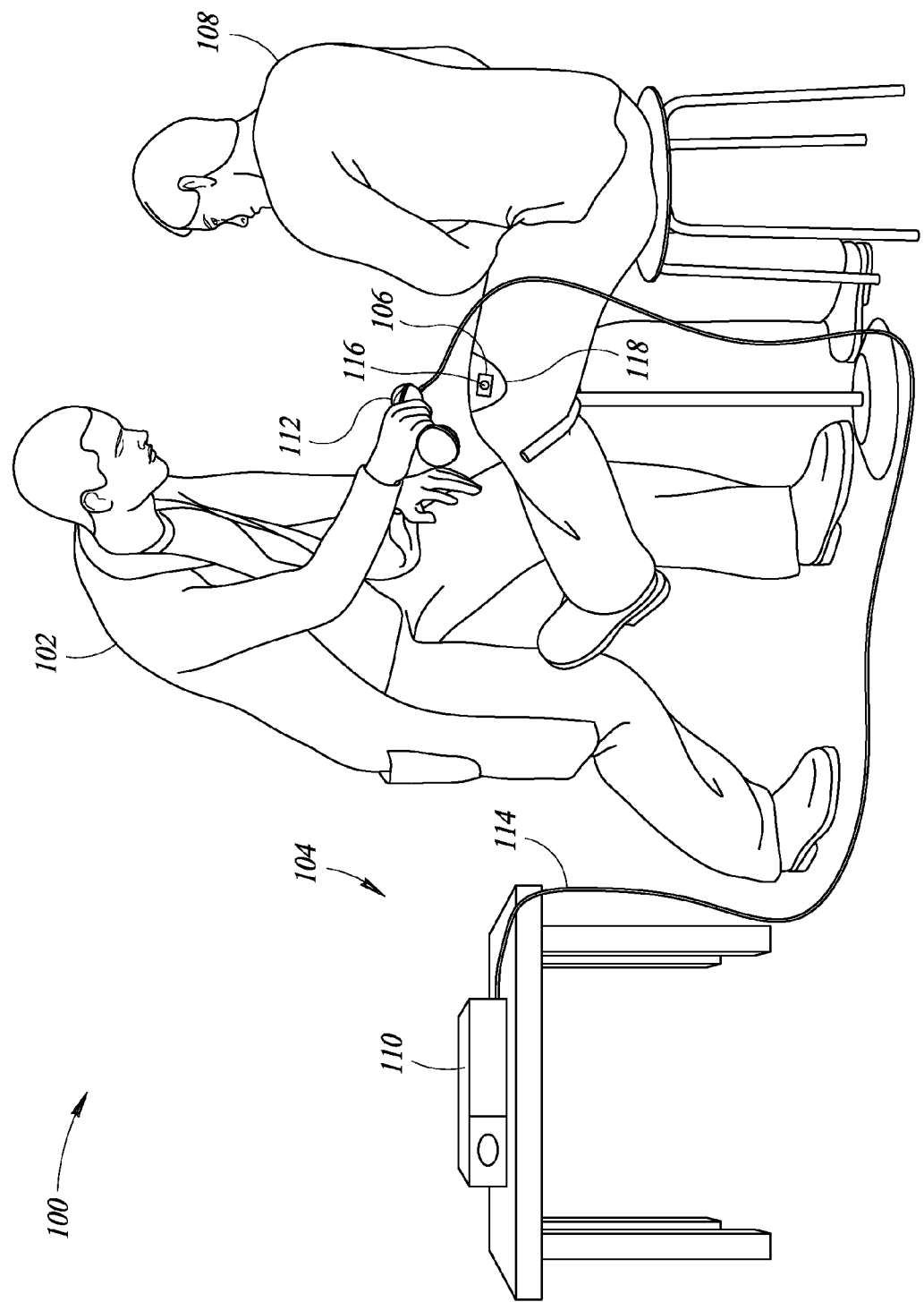
FIG. 1A is a schematic diagram showing a surgical environment illustrating a medical provider using an interrogation and detection system to detect an object tagged with a transponder in a patient, according to one illustrated implementation.
Figure 1B:
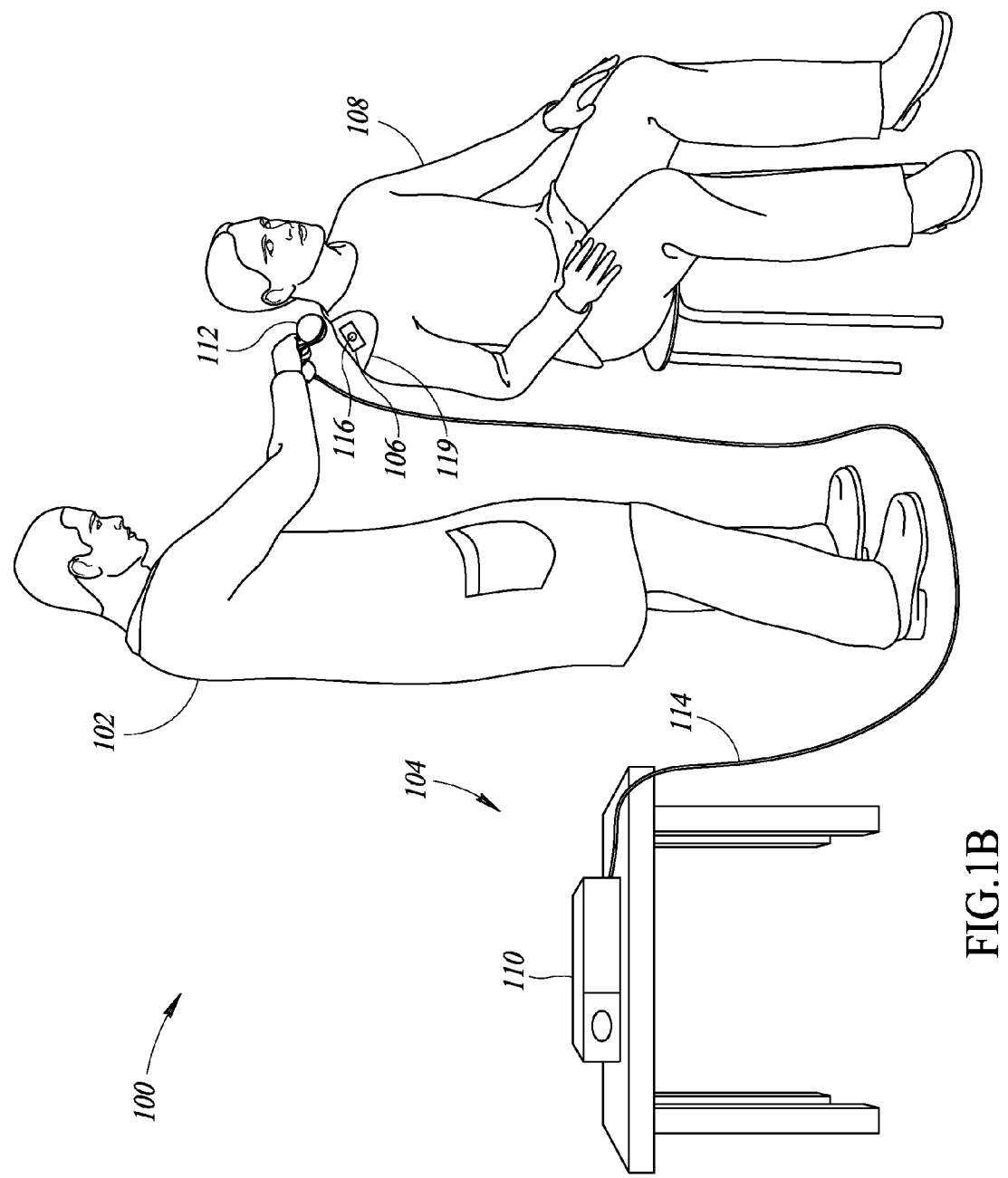
FIG. 1B is a schematic diagram showing another surgical environment illustrating a medical provider using the interrogation and detection system to detect an object tagged with a transponder in a patient, according to one illustrated implementation.

FIGS. 1A and 1B show an environment 100 in which a medical provider 102 operates an interrogation and detection system 104 to ascertain the presence or absence of objects 106 in, or on, a patient 108. The interrogation and detection system 104 may include a controller 110, and one or more coil assemblies 314 (see FIG. 3D) coupled to the controller 110 by one or more communication paths, for example coaxial cable 114. The antennas may be housed within a hand-held probe 112 that may include one or more antenna coils, for example. While designated as a probe, the blunt instrument is not necessarily intended to explore a wound or to even enter a patient's body. In many applications the hand-held probe will remain on the exterior outside of the patient's body (e.g., proximate a joint such as a knee, ankle, shoulder, hip, or neck). In some applications, for example labor and delivery (L&D), the patient may not have a wound.

The object 106 may take a variety of forms, for example instruments, accessories and/or disposable objects useful in performing surgical procedures. For instance, the object 106 may take the form of scalpels, scissors, forceps, hemostats, and/or clamps. Also for example, the objects 106 may take the form of surgical sponges, gauze and/or padding. The object 106 is tagged, carrying, attached or otherwise coupled to a transponder 116. Implementations of the interrogation and detection system 104 disclosed herein are particularly suited to operate with transponders 116 which are not accurately tuned to a chosen or selected resonant frequency. Consequently, the transponders 116 do not require high manufacturing tolerances or expensive materials, and thus may be inexpensive to manufacture.

In use, the medical provider 102 may position the probe 112 proximate the patient 108 in a fixed or static position to detect the presence or absence of the transponder 116 and hence an object 106. The medical provider 102 may in some implementations dynamically move the probe 112 along and/or across the body of the patient 108 or may move the probe near other areas, such as a near a trash can or drape bag in a surgery room. As show in FIG. 1A, the probe 112 may be sized to fit at least partially around a knee 118 of the patient 108 to detect the presence or absence of the transponder 116 and hence the object 106. As shown in FIG. 1B, the probe 112 may be sized to fit at least partially around a shoulder 119 of the patient to detect the presence or absence of the transponder 116 and hence the object 106. In practice, the probe 112 may be sized and shaped to fit at least partially around various joints of the patient 108.

Figure 2A:
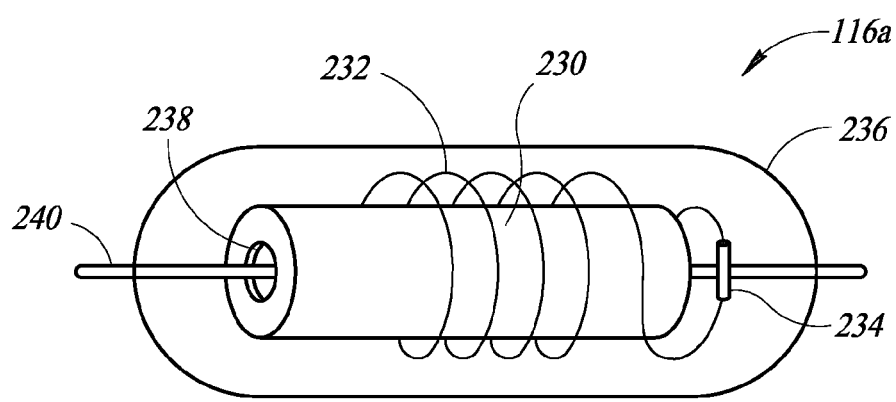
FIG. 2A is a schematic diagram of a transponder, according to one illustrated implementation.

FIG. 2A shows a transponder 116a according to one illustrated implementation. The transponder 116a includes a miniature ferrite rod 230 with a conductive coil 232 wrapped about an exterior surface thereof to form an inductor (L), and a capacitor (C) 234 coupled to the conductive coil 232 to form a series LC circuit. The conductive coil 232 may, for example, take the form of a spiral wound conductive wire with an electrically insulative sheath or sleeve. The transponder 116a may include an encapsulant 236 that encapsulates the ferrite rod 230, conductive coil 232, and capacitor 234. The encapsulant 236 may be a bio-inert plastic that protects the ferrite rod 230, conductive coil 232 and/or capacitor 234 from pressure and/or from fluids, for example bodily fluids.

In some implementations, the ferrite rod 230 may include a passage 238 sized to receive a physical coupler, for example a bonding tie or string 240. The bonding tie or string 240 may take the form of an elastomeric x-ray opaque flexible elongated member, that may be used to attach the transponder 116a to various types of objects 106, for example surgical sponges. The transponder 116a may have a length of about 8 millimeters and a diameter of about 2 millimeters. Employing such small dimensions ensures that the transponder 116a does not impede deformation of objects 106 such as sponges. The transponder 116a may include an optional diode (not shown), to protect against over-voltage occurrences caused by other electronic instruments.

Figure 2B:
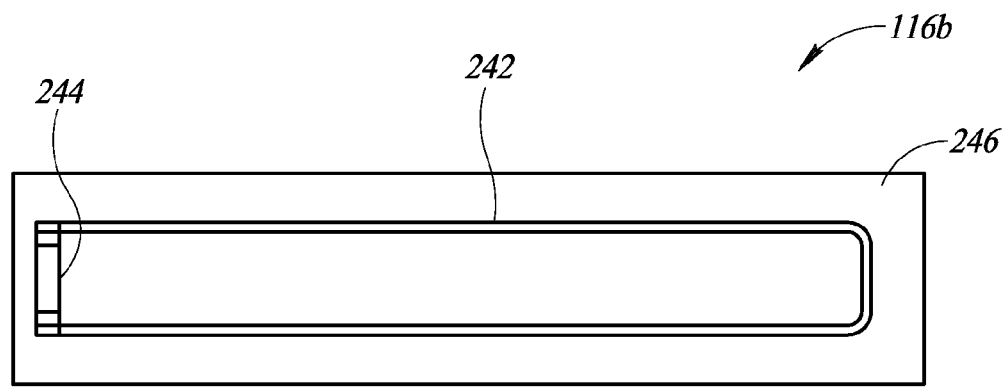
FIG. 2B is a schematic diagram of a transponder, according to another illustrated implementation.

FIG. 2B shows a transponder 116b, according to another illustrated implementation. The transponder 116b includes a single loop of conductive material 242, for example a loop of conductive wire forming an inductor (L), coupled in series to a capacitor 244 (C) to form an LC series circuit. The loop of conductive material 242 and capacitor 244 may be encapsulated in an elastomeric coating or sleeve 246. The dimensions of the transponder 116b may be similar to the dimensions of the transponder 116a. In some implementations, the dimensions of the transponder 116b are greater than the dimensions of the transponder 116a. The transponder 116b is highly flexible, and thus may provide its own thread-like or string-like attachment to various types of objects 106.

Figure 2C:
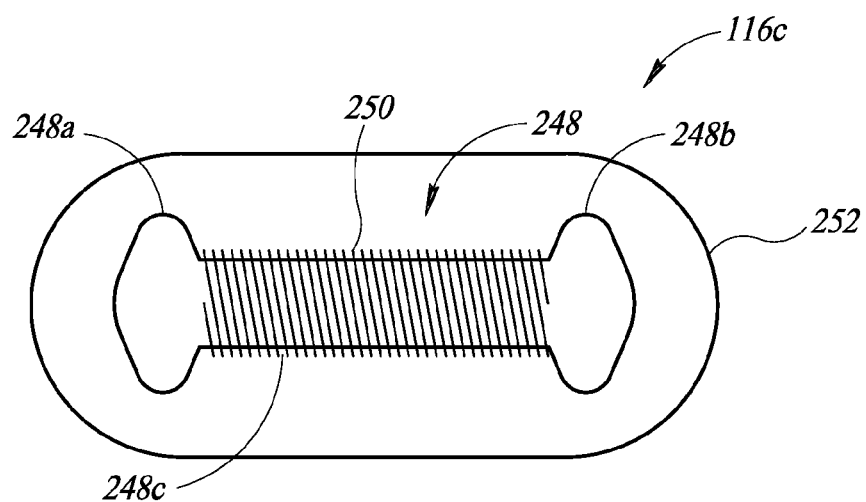
FIG. 2C is a schematic diagram of a transponder, according to a further illustrated implementation.

FIG. 2C shows a transponder 116c according to a further implementation. The transponder 116c includes a dumbbell-shaped ferrite rod 248 having broad end portions 248a, 248b, and a narrow intermediate portion 248c which is wrapped by a conductive coil 250. The broad end portions 248a, 248b contain the conductive coils 250. Such a design may provide stronger and/or more reliable signal emission than transponders 116a, 116b fashioned with cylindrical ferrite rods. The transponder 116c may optionally include an encapsulant 252. Further details regarding the transponder 116c may be found in U.S. Provisional Patent Application No. 60/811,376 filed Jun. 6, 2006, incorporated herein by reference. In some implementations, the transponder 116c may be formed as a fusiform-shaped object, with truncated ends. The fusiform shape may be advantageous over cylindrical shaped transponders 116a, 116b in reducing the likelihood of close parallel alignment of the transponders 116a, 116b, which may produce transponder-to-transponder interaction and interference.

FIGS. 2D-2G show a transponder 116d according to yet a further implementation. The transponder 116d includes a ferrite core 253, inductor (L) 254, and capacitor (C) 255 electrically coupled to the inductor 254 to form an LC series circuit. The transponder 116d also includes a capsule 256 with a cavity 257 open at one end to receive the ferrite core 253, inductor 254 and capacitor 255, as well as a lid 258 to close the open end of the capsule 256.

The ferrite core 253 may, for example, take the form of a soft ferrite drum, and may, for example, be formed of Nickel Zinc. Suitable ferrite cores 253 may be commercially available from TAK FERRITE as part no. L8A DR3X9 B=1.8 F=6 or from HUAH YOW under part no. 10R030090-77S. The drum may have a pair of larger diameter end portions 253a, 253b, with a smaller diameter intermediate portion 253c therebetween.

The inductor 254 may take the form of magnet wire wrapped around the intermediate portion 253c of the ferrite core 253. The magnet wire may, for example, have a dimension of approximately 41 American Wire Gauge (AWG), although some implementations may employ wires or conductors of larger or small gauges. Suitable inductors 254 may be commercially available from ELEKTISOLA under part no. PN-155 or from ROSEN under part no. 2UEW-F. The inductor may, for example, include approximately 432 turns, over approximately 6.5 layers, although some implementations may include a greater or lesser number of turns and/or layers. The transponder 116d may include tape and/or epoxy enveloping the inductor 254. Suitable tape may be commercially available from 3M under part nos. 1298, 1350-1 or PLEO 1P801, while suitable epoxy may be commercially available from LOCKTITE under part no. 3211.

The capacitor 255 may, for example, take the form of a ceramic capacitor. The capacitor 255 may, for example, have a capacitance of 470PF, 100V, with a Quality factor of Q>2200 @ 1 MHz. Suitable capacitors 255 may be commercially available from SANJV DIELECTRIC under part no. 0805NPO471J101 or from FENG HUA under part no. 0805CG471J101NT.

The capsule 256 and lid 258 may, for example, be formed of a polypropylene. Suitable capsules 256 and lids 258 may be commercially available from WEITHE ELECTRON (HK) COMPANY, under part specification CASE 4.3×12.6. The combination of the capsule 256 and lid 258 may, for example, have a length of approximately 12.8 mm and a diameter of 4.4 mm. Circuit bonds may, for example, employ UNITED RESINS CORP. part no. 63001500 CIRCUIT BOND LV, while solder may take the form of a lead free 96.5% Ag/3% Sn/0.5 Cu solder.

The transponders 116 may be attached to hemostats, scissors, certain forms of forceps, and the like. In some implementations, the transponders 116 may be coupled to the object 106 by way of a clamp or holder. In some implementations, the transponders 116 may be retained within a cavity of the holder. In some implementations, the holder may be fashioned of a durable deformable material, such as surgical grade polymer, which may be deformed to clamp securely onto the finger or thumbhole of an instrument. In other implementations, the transponders 116 may be attached to objects 106 by way of pouches fashioned of sheet material (e.g., surgical fabric) surrounding the transponder 116. The transponder 116 is retained within the pouch, and in some implementations the pouch may be sewn or otherwise sealed. Sealing may be done with adhesive, hot glue, clamping, grommeting, or the like.

FIGS. 3A-3D, 17, 18, 19A-19B, 20, 21, 22A and 22B show various views of the probe 112 also shown in FIGS. 1A-1B, according to one illustrated implementation.

As shown in FIGS. 3A, 3B, 17 and 18, the probe 112 includes a bottom housing 302 having a distal or front end portion 304 and a proximal or rear end portion 306 spaced apart from the front end portion. The probe 112 also includes a front top housing 308 that mates to the front end portion 304 of the bottom housing 302 to form a substantially spherical front body portion 310 that defines a cavity 312 that accommodates a front coil assembly 314 therein. The probe 112 also includes a rear top housing 316 that mates to the rear end portion 306 of the bottom housing 302 to form a substantially spherical rear body portion 318 that defines a cavity 320 that accommodates a rear coil assembly 322 therein.

The probe 112 may also include a top middle housing 324 that mates with a middle portion 326 of the bottom housing 302 between the front end portion 304 and the rear end portion 306 of the bottom housing to form a cavity 328 that accommodates a circuit board 330 electrically coupled to the front coil assembly 314 and the rear coil assembly 322. The circuit board 330 may be coupled to the middle portion 326 of the bottom housing 302 via one or more fasteners (e.g., screws 332). The front and rear top housings 308, 316 and the top middle housing 324 may be fixedly coupled to the bottom housing 302 during manufacture by any suitable process (e.g., an adhesive such as LOCTITE 414®, RF welding, friction fit, snap fit, tabs and lips, pins and holes, detents, etc.). The middle portions 324, 326 of the probe 112 may form a handle portion 334 extending between the spherical body portions 310 and 318. The handle portion 334 may be sized and dimensioned to be gripped by the hand of the medical provider 102 (FIGS. 1A-1B). In some implementations, the handle portion 334 may include an overmolded gripping surface. The overmolded gripping surface may be a material that provides a relatively high degree of tact and/or may be textured to facilitate non-slip gripping. In some implementations, the handle portion 334 may be shaped similar to that of a conventional phone, which is ergonomically desirable for the medical provider 102. Further, as shown best in FIG. 3C, the handle portion 334 is curved or bent between the first body portion 310 and the second body portion 318 to allow the first body portion and the second body portion to at least partially surround a joint 121 during use. The handle portion 334 and the body portions 310 and 318 together form an inverted trough or "U-shape" that forms a joint receiving portion 335 which receives the joint 121 during use. Thus, the body portions 310 and 318 may both be positioned simultaneously against sides of the joint 121 to increase the likelihood that a transponder 116 will be detected.

As noted above, the front and rear body portions 310 and 318 may define respective front and rear cavities 312 and 320 (FIG. 17) sized and dimensioned to receive the front and rear coil assemblies 314 and 322, respectively. FIGS. 3D, 19A-19B and 22A-22B show various views of portions of the front coil assembly 314. The rear coil assembly 322 may be substantially identical to the front coil assembly 314, so the discussion below regarding the front coil assembly also applies to the rear coil assembly.

The front coil assembly 314 may, for example, take the form of an air-coil formed of coils of conductive material, for example, electrical wire. The front coil assembly 314 acts as an inductor that facilitates magnetic inductive coupling with one or more coils of a transponder 116.

Figure 3D:
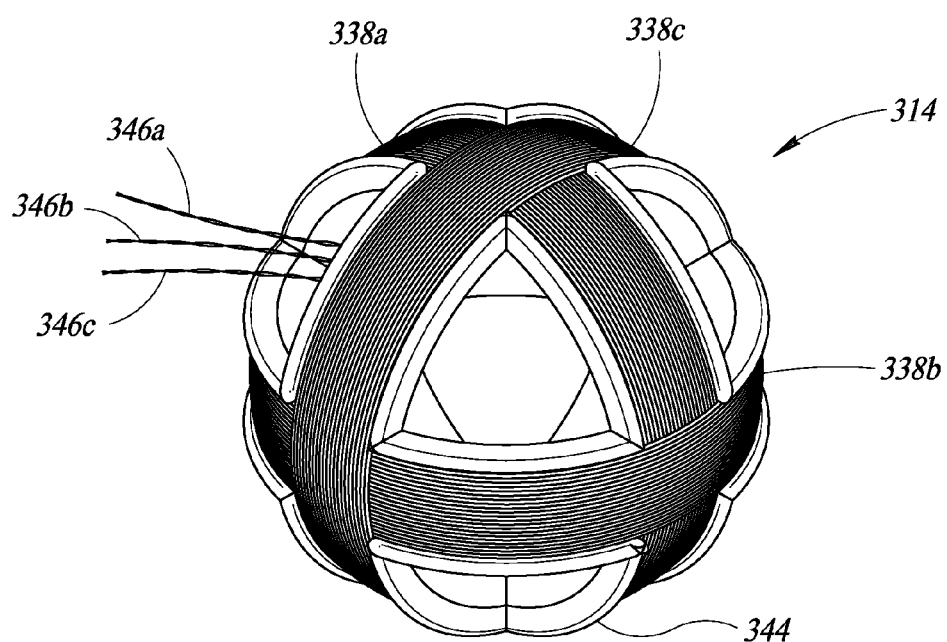
FIG. 3D is an isometric view of a coil form and three mutually orthogonal coils of the probe of FIG. 3A.

As shown in FIG. 3D, the front coil assembly 314 may include three antenna coils: a radially inner coil 338a, a radially middle coil 338b, and a radially outer coil 338c mutually orthogonal to each other. In the illustrated implementation, the antenna coils 338a, 338b, and 338c are wound around outer surfaces 340a, 340b, 340c, respectively (FIG. 19A), of respective coil form channels 342a, 342b, and 342c of a coil form or bobbin 344. Electrical wires or ends 346a, 346b, and 346c (FIG. 3D) of the respective coils 338a, 338b, and 338c may be electrically coupled to the PCT 330, which may be coupled to the controller 110 via the cable 114 (FIGS. 1A-1B). In some implementations, the coil form 344 may be a flexible printed circuit board (e.g., relatively few laminations of FR4). The coil form 344 may include strain relief structures or features such as notches, or cutouts laterally across the width of the printed circuit board and/or extending into the surface or along the edges of the printed circuit board.

As shown in FIGS. 17 and 18, the electrical wires 346a, 346b, and 346c, of the respective coils 338a, 338b, and 338c may be coupled to the printed circuit board 330, which may in turn be coupled to wires 348 of a coupling member 350, which may be positioned in the cavity 320 in the rear body portion 318 to provide a connector to communicatively couple to an end of the coaxial cable 114 to the antenna coils of the first and second coil assemblies 314 and 322. The coupling member 350 may take the form of a standard coaxial connector, for example. Some implementations may employ other types of wired and/or wireless communications pathways between the controller 110 and the coil assemblies 314 and 322, and thus may employ other types of coupling members or connectors.

In some implementations, the probe 112 may include one or more user interface devices, for example one or more visual indicators 352 (FIG. 3A) to provide visual indications to the medical provider 102. Such may, for example, take the form of one or more light emitting diodes 354 (FIG. 17), which may provide one or more different colors. Such user interface devices may additionally or alternatively include a speaker or other transducer (e.g., piezoelectric transducer, electric motor), operable to provide a sound or other sensory indication, for example a tactile sensation (e.g., vibration). Such user interface devices may be operable to provide sensory feedback to the medical provider 102 indicative of an operating condition of the interrogation and detection system 104. For example, such may indicate when the interrogation and detection system 104 is operating, when the presence of a transponder 116 has been identified, and/or when an error has occurred. Locating user interface devices on the probe 112 may be advantageous since the medical provider 102 will typically focus their attention on the probe 112 while scanning the patient 108.

In the illustrated implementation, the printed circuit board 330 includes the light emitting diode 354 (FIG. 17) coupled thereto. A light pipe 356 may be positioned within an aperture 358 of the front top housing 308. The light pipe 356 is light transmissive such that light from the light emitting diode 354 may pass through the light pipe where it is visible by a user. The light emitting diode 354 may be used to provide a visual indication to a user of the probe 112, such as status information or operational information.

As shown in FIGS. 3D, 19A and 19B, the generally spherical coil form 344 includes the three mutually orthogonal coil form channels 342a, 342b, and 342c each having a respective outer surface 340a, 340b, and 340c for supporting a respective one of the coils 338a, 338b, and 338c. As shown in FIG. 19A, the first coil form channel 342a is oriented in an XY plane, the second coil form channel 342b is oriented in an XZ plane, and the third coil form channel 342c is oriented in a YZ plane. The three coil form channels 342a, 342b, and 342c may intersect each other or may be nested. Each of the three coil form channels 342a, 342b, and 342c defines its respective outer coil support surface 340a, 340b, and 340c. Each outer coil support surface 340a, 340b, 340c is substantially cylindrically shaped with a curved surface. More specifically, in the illustrated implementation each outer coil support surface 340a, 340b, and 340c is shaped as a spherical zone of a virtual sphere, the spherical zone having a width W (FIG. 19B) and being centered on a great circle of the virtual sphere. As used herein, a great circle of a sphere is the intersection of the sphere and a plane which passes through the center point of the sphere. As used herein, a spherical zone is the surface of a spherical segment, which is a solid defined by cutting a sphere with a pair of parallel planes. In this case, the parallel planes are also parallel to a great circle of the virtual sphere and spaced apart on each side of the great circle by an equal distance (i.e., W/2), such that the spherical segment is centered on the great circle.

As shown in FIGS. 22A and 22B, each of the outer coil support surfaces have a circumference or length L that is defined by a body of revolution about a respective primary axis and a width W that is curved about a respective secondary axis orthogonal to the primary axes. Specifically, the length L of the outer coil support surface 340a is defined by a revolution about the Z axis (FIG. 22A) and the width W is curved about the X axis (FIG. 22B). The length L of the outer coil support surface 340b is defined by a revolution about the Y axis and the width W is curved about the Z axis. The length L of the outer coil support surface 340c is defined by a revolution about the X axis and the width W is curved about the Z axis.

The curvatures of the length L and the width W of each of the outer coil support surfaces 340a-340c are equal to each other. For example, the length L of the outer coil surface 340a at its center may be defined by a circle in the XY plane having a curvature radius $R_{L-340a}$ (FIG. 22A). The width W of the outer coil surface 340a has a radius of curvature of $R_{W-340a}$ (FIG. 22B), which is equal to the radius $R_{L-340a}$ of the length L.

As shown in FIGS. 19A and 19B, eight apertures 360 shaped as spherical triangles may be defined by the intersection of the coil form channels 342a, 342b, and 342c. The size of the eight apertures 360 is dependent on the width W of the coil form channels 342a, 342b, and 342c. That is, the wider the width W of coil form channels 342a, 342b, and 342c, the smaller the eight apertures 360. In some implementations, the apertures 360 are not present and the coil form 344, such that the coil form is substantially shaped as a sphere without apertures therein. In some implementations, the interior of the coil form 344 may be hollow, whereas in other implementations one or more materials may be present within the interior of the coil form.

As shown in FIG. 20, an interior surface 362 of the front top housing 308 may include an alignment rib 364 shaped and sized to be inserted into one of the spherical triangle-shaped apertures 360 of the coil form 344. The front end portion 304 of the bottom housing 302 may also include an alignment rib 366 on an interior surface 368 thereof. The alignment ribs 364 and 366 on the respective interior surfaces 362 and 368 of the housings 308 and 302 align the coil form 344 relative to the housings during manufacturing and fix the position of the coil form with respect to the assembled housing. The coil form 344 may be secured to the front end portion 304 of the bottom housing 302 and the front top housing 308 by a suitable adhesive (e.g., PC-11 A and PC-11 B two-part epoxy). The rear coil assembly 322 may be secured to the rear end portion 306 of the bottom housing 302 and the rear top housing 316 in a similar manner.

As shown in FIG. 3D, the first coil 338a is wound around the outer coil support surface 340a of the first coil support channel 342a to form a first antenna element arranged in the XY plane so as to transmit and receive signals primarily in the orthogonal z-axis direction. The second coil 338b is wound around the outer coil support surface 340b of the second coil support channel 342b over the first coil 338a to form a second antenna element in the XZ plane so as to transmit and receive signals primarily in the orthogonal y-axis direction. The third coil 338c is wound around the outer coil support surface 340c of the third coil support channel 342c over the first coil 338a and over the second coil 338b to form a third antenna element in the YZ plane so as to transmit and receive signals primarily in the orthogonal x-axis direction.

By providing three mutually orthogonal coils within the front body portion 310 of the probe 112 and three mutually orthogonal coils within the rear body portion 318, the likelihood of detecting a transponder at a given distance is improved. This is illustrated with reference to FIG. 21, which shows a sectional view of the second coil 338b disposed in the XZ plane and configured to transmit and receive signals primarily in the orthogonal y-axis direction, and a sectional view of the transponder 116d positioned proximate to the second coil. The efficiency of the coupling between the second coil 338b and the inductor or coil 254 of the transponder 116d is proportional to the presentation angle of the two coils relative to each other. Maximum coupling occurs when the two coils are in a parallel relationship (i.e., an angle $\Theta=0$ degrees). This condition results in maximum induced voltage in the transponder coil 254 and a maximum read range. As the transponder 116d is rotated with respect to the second coil 338b, the magnetic coupling is reduced by the cosine of the angle of rotation (i.e., a cosine $\Theta$ variation). Thus, when the two coils 338b and 254 are in a perpendicular relationship (i.e., angle $\Theta=90$ degrees), magnetic coupling is minimized (e.g., a "dead zone"). Under conditions of minimum coupling, it is less likely that the second coil 338b will be able to detect the transponder 116d.

By utilizing two sets of three mutually orthogonal coils 338a-338c, as opposed to a single planar coil, the ability to detect a transponder is significantly improved. For example, for each set of mutually orthogonal coils, it is possible to ensure that the angle $\Theta$ of rotation of the transponder coil 254 will always be less than 45 degrees with respect to at least one of the orthogonal coils 338a-338c. At an angle $\Theta$ of rotation of 45 degrees (i.e., "worst case" orientation), the magnetic coupling is approximately 71% of the maximum or optimum magnetic coupling (i.e., cosine 45 degrees=0.707). Thus, the use of three orthogonal coils 338a-338c ensures that the magnetic coupling between the transponder coil 254 and at least one of the coils 338a-338c of the probe 112 will always be at least 71% of the maximum coupling orientation. Accordingly, given the same transmit energy, transponders 116 may be detected at a greater distance using the two sets of three orthogonal coils 338a-338c as compared to using a single planar coil. Additionally or alternatively, the probe 112 may transmit signals at lower energy levels to achieve a similar read range as a single planar coil transmitting at a higher energy level.

In the illustrated implementation, the respective second support channels 342b of the first coil assembly 314 and the second coil assembly 316 are oriented to be coplanar in an XZ plane to transmit and receive signals primarily in the orthogonal y-axis direction. The respective first support channels 342a of the first coil assembly 314 and the second coil assembly 316 are oriented to be parallel and non-coplanar in an XY plane to transmit and receive signals primarily in the orthogonal z-axis direction. The respective third support channels 342c of the first coil assembly 314 and the second coil assembly 316 are oriented to be parallel and non-coplanar in a YZ plane to transmit and receive signals primarily in the orthogonal x-axis direction. In other implementation, the respective support channels of the first coil assembly 314 and the second coil assembly 322 may aligned differently with respect to each other.

Figure 4:
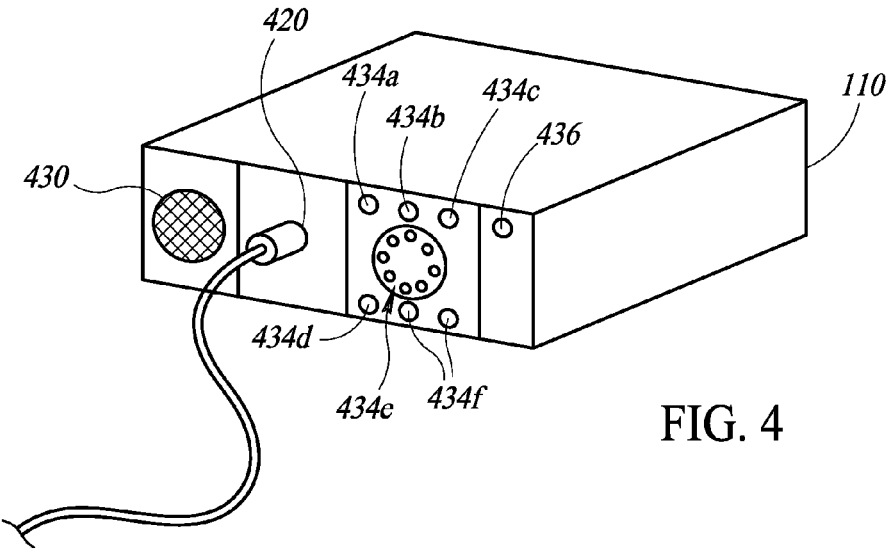
FIG. 4 is an isometric view of a controller of the interrogation and detection system, according to one illustrated implementation.

FIG. 4 shows the controller 110 according to one illustrated implementation. The controller 110 includes an input port 420 with an appropriate coupling member, for example a connector to allow an end of the coaxial cable 114 to be communicatively coupled to the controller 110. As noted above, some implementations may employ other communications pathways between the controller 110 and the coil assemblies 314 and 322, hence other types of coupling members or connectors may be employed. The controller 110 may also include a power switch (not illustrated in FIG. 4), for example, positioned on a back or rear of the controller 110. The controller 110 may further include a power cord (not shown) to couple the controller 110 to a suitable power supply. The power supply may, for example take the form of a standard wall outlet or any other power supply or source. The controller 110 may further include one or more user interface devices for providing information to a user. For example, the controller 110 may include one or more visual indicators, for instance one or more light emitting diodes (LEDs) 434a-434f and/or liquid crystal displays. Additionally, or alternatively, the controller 110 may include one or more speakers 430 or other transducers operable to produce sound or tactile sensations. The controller 110 forms a transmitter and receiver, or transceiver, to transmit interrogation signals and receive responses to those signals, as well as to receive electromagnetic signals which may be indicative of noise.

Figure 5:
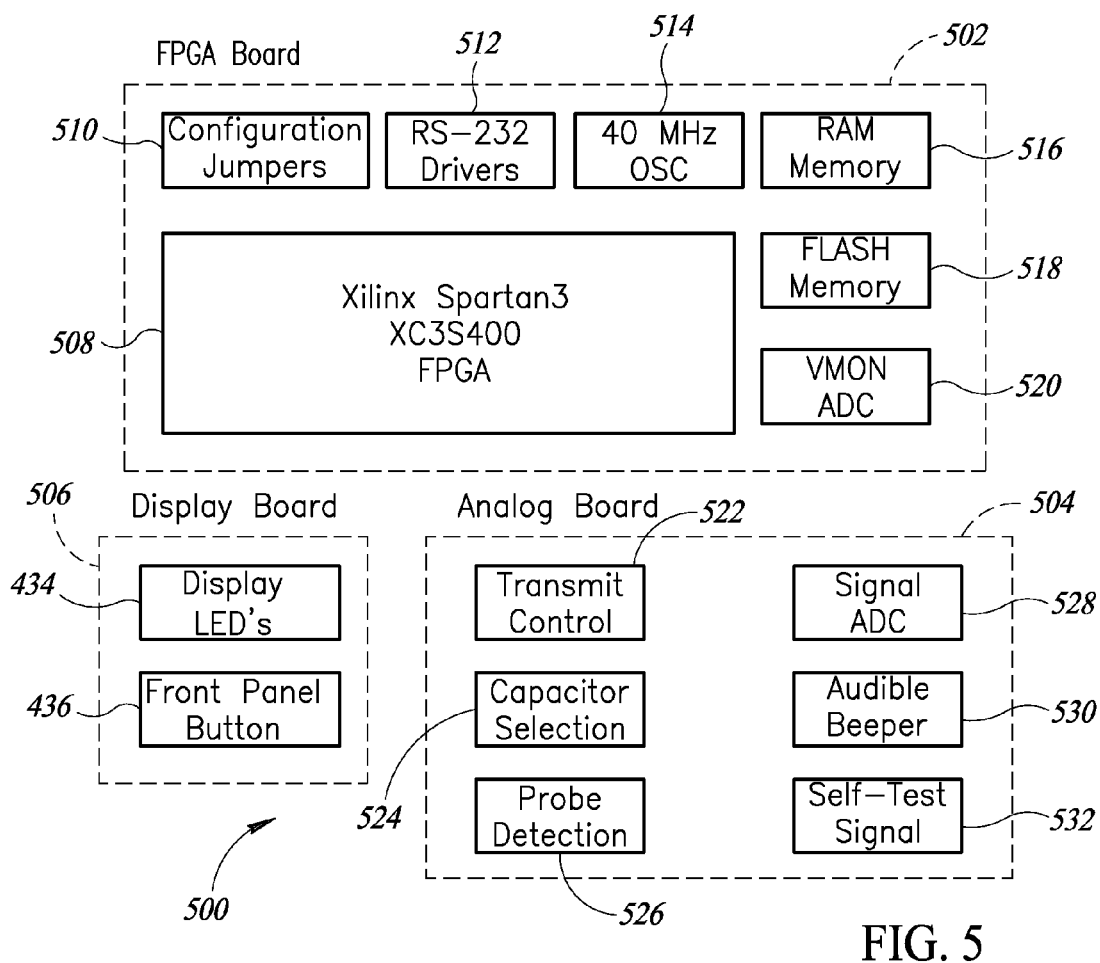
FIG. 5 is a schematic diagram of a control system of the interrogation and detection system, according to one illustrated implementation.

FIG. 5 shows a control system 500 of the interrogation and detection system 104, according to one illustrated implementation.

The control system 500 includes a field programmable gate array (FPGA) board 502, analog board 504 and display board 506, communicatively coupled to one another. The FPGA board includes an FPGA 508, configuration jumpers 510, RS-232 drivers 512, oscillator 514, random access memory (RAM) 516, flash memory 518, and voltage monitoring (VMON) analog-to-digital converter (ADC) 520. The FPGA 508 may take the form of a Xilinx Spartan3 FPGA, which runs FPGA and application software. As explained below, on power up, the FPGA reads the configuration information and application software program from the flash memory 518.

The configuration jumpers 510 are used to select the application software configuration.

The RS-232 drivers 512 are used to allow the application software to communicate using serial RS-232 data for factory test and diagnostics.

The oscillator 514 sets the clock frequency for the operation of the FPGA 508. The oscillator 514 may, for example, take the form of 40 MHz oscillator, although other frequencies are possible.

The RAM 516 is connected to the FPGA 508 and is available for use by the application software. The application software uses this memory space for storage of both the executable program and program data. The RAM 516 may, for example, have a capacity of 1 MB.

The flash memory 518 contains both the FPGA configuration data and the binary application program. On power up the FPGA 508 reads the flash memory to configure the FPGA 508 and to copy the application program binary data from the flash memory 518 to the RAM 516.

The voltage monitor ADC 520 is connected to the FPGA 508 and controlled by the application software to monitor a power supply and regulated voltage forms in controller electronics.

The analog board 504 includes transmit control circuits 522, capacitor selection circuits 524, probe detection circuit 526, signal ADC 528, audible beeper 430 and self-test signal 532.

The transmit control circuits 522 on the analog board 504 are controlled by signals from the FPGA 508 to generate a transmit waveform.

Optional capacitor selection circuits 524 on the analog board 504 are controlled by the signals from the FPGA 508 to tune the drive circuit to match an inductance of the antennas of the coil assemblies 314 and 322.

The probe detection circuit 526 detects when a probe 112 is connected to the controller 110. The output of the probe detection circuit 526 drives a signal denominated as the LOOP_LEVEL_OUT signal, which is an input to the FPGA 508.

The signal ADC 528 is used as a receiver to sample the signals received at the coil assemblies 314 and 322 from the transponders 116 (FIGS. 2A-2C). The signal ADC 528 may, for example, operate at a 1 MHz sample rate and may have 12-bits of resolution. The FPGA board 502 generates the timing and control signals for the signal ADC 528, which signals are denominated as ADC_CTRL, CS1, SCLK, and SD0.

The audible speaker or beeper 430 can be controlled by the FPGA 508 to emit sounds to indicate various states, modes or operating conditions to the medical provider 102 (FIGS. 1A-1B).

The FPGA 508 can cause the generation of the self-test signal 532 on the analog board 504 at the signal ADC 528. Self-testing may be performed at start up, and/or at other times, for example periodically or in response to the occurrence of certain conditions or exceptions.

The display board 506 includes user interface elements, for example a number of light emitting diodes (LEDs) 434. The FPGA board 502 can control the LEDs 434 on the display board 506. The display board 506 also includes a user selectable activation switch, denominated as front panel button 436. The front panel button 436 is connected to the display board 506 which allow the FPGA 508 to monitor when the front panel button 436 is activated (e.g., pressed).

Figure 6:
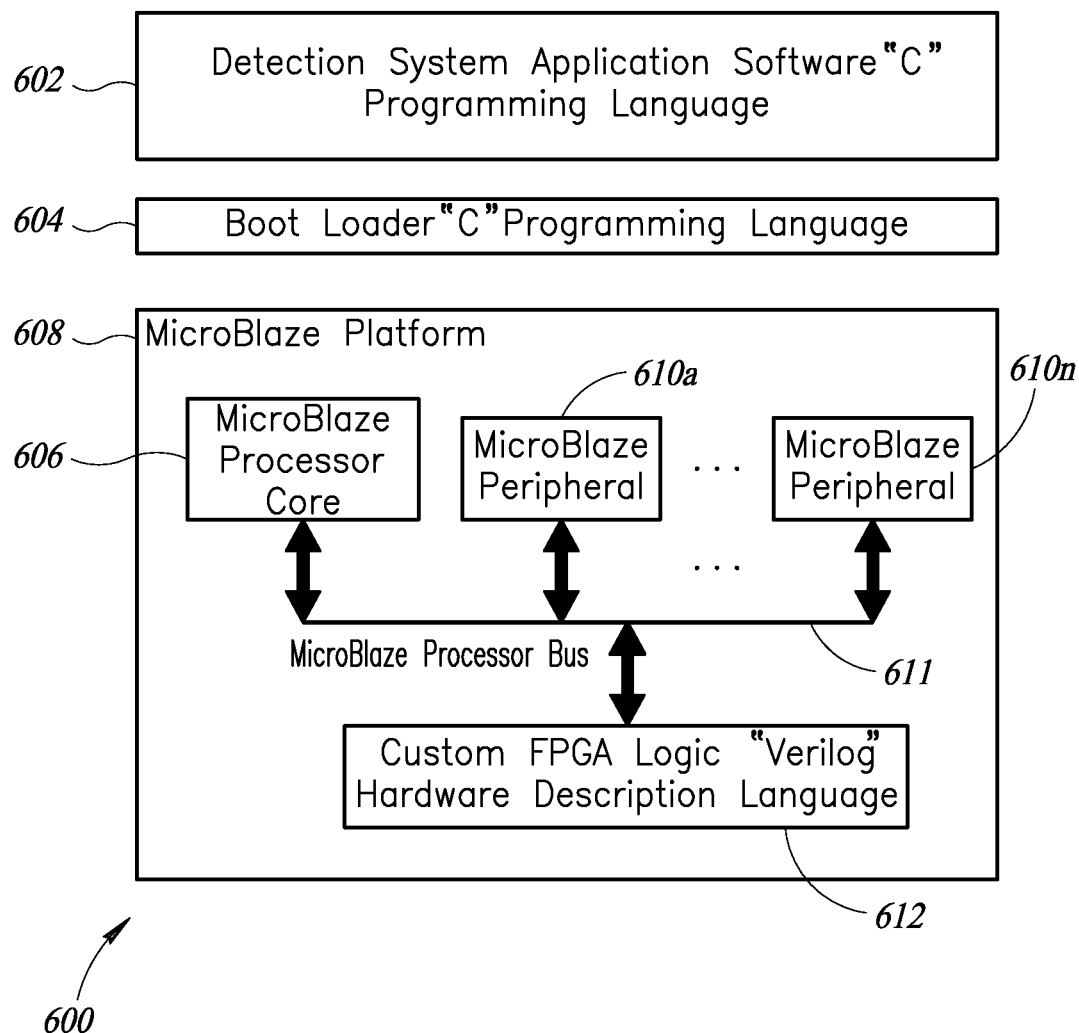
FIG. 6 is a schematic diagram of a software configuration of the interrogation and detection system, according to one illustrated implementation.

FIG. 6 shows a software configuration 600 of the interrogation and detection system 104, according to one illustrated implementation.

The software may include application software 602 that is responsible for operating the controller 110 (FIGS. 1A-1B and 4). The application software 602 controls the timing for generating transmit pulses, processes sampled data to detect transponders 116 (FIGS. 2A-2C), and indicates status to the user with the display LED's 434 (FIG. 5) on the display board 506 and/or via the audible speaker or beeper 130 on the analog board 504. The application software 602 is stored in the flash memory 518 (FIG. 5) and transferred into the RAM 516 by a boot loader 604.

The boot loader 604 is automatically loaded when the FPGA 508 is configured, and starts execution after a processor core 606 is reset. The boot loader 604 is responsible for transferring the application software 602 from the flash memory 518 to the external RAM 516.

The processor platform 608 is configured into the FPGA 508 (FIG. 5) on power up from the configuration information stored in the flash memory 518. The processor platform 608 implements a custom microprocessor with a processor core 606, peripherals 610a-610n, and custom logic 612.

The processor core 606 may take the form of a soft processor core supplied by XILINX under the name MICROBLAZE that implements a 32-bit processor including memory cashes and a floating point unit. A soft-core processor is one that is implemented by interconnected FPGA logic cells instead of by traditional processor logic. The processor core 606 is connected to the internal FPGA peripherals 610a-610n using a 32-bit processor bus 611 called the On-Chip Peripheral Bus. The XILINX supplied peripherals for the MICROBLAZE processor core 606 include external memory interfaces, timers, and general purpose I/O.

The custom logic 612 to create the transmit signals, sample the ADC 128, and accumulate the transponder return signals is designed as a peripheral to the processor core 606. The custom logic 612 is the part of the design of the FPGA 508.

In some implementations, a detection cycle that employs an approach that optimizes signal to noise ratio (SNR) by a receiver portion may be implemented. Such may, for example, advantageously increase range or increase sensitivity at a given range. One implementation is optimized based on having an overall detection cycle that performs well for transponders with resonant frequencies from approximately 136 kHz to approximately 154 kHz.

The application software 602 (FIG. 6) implements the detection cycle using transmission or interrogation in a frequency band centered around a center channel or frequency. The application software 602 sequences through a non-measurement portion (i.e., gap), and two distinct measurement portions, denominated as a noise detection portion and a signal measurement portion, each detection cycle. In at least one implementation, the detection cycle may, for example, be approximately 275 milliseconds, the gap portion may be approximately 10 milliseconds, the noise portion approximately 37 milliseconds and the signal measurement portion approximately 228 milliseconds.

During the noise detection portion, which may, for example be a first measurement portion of each detection cycle, ambient or background noise is measured or sampled, providing a value indicative of a level of ambient or background noise for the particular environment. The noise measurements or are taken or captured at a time sufficiently after excitement of the transponders 116 by the interrogation signal emitted by the transmitter such that the transponders 116 are substantially not resonating or responding to any previous excitation by interrogation signals. In particular, a number N of measurements or samples are taken during the noise detection or first measurement portion.

During the signal measurement portion which may, for example, take the form of the second measurement portion of each detection cycle, responses by transponders 116 are measured or sampled. The response measurements or samples are taken with the transmitter transmitting or at a time sufficiently close to excitement of the transponders 116 by the interrogation signal emitted by the transmitter such that the transponders 116 are still substantially resonating or responding to the interrogation signal. In particular, a number M of measurements or samples are taken during the interrogation or second measurement portion.

While the signal measurement portion may be one contiguous or continuous portion, in some implementations the signal measurement portion may take the form of two or more separate portions or intervals. Each of the portions may employ the same transmit frequency band, for example centered around 145 kHz. Other center channels or frequencies may for example be 136 kHz, 139 kHz, 142 kHz, 145 kHz, 148 kHz, 151 kHz and/or 154 kHz, or any other frequency suitable for exciting the transponder to resonate. Some implementations may employ frequency hopping, for example transmitting a different center channel or frequency for each of a plurality of signal measurement portions of each detection cycle. Such is discussed further in U.S. provisional patent application Ser. No. 60/892,208, filed Feb. 28, 2007 and U.S. non-provisional application Ser. No. 11/743,104, filed May 1, 2007.

The gap portion may provide time for the response of the transponders 116 to the interrogation signal to decay sufficiently to allow measurement of noise.

Some implementations may arrange the gap, the noise detection portion and/or the signal measurement portion, or parts thereof, in a different order.

In one implementation, the time to accumulate the noise sample or value indicative of a noise level may, for example, be approximately 37 milliseconds, and the time to accumulate the transponder signal measurement approximately 228 milliseconds. Along with a gap of approximately 10 milliseconds between the signal and noise portions, the time for a single detection cycle would be approximately 275 milliseconds. As noted above, the transmitter is OFF during the noise measurement portion of each detection cycle to allow the receiver to measure ambient noise, and the signal detection portion is taken with the transmitter transmitting a wideband interrogation signal about the particular center channel or frequency.

The noise samples collected by the receiver may be accumulated and a highest one or more of multiple samples or measurements over one or more detection cycles selected or used to prevent unwarranted fluctuations. The response signals from the transponder 116 may be accumulated and/or averaged or integrated over one detection cycle or over multiple detection cycles.

The number N of noise measurements or samples and/or the number M of response signal measurements or samples may be selected to achieve a desired ratio of N to M, in order to achieve or maintain a desired signal to noise ratio. For example, obtaining 200 noise measurements or samples and 800 response measurements or samples each detection cycle results in an SNR of approximately 2 (e.g., the square root of 800 divided by 200). While an SNR as low as 1.1:1 may be sufficient in some implementations, an SNR approaching 2:1 ensures sufficient differentiation to eliminate or reduce the possibility of false positives to an acceptable level for the particular applications envisioned herein. Any known hardware and software accumulators, summers, integrators and/or other hardware or software may be suitable.

The accumulated or integrated received signal may be matched filtered with both in-phase and quadrature reference signals to determine the signal magnitude. The received receive signal is matched filtered with a plurality of reference signals, for example with the seven reference signals, for instance as shown in Table 1 below. Some implementations may employ matched filtering before accumulating or integrating the received signal.

TABLE 1

| Match Frequency |
| --- |
| 136 kHz |
| 139 kHz |
| 142 kHz |
| 145 kHz |
| 148 kHz |
| 151 kHz |
| 154 kHz |

The maximum value for the matched filters (e.g., seven matched filters) with active transmit may be compared with an adjusted detection threshold. If the maximum value is greater than the detection threshold, then a response signal from a transponder 116 may be considered as having been detected, and appropriate action is taken, such as discussed below with reference to FIG. 7. Alternatively or additionally, the interrogation and detection system may employ a fast Fourier transform approach in lieu of matched filtering.

The noise filtering processes the measured or sampled noise values for each detection cycle to determine a stable noise floor value. The output of the noise filter may, for example, be the maximum of either the current noise measurement or a decayed value of the previous noise floor.

The output of the noise filter may be an estimate of the current noise floor level after selecting the highest of a plurality (e.g., 6) of noise measurements or samples. The filtered noise floor may advantageously include samples collected, captured or measured both before and after a given signal sample is collected, captured or measured. Thus, for any sample of a given detection cycle the noise floor may include noise samples from the given detection cycle, as well as a next successive detection cycle. The filtered noise floor may additionally, or alternatively, include noise samples from one or more successively preceding detection cycles, as well as one or more successfully succeeding detection cycles.

Figure 7:
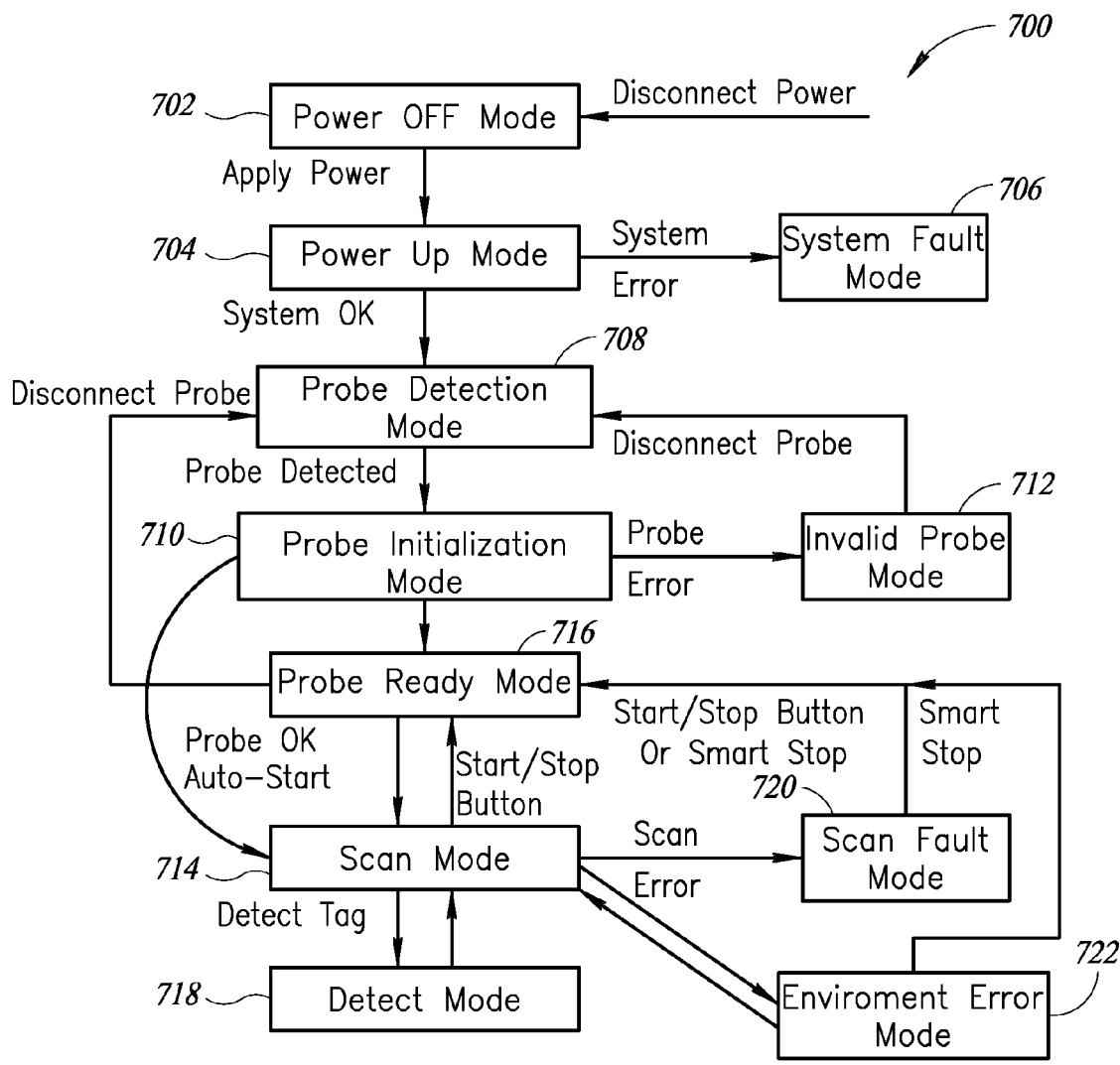
FIG. 7 is a flow diagram of a method of operating an interrogation and control system, according to one illustrated implementation.

FIG. 7 shows a method 700 of operating the interrogation and detection system 104 according to one illustrated implementation.

In response to detecting a disconnect of power, the interrogation and detection system 104 enters a Power OFF mode at 702. For example, the Power OFF mode 702 may be entered when the controller 110 (FIGS. 1A-1B and 4) is unplugged or when the power switch on the controller 110 is turned OFF. In the Power OFF mode 702, the Power LED 434a and other front panel LEDs 434 will be turned OFF (non-emitting). The software 700 is inoperative in the Power OFF mode 702.

In response to detecting an application of power, the interrogation and detection system 104 enters a Power-Up mode 704. The Power UP mode 704 may, for example, in response to the application of power to the controller 110 and turning ON the switch on the back of the controller. In the Power-Up mode 704, a Power LED 434a may be turned ON or illuminated, and may remain ON or illuminated as long as the power is applied and the switch is in the ON state. In response to entering the Power UP mode 704, the software 700 will perform software initialization, built in tests, and an audio/visual test.

If a fault is detected, the software 700 progresses to a System Fault Mode 706. If no faults are detected, the software 700 may turn a System Ready LED green, and enter a Probe Detection Mode 708.

In the System Fault Mode 706, the software 700 may cause an indication of the detection of a system fault by blinking a System Ready LED 434b yellow, and/or issuing a sequence of rapid beeps or other sounds. The corrective action for the System Fault Mode 706 is to cycle power to reinitiate the Power Up mode 704. Continued failure indicates a failed controller 110.

In the Probe Detection Mode 708, the software 700 checks for a probe 112 connected to the controller 110. The Probe Detection Mode 708 may be indicated by turning the System Ready LED 434b green and turning the Probe Ready LED 434c OFF. If no probe 112 is detected, the software 700 remains in the Probe Detection Mode. If a probe 112 is detected, the software 700 progresses to the Probe Initialization Mode 710.

At the start of the Probe Initialization Mode 710, after the detection of a probe 112, the software 700 may turn the Probe Ready LED 434c yellow and check for the presence of a fuse in the probe 112. If a fuse is found, the software 700 may attempt to blow the fuse and verify that the fuse was correctly blown. After the fuse is blown the software 700 may verify that probe 112 is operating within tolerances. The software 700 may indicate that the probe 112 is ready by turning the Probe Ready LED 434c green. The software 700 may also start a timer which will allow the probe 112 to be disconnected and reconnected to the controller for a period of time (e.g., 5 hours) after the fuse is blown.

The controller 110 may determine the adjustments or fine tuning to be made about the center frequencies or channels during Probe Initialization Mode 710. In particular, the controller 110 may determine the particular frequency in each of the frequency bands that elicits the response with the highest voltage. The controller may determine such by varying the capacitance of the LC circuit using the switched capacitors C33-C36 during the Probe Initialization Mode 710. The particular combination of switched capacitors C33-C36 which achieved the response with the highest voltage may then be automatically employed during a Scan Mode 714 (discussed below) to adjust or fine tune about the center frequency or channel in each broad band of transmission. Other approaches to determining the fine tuning may be employed.

If the software 700 does not successfully complete the Probe Initialization Mode 710, the software 700 enters an Invalid Probe Mode 712. If the software 700 successfully completes the Probe Initialization Mode 710, the software 700 progresses to the Scan Mode 714 to automatically start scanning.

In the Invalid Probe Mode 712, the software 700 may blink the Probe Ready LED 434c yellow and issues a slow beep pattern.

The Invalid Probe Mode may be entered in response to any of the following conditions:

The probe 112 connected to the controller 110 is out of tolerance.

The controller 110 is unable to blow the fuse in the probe 112.

The probe 112 does not have a fuse and more than the set time period has past (e.g., 5 hours) since a fuse was blown.

The probe 112 does not have a fuse and the controller 110 has been restarted.

The probe 112 has been connected to the controller for more than the set time period (e.g., 5 hours).

The probe 112 is detuned due to close proximity to metal.

The corrective action for the Invalid Probe Mode 712 is to remove the invalid probe 112 and attach a new probe 112 to the controller 110 that contains a fuse or to reconnect the probe 112 while holding it in the air at least 2 feet away from large metallic objects.

The software 700 enters the Scan Mode 714 when the probe 112 is ready and the operator presses a Start/Stop button. The software 700 may issue a short three beep pattern via the speaker or beeper 130 when entering the Scan Mode 714 to identify the entry to the user.

In the Scan Mode 714, the software 700 may continuously or periodically perform the following functions.

Look for response signals from transponders 116
Monitor the noise level
Insure the probe 112 is connected and operating correctly
Blink the LED's in a circular pattern
When the operator or user pushes the Start/Stop button or the a scan maximum time interval (e.g., 4 minute) has been reached, the software 700 may issue a short three beep pattern and return to the Probe Ready Mode 716.

When an appropriate response signal from a transponder 116 is detected while in Scan Mode 714, the software 700 may turn ON an amber DETECT LEDs 434*d* and/or provide an audible alarm. The alarm may, for example, beep a continuous solid tone as long as the transponder is detected, with a minimum of beep duration of, for instance 0.5 second.

If the software 700 detects the probe 112 is disconnected while in the Scan Mode 714, the software 700 enters the Scan Fault Mode 720. In the Scan Fault Mode 720, the software 700 may issue a sequence of rapid beeps and blink ON and OFF the amber DETECT LEDs 434*d*. The Scan Fault Mode 720 can be cleared by pushing the Start/Stop button. The software 700 will automatically clear the Scan Fault Mode 720 after 10 beeps.

While in the Scan Mode 714, if excess noise or loss of transmit signal is detected, the software 700 will progress to the Environment Error Mode 722. In the Environment Error Mode 722, the software 700 may issue or produce an appropriate indication. For example, the software 700 may cause the production of a sequence of slow beeps and the blinking ON and OFF the green circle LEDs 434*e*. The corrective action for the Environment Error Mode 722 is to reposition the probe 112 away from large metal objects or sources of electrical interference. The software 700 will automatically stop the scan if the environment error condition lasts for more than a set time or number of beeps (e.g., 5 beeps).

FIG. 8 shows a method 800 of operating an interrogation and detection system, according to one illustrated implementation. The method 800 may be implemented by any of the interrogation and detection system implementations discussed above.

During each of a plurality of detection cycles, the interrogation and detection system performs a number of acts 802-812. At 802, the interrogation and detection system receives electromagnetic signals, for example unmodulated electromagnetic signals, during a noise detection portion of the detection cycle. The below descriptions will be presented in terms of unmodulated electromagnetic signals due to the unique technical advantages realized by a system that employs simple resonant transponders without any on-board memory or storage, and from which information cannot be read from or written to. However, some implementations may employ readable and/or writable transponders, for instance radio frequency identification (RFID) transponders or tags, which respond with a modulated electromagnetic signal that encodes information in the modulation. The various techniques described herein are applicable to such transponders and modulated electromagnetic signals.

At 804, the interrogation and detection system determines a noise value indicative of a noise level that corresponds to a highest one of a number N of samples or measurements of the unmodulated electromagnetic signals received during the noise detection portion of the detection cycle, where the number N is greater than one. At 806, the interrogation and detection system adjusts a signal detection threshold based at least in part on the determined noise value of at least one of the detection cycles.

At 808, the interrogation and detection system emits at least one electromagnetic interrogation signal during a transmit portion of the detection cycle. At 810, the interrogation and detection system receives unmodulated electromagnetic signals during a receive response portion of the detection cycle that follows the transmit portion of the detection cycle.

At 812, the interrogation and detection system determines the presence or absence of a transponder based at least in part on a number M of samples or measurements of the unmodulated electromagnetic signals received during the detection cycle and the adjusted signal detection threshold, where the number M is greater than one. A ratio of N:M may be at least equal to 4. N may be equal to about 200 and M may be equal to about 800, for example.

The interrogation and detection system may determine a noise value indicative of a noise level based at least in part on the unmodulated electromagnetic signals received during the noise detection portion of the detection cycle by setting the noise value based on the highest one of six samples or measurements of the unmodulated electromagnetic signal received during the noise detection portion of the detection cycle.

The interrogation and detection system may adjust the signal detection threshold by adjusting the signal detection threshold based at least in part on a first number of determined noise values indicative of a noise level during at least one noise detection portion that occurred before the receive response portion of a first one of the detection cycles and a second number of determined noise values indicative of a noise level during at least one noise detection portion that occurred after the receive response portion of the first one of the detection cycles.

The interrogation and detection system may adjust the signal detection threshold based at least in part on the determined noise value of at least one of the detection cycles by adjusting the signal detection threshold to be approximately twice an average of at least one of the first and the second number of determined noise values.

The interrogation and detection system may adjust the signal detection threshold based at least in part on the determined noise value of at least one of the detection cycles by adjusting the signal detection threshold to be approximately twice a greatest one of at least one of the first and the second number of determined noise values.

The interrogation and detection system may determine the presence or absence of a transponder by comparing a maximum value of a plurality of matched filter outputs with the adjusted signal threshold.

The interrogation and detection system may adjust the signal detection threshold based at least in part on the determined noise value of at least one of the detection cycles by adjusting the signal detection threshold to be approximately twice the determined noise value.

The interrogation and detection system may adjust the signal detection threshold based at least in part on the determined noise value of at least one of the detection cycles includes adjusting the signal detection threshold to be the larger of approximately twice the determined noise value or a defined threshold value. The defined threshold value may for example be approximately 0.5 mV.

In some implementations, the interrogation and detection system determines if an output of at least one matched filter during the noise detection portion of the detection cycle exceeds a noise fault threshold indicative of a noise fault.

In some implementations, the interrogation and detection system determines if the output of the at least one matched filter during the noise detection portion of the detection cycle exceeds the noise fault threshold for a defined period of time. The interrogation and detection system may terminate the detection cycle in response to the output of the at least one matched filter exceeding the noise fault threshold for the defined period of time.

The interrogation and detection system may convert the received signal(s) from the time domain to the frequency domain spectrum. The interrogation and detection system may, for example, perform a Fourier transform, for instance a fast Fourier transform such as a 256 point fast Fourier transform. Suitable algorithms and/or sets of software code for performing such are available or can be written.

The interrogation and detection system may search the frequency domain spectrum to determine the object with the strongest resonance in a defined frequency band. For example, the interrogation and detection system may search the frequency domain spectrum from about 120 kHz to about 175 kHz. An amplitude of the resonant object may be computed as the sum of the resonant power plus and minus 2 fast Fourier transform bins from the peak resonance frequency. This approach may provide a more accurate measurement of power than simply using the peak value. The frequency of the resonant object may be computed using an interpolation approach. This approach may provide a more accurate determination of resonant frequency than simply using the fast Fourier bin number.

The interrogation and detection system may determine the presence or absence of a transponder based at least in part on a frequency of the unmodulated electromagnetic signals received during the detection cycle being within a defined frequency range. The defined frequency range may extend from about 137 kHz to about 160 kHz, for example.

The interrogation and detection system may determine a Q value (i.e., Quality factor) of the resonant object from a signal decay slope for the received unmodulated electromagnetic signal(s) returned by the resonant object. The interrogation and detection system may, for example, use multiple windows, for instance five (5) window positions may provide suitable results.

The interrogation and detection system may determine the presence or absence of a transponder based at least in part on a Q value of the unmodulated electromagnetic signal(s) received during the detection cycle. The interrogation and detection system may preferably employ the Q value determination in conjunction with determination based on the frequency and on the determination based on the adjusted signal detection threshold.

In some implementations, the interrogation and detection system determines the presence or absence of a transponder is based at least in part on a Q value of the unmodulated electromagnetic signals received during the detection cycle being at least equal to a threshold Q value. The threshold Q value may be 35, for example. The interrogation and detection system may preferably employ the Q value determination in conjunction with determination based on the frequency and on the determination based on the adjusted signal detection threshold.

Consequently, tag detection may advantageously be based on the received unmodulated electromagnetic signal(s) satisfying all three conditions: 1) measured amplitude is above a threshold, which may be an adjustable threshold, 2) measured frequency is between a lower limit and an upper limit, and 3) measured Q value is above a minimum Q threshold. Interference, for example from RFID tags or EKG cables, are rejected when any of the following three conditions are satisfied: a) measured frequency is below the lower frequency limit, b) measured frequency is above the upper frequency limit, or c) measured Q value is below the threshold Q value. Such may provide significantly superior results over previous approaches, preventing false positives which could otherwise cause a patient to remain open for longer period of time during surgery and tie up hospital personnel and resources.

FIG. 9 shows a graph 900 of a simulated transponder response signal 902 and a noise signal 904. The inexpensive transponders usable with implementations disclosed herein typically have a relatively large variation in the frequency of signals they emit, making it difficult to accurately detect the signals returned by the transponders. This may be particularly difficult in some environments which are noisy with respect to the particular resonant frequencies of the transponders. For example, operating rooms may have one or more electronic medical devices that emit RF noise that is harmonically synchronous with the response signals received from the transponders. Consequently, even though the responses signals may be received synchronously with the transmitted interrogation signals, noise that is harmonically synchronous with the response signals may still be high if the peaks of the noise occur at times the interrogation and detection system is expecting to see response signals from a transponder.

The transponder response signal 902 may, for example, be a nominal periodic signal centered around a particular frequency (e.g., 136 kHz, 145 kHz, 154 kHz, etc.). The noise signal 904 may be emitted from an electronic medical device located proximate to the interrogation and detection system 104 (FIGS. 1A-1B), for example. In this illustration, the amplitude of the noise signal 904 is much greater than the amplitude of the transponder response signal 902. As shown, at a point 906 in time the noise signal 904 is at a peak and the transponder response signal 902 is near its zero crossing. If the interrogation and detection system 104 were to obtain a sample at the point 906 the noise signal 904 would mask the transponder response signal 902. Conversely, at points 908 and 910, the noise signal 904 is at or close to its zero crossing while the transponder response signal 902 is near its peak. If the interrogation and detection system 104 can sample the simulated response signal 902 at times when the noise signal 904 is at its zero crossing or at a low amplitude, it is possible for the interrogation and detection system to detect a transponder through the noise signal 904 (or "noise floor") that is many times greater than the transponder response signal 902.

To accomplish this, in some implementations the scanning process for each antenna or coil is broken down into $N_{SS}$ subsample scan cycles for each transmit frequency. Each of the subsample scan cycles includes one or more interrogation cycles. As discussed in further detail below, each of the interrogation cycles in a particular one of the $N_{SS}$ subsample scan cycles is shifted forward in time a fraction of the period (T) of a nominal expected transponder response signal 902 to provide $N_{SS}$ opportunities to avoid harmonic noise being synchronous in time with the desired transponder response signal.

FIG. 10 illustrates timing for a single interrogation cycle 1010 in an implementation that utilizes the aforementioned subsample scan cycles, according to one illustrated implementation. Each of the $N_{SS}$ subsample scan cycles may include one or more interrogation cycles 1010, as discussed below. The custom logic in the FPGA 508 (FIG. 5) generates the timing and control signals for each interrogation cycle 1010. During a transmit portion 1010a of the interrogation cycle 1010, the logic of the FPGA 508 drives transistor control lines to generate the transmit signal. The FPGA logic controls the frequency of the transmit signal. In some implementations, the transmit portion 1010a has a duration of 200 microseconds (μs), for example. During a dump portion 1010b of the interrogation cycle 1010, the logic of the FPGA 508 drives a gate of a dump TRIAC to quickly drain the transmit energy from the antenna to allow detection of the response signal from the transponder 116, if any. In some implementations, the dump portion 1010b has a duration of 10 μs, for example. A recovery portion 1010c of the interrogation cycle 1010 allows receive filters and amplifiers to recover from the transmitted signal before detecting the response signal from the transponder 116, if any. The recovery portion 1010c may have a duration of 100 µs, for example. During a receive response portion 1010d of the interrogation cycle 1010, the FPGA 508 controls the signal ADC 128 to sample the response signal from the transponder 116, if any. The signal ADC 128 may, for example, sample at a 1 MHz sample rate (i.e., 1 sample per µs) with a 12-bit resolution. In some implementations, the receive response portion 1010d has a duration of 512 µs, such that the signal ADC 128 obtains 512 measurements at the 1 MHz sample rate during the receive response portion 1010d. A skip portion 1010e of the interrogation cycle 1010 may be provided during which time measurements from the signal ADC 128 are skipped or ignored. In some implementations, the skip portion 1010e has a duration of 40 µs. The timing of the receive response portion 1010d may be such that the transponder response signal is synchronous to the transmit time.

A subsample scan cycle delay period 1010f of the interrogation cycle 1010 has a unique duration for interrogation cycles associated with a particular one of the $N_{SS}$ subsample scan cycles. Interrogation cycles associated with different ones of the $N_{SS}$ subsample scan cycles may have subsample scan cycle delay periods 1010f having differing durations. In some implementations, the subsample scan cycle delay period 1010f associated with respective ones of the $N_{SS}$ subsample scan cycles may be approximately a fraction of the period (T) of the expected transponder response signal 902 (FIG. 9). For example, the subsample scan cycle delay periods 1010f for interrogation cycles associated with subsample scan cycles 1 to $N_{SS}$ may be approximately:

$(0/N_{SS})*T$ for interrogation cycles of subsample scan cycle 1;

$(1/N_{SS})*T$ for interrogation cycles of subsample scan cycle 2;

$(2/N_{SS})*T$ for interrogation cycles of subsample scan cycle 3;

. . .

$((N_{SS}-1)/N_{SS})*T$ for interrogation cycles of subsample scan cycle $N_{SS}$.

Thus, the period (T) of the expected transponder response signal is divided into $N_{SS}$ start times, with each of the $N_{SS}$ subsample scan cycles being associated with a different one of the start times.

FIG. 11A is a timing diagram 1100 illustrating an overall instrument scan cycle 1102, according to one illustrated implementation. The instrument scan cycle 1102 may be implemented by the interrogation and detection system 104 to scan for one or more resonant transponders. The instrument scan cycle 1102 may have a duration between a start time and a stop time that is less than about 20 seconds (e.g., two seconds, five seconds, 10 seconds, 15 seconds, etc.) so that the user operating the interrogation and detection system 104 does not need to wait an extended period of time to perform a scan operation. The instrument scan cycle 1102 may be executed one or more times during the Scan Mode of the interrogation and detection system 104. As discussed in further detail below, each instrument scan cycle 1102 may include one or more coil scan cycles, which may include one or more frequency specific sample cycles, which may include one or more subsample scan cycles, which may include one or more interrogation cycles.

The instrument scan cycle 1102 includes a number $N_{COILS}$ of coil scan cycles 1104, one coil scan cycle for each of $N_{COILS}$ present in the interrogation and detection system 104. For example, the detection system 104 may include three antenna coils ($N_{COILS}$=3), mutually orthogonal to each other, such that each instrument scan cycle 1102 includes three coil scan cycles 1104. In some implementations the detection system 104 may include six antenna coils ($N_{COILS}$=6), or a greater or fewer number of antenna coils. In some implementations, the detection system 104 includes a single coil ($N_{COILS}$=1), such that only a single coil scan cycle 1104 is performed during each instrument scan cycle 1102.

FIG. 11B is a timing diagram 1106 illustrating a cycle for one of the coil scan cycles 1104 shown in FIG. 11A, according to one illustrated implementation. The coil scan cycle 1104 includes a number $N_{FREQ}$ of frequency specific sample cycles 1108, one for each transmit frequency to be used by the interrogation and detection system 104. The number $N_{FREQ}$ of frequency specific sample cycles 1108 may be any suitable value, such as one, two, five, eight, etc. For example, in some implementations the interrogation and detection system 104 may transmit interrogation signals at 139 kHz, 145 kHz, and 154 kHz during frequency specific sample cycle 1, frequency specific sample cycle 2, and frequency specific sample cycle 3, respectively. In some implementations, the interrogation and detection system 104 may transmit at a single frequency, such that only a single frequency specific sample cycle 1108 is performed during each coil scan cycle 1104.

FIG. 11C is a timing diagram 1110 illustrating a cycle for one of the frequency specific sample cycle 1108, according to one illustrated implementation. The frequency specific sample cycle 1108 includes a number $N_{SS}$ of subsample scan cycles 1112, one for each subsample to be collected by the interrogation and detection system 104. As used herein, a subsample may refer to measurements obtained during a subsample scan cycle. As discussed above, the number $N_{SS}$ of subsample scan cycles 1112 in each frequency specific sample cycle may be any suitable value, such as two, five, 10, 15, etc. As discussed above, each of the $N_{SS}$ subsample scan cycles has a unique subsample scan cycle delay period associated therewith. The subsample scan cycle delay periods for each of the $N_{SS}$ subsample scan cycles are applied during respective interrogation cycles associated with the respective subsample scan cycles.

FIG. 11D is a timing diagram 1114 illustrating one cycle of one of the subsample scan cycles 1112, according to one illustrated implementation. The subsample scan cycle 1112 includes a number $N_I$ of interrogation cycles 1010 (FIG. 10). As discussed below with reference to the example shown in FIG. 12, each of the $N_I$ interrogation cycles 1010 has a subsample scan cycle delay period 1010f associated with one of the particular subsample scan cycles 1112. In other words, interrogation cycles 1 to $N_I$ for one of the subsample scan cycles 1112 all have the same subsample scan cycle delay period 1010f. The number of interrogation cycles ($N_I$) per subsample scan cycle 1112 may be any suitable value, such as 10, 250, 500, or 1000 interrogation cycles per subsample scan cycle.

FIG. 12 illustrates a timing diagram 1200 for performing $N_{SS}$ subsample scan cycles 1202 (labeled subsample scan cycles 1-7) to obtain $N_{SS}$ subsamples, where $N_{SS}$ equals seven in this illustrated example. In this implementation, each of the subsample scan cycles 1-7 include 250 interrogation cycles 1010 (FIG. 10). Each of the interrogation cycles is designated as $I_{X-Y}$, where X is the subsample scan cycle with which the interrogation cycle is associated and Y is the number of the interrogation cycle within the subsample scan cycle. For example, $I_{2-3}$ represents the third interrogation cycle 1010 in subsample scan cycle 2. During a particular frequency specific sample cycle 1108 (FIG. 11) of a coil scan cycle 1104, the interrogation and detection system 104 performs subsample scan cycles 1-7 using a particular antenna coil (e.g., coil 338a of FIG. 3D) by sequentially executing interrogation cycles $I_{1-1}$ to $I_{1-250}$, $I_{2-1}$ to $I_{2-250}$, $I_{3-1}$ to $I_{3-250}$, $I_{4-1}$ to $I_{4-250}$, $I_{5-1}$ to $I_{5-250}$, $I_{6-1}$ to $I_{6-250}$, and $I_{7-1}$ to $I_{7-250}$, for a total of 1750 interrogation cycles, in this implementation. Table 2 below shows the approximate subsample scan cycle delay periods 1010f for interrogation cycles 1010 within each of the subsample scan cycles 1-7.

TABLE 2

| Subsample Scan Cycle | Subsample Scan Cycle Delay Period for Interrogation Cycles in Subsample Scan Cycle | Subsample Scan Cycle Delay Period: Response Signal at 145 kHz (T = 6.9 μs) |
| --- | --- | --- |
| 1 | (0/7) * T | 0 μs |
| 2 | (1/7) * T | ~1 μs |
| 3 | (2/7) * T | ~2 μs |
| 4 | (3/7) * T | ~3 μs |
| 5 | (4/7) * T | ~4 μs |
| 6 | (5/7) * T | ~5 μs |
| 7 | (6/7) * T | ~6 μs |

In the illustrated implementation, the subsample scan cycle delay periods 1010f are evenly spaced across the duration of the period (T) of the expected transponder response signal. For example, for a transponder response signal expected to have a center frequency of about 145 kHz, the period T is approximately 6.9 μs. Accordingly, interrogation cycles of a next successive subsample scan cycle has a subsample scan cycle delay period 1010f that is about 1/7 of the transponder response signal period T greater than interrogation cycles of a previous successive subsample scan cycle. As an example, the subsample scan cycle delay period 1010f for interrogation cycles $I_{4-1}$ to $I_{4-250}$ of subsample scan cycle 4 is three (3) μs and the subsample scan cycle delay period 1010f for interrogation cycles $I_{5-1}$ to $I_{5-250}$ of subsample scan cycle 5 is four (4) μs. By utilizing seven different subsample scan cycle delay periods 1010f spread across the duration of the period T of the expected transponder response signal, the probability of a sampling at a time of low harmonically synchronous noise and high transponder response signal is increased. In some implementations, more or less than seven subsample scan cycles may be used.

In some implementations, the subsample scan cycle delay periods 1010f of the interrogation cycles may be different fractions of the period (T) of the expected transponder response signal, offset by one or more periods T. For example, in some implementations with four subsample scan cycles, interrogation cycles of a subsample scan cycle 1 may have a subsample scan cycle delay period of T (i.e., (0/4)*T+T), such that the subsample scan cycle delay period is offset by one period T relative to the example provided in Table 2. Similarly, interrogation cycles of a subsample scan cycle 2 may have a subsample scan cycle delay period of (5/4)*T (i.e., (1/4)*T+T=(5/4)*T), interrogation cycles of a subsample scan cycle 3 may have a subsample scan cycle delay period of (6/4)*T (i.e., (2/4)*T+T=(6/4)*T), and interrogation cycles of a subsample scan cycle 4 may have a subsample scan cycle delay period of (7/4)*T (i.e., (3/4)*T+T=(7/4)*T). Importantly, the subsample scan cycle delay periods for the interrogation cycles in respective subsample scan cycles are different fractions of the expected transponder response signal. Other values for the subsample scan cycle delay periods may be used to obtain samples at different start times within the period T of the expected transponder response signal.

FIG. 13 shows a method 1300 of operating an interrogation and detection system to implement a coil scan cycle 1104 (FIGS. 11A-11D), according to one illustrated implementation. The method 1300 may be implemented by any of the interrogation and detection system implementations discussed above. The method 1300 may be used to collect subsamples using the subsample scan cycles including the interrogation cycles 1010 illustrated in FIGS. 10 and 12 for a single antenna coil. The method 1300 may be repeated for interrogation and detection systems utilizing a plurality of antenna coils (e.g., two sets of three mutually orthogonal antenna coils).

The method starts at 1302. The method 1300 may, for example, start when an interrogation and detection system enters the Scan Mode 714 (FIG. 7). At 1304, the interrogation and detection system initializes a control variable FREQUENCY_COUNT that may be used for comparison with a number of frequency bands to be used in the coil scan cycle (i.e., the number of frequency specific sample cycles 1108). In some implementations, more than one frequency band may be used during the coil scan cycle. For example, a first interrogation signal may be centered around 139 kHz, a second interrogation signal may be centered around 145 kHz, and a third interrogation signal may be centered around 154 kHz, for a total of three frequency specific sample cycles. Other center channels or frequencies may for example be 136 kHz, 142 kHz, 148 kHz, and or 151 kHz, or any other frequency suitable for exciting the transponder to resonate.

At 1306, the interrogation and detection system initializes a control variable SUBSAMPLE_COUNT. This control variable may be used during the method 1300 for comparison with a number of subsample scan cycles $N_{SS}$ to be executed by the interrogation and detection system. In the example shown in FIG. 12, the number of subsample scan cycles $N_{SS}$ is seven, but more or less subsample scan cycles may be used depending on how many divisions or start times in the period T of the expected transponder response signal are to be used. If $N_{SS}$ is relatively small, the probability of sampling at a time of low harmonically synchronous noise is reduced since the number of opportunities is reduced. If $N_{SS}$ is relatively large, the probability of sampling at a time of low harmonically synchronous noise is increased, but a tradeoff is that the total time for the coil scan cycle 1104 may also be increased.

At 1308, the interrogation and detection system initializes a control variable INTERROGATION_COUNT. This control variable may be used during the method 1300 for comparison with the number $N_I$ of interrogation cycles 1010 in each subsample scan cycle. In the example of FIG. 12, each subsample scan cycle includes 250 interrogation cycles 1010. More or less interrogation cycles per subsample scan cycle may be used.

Figure 11:
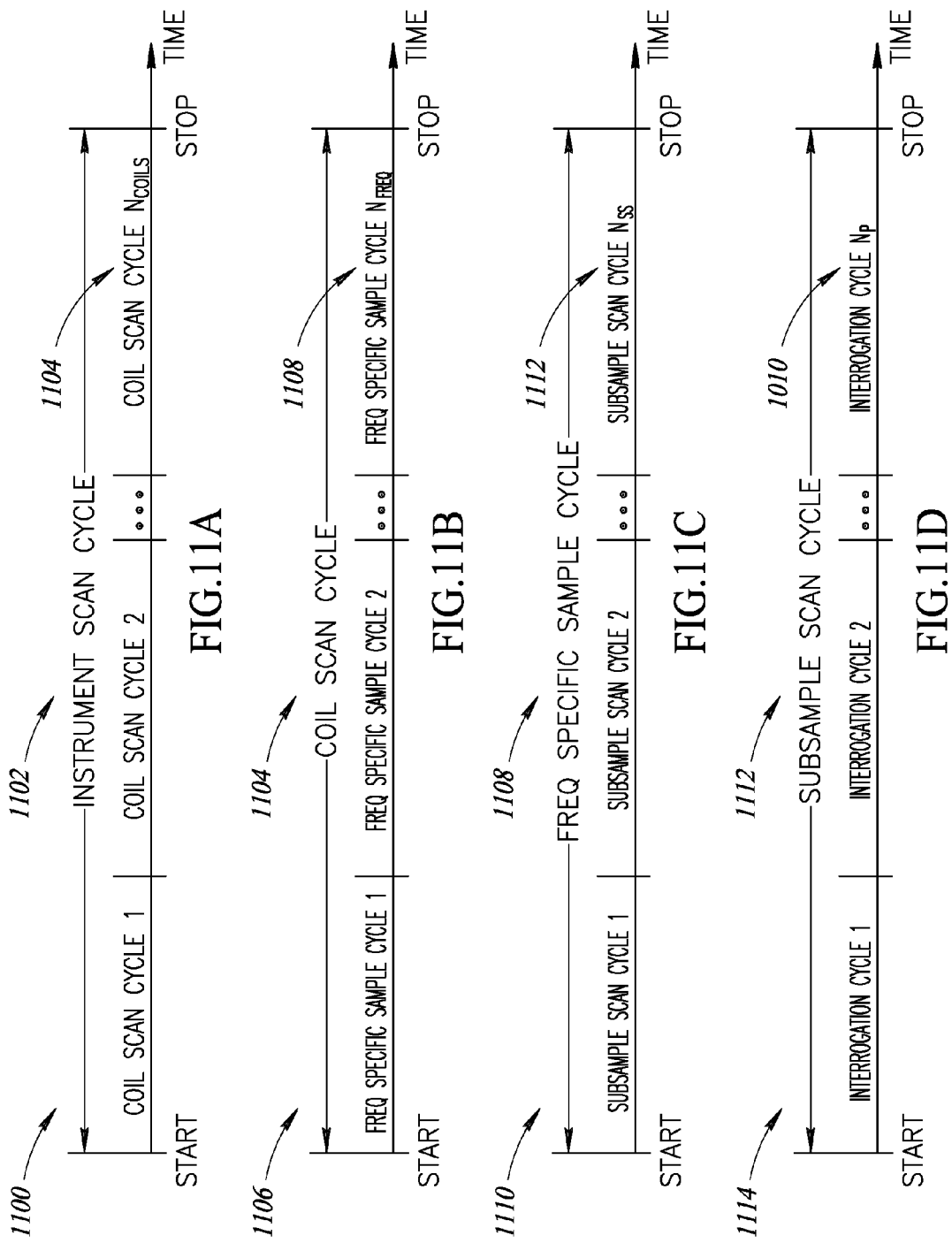

At 1310, the interrogation and detection system begins a first interrogation cycle (interrogation cycle 1) for a first subsample scan cycle (subsample scan cycle 1) by emitting an electromagnetic interrogation signal centered at first frequency (frequency specific sample cycle 1) during a transmit portion 1010a of the interrogation cycle (see FIGS. 10 and 11). At 1312, the interrogation and detection system receives unmodulated electromagnetic signals during a receive response portion 1010d of the interrogation cycle that follows the transmit portion 1010a of the interrogation cycle. As discussed above with reference to FIG. 10, the interrogation cycle may include a dump portion 1010*b*, recovery portion 1010*c*, and/or a skip portion 1010*e* between the transmit portion 1010*a* and the receive response portion 1010*d*. The timing of the receive response portion 1010*d* may be such that the expected transponder response signal is synchronous or coherent with the transmit portion 1010*a* to improve the likelihood that peaks of the transponder response signal are detected. During the receive response portion 1010*d* of the interrogation cycle, the FPGA 508 controls the signal ADC 128 to sample the response signal from the transponder. The signal ADC 128 may, for example, obtain 512 measurements in 512 µs by sampling at a 1 MHz sample rate (i.e., 1 sample per µs). In some implementations the signal ADC 128 may sample at different rates and may obtain more or less measurements during each receive response portion 1010*d*.

At 1314, the interrogation and detection system waits a subsample scan cycle delay period 1010*f*, which in some implementations is a fraction of the period T of the expected transponder response signal, before starting the next interrogation cycle at 1310. The subsample scan cycle delay period may be approximately equal to ((SUBSAMPLE_COUNT−1)/$N_{SS}$) times the period (T) of the expected transponder response signal, in some implementations. Thus, for interrogation cycles associated with subsample scan cycle 1, the subsample scan cycle delay period is approximately zero seconds (i.e., (0/$N_{SS}$)*T=0). For interrogation cycles associated with subsample scan cycle 2, the subsample scan cycle delay period is approximately equal to (1/$N_{SS}$)*T, and so on as discussed above.

At 1316, the interrogation and detection system increments the control variable INTERROGATION_COUNT. At 1318, the interrogation and detection system compares the value of INTERROGATION_COUNT to the number of interrogation cycles $N_I$ per subsample scan cycle. The interrogation and detection system thus continues to loop through acts 1310-1314 (i.e., interrogation cycles) until all of the interrogation cycles in subsample scan cycle 1 have been executed. The number of interrogation cycles per subsample scan cycle may be any suitable value, such as 1, 100, 250, 500, 2000, etc.

Once all of the interrogation cycles for subsample scan cycle 1 have been executed (i.e., decision 1318=YES), the interrogation and detection system increments the control variable SUBSAMPLE_COUNT at 1320, and compares its value to the number of subsample scan cycles $N_{SS}$ at 1322. Thus, similar to the acts for subsample scan cycle 1, the interrogation and detection system executes the acts 1310-1314 for subsample scan cycle 2 to subsample scan cycle $N_{SS}$ to complete a total of $N_{SS}$ subsample scan cycles and collect $N_{SS}$ subsamples.

Once all of the interrogation cycles for each of the subsample scan cycles 1 to $N_{SS}$ have been executed (i.e., decision 1322=YES), the interrogation and detection system increments the control variable FREQUENCY_COUNT at 1324 and compares its value to the number of transmit frequencies ($N_{FREQ}$) at 1326. If the number of transmit frequencies $N_{FREQ}$ is greater than one, the interrogation and detection system repeats the acts discussed above to perform $N_{SS}$ subsample scan cycles at each of the number $N_{FREQ}$ of transmit frequencies for a total of $N_{FREQ}$ frequency specific sample cycles.

The method 1300 may terminate at 1328 until started again. As discussed above, the method 1300 may repeat for one or more additional antenna coils of the interrogation and detection system. The method 1300 may continually repeat when the interrogation and detection system is in the Scan Mode. Alternatively or additionally, the method 1300 may run concurrently with other methods or processes.

FIG. 14 shows a method 1400 of operating an interrogation and detection system to execute an instrument scan cycle 1102 (FIG. 11), according to one illustrated implementation. The method 1400 may be implemented by any of the interrogation and detection system implementations discussed above. The method 1400 may be used to collect subsamples by performing subsample scan cycles using the interrogation cycles illustrated in FIGS. 10 and 12.

The method starts at 1402. The method 1400 may, for example, start when an interrogation and detection system enters the Scan Mode 714 (FIG. 7). At 1404, the interrogation and detection system initializes a control variable COIL_COUNT. This control variable may be used during the method 1400 for comparison with a number of coils ($N_{COILS}$) included in the interrogation and detection system. For example, in some implementations the interrogation and detection system may include a plurality of coils or antennas that may be used to scan for transponders. In some implementations, the interrogation and detection system may include a plurality of coils spaced apart from each other that are each designed to detect transponders in different physical locations. For example, in some implementations six coils may be spaced apart in or on a mat positioned under a patient on a patient support structure. The six coils may be used to detect transponders at different locations proximate to the patient's body. In some implementations, multiple coils may be provided to transmit or receive signals in multiple directions (e.g., x-, y-, and z-directions).

At 1406, the interrogation and detection system performs a coil scan cycle 1104 (FIG. 11A) to detect transponders using a first coil. The interrogation and detection system may execute this act using the method 1300 of FIG. 13 discussed above to perform a coil scan cycle 1104, which may include $N_{FREQ}$ frequency specific sample cycles, each of which may include $N_{SS}$ subsample scan cycles, each of which may include $N_I$ interrogation cycles. At 1408, the interrogation and detection system increments the control variable COIL_COUNT and compares its value to the number of coils at 1410. If the interrogation and detection subsystem includes additional coils, the system sequentially performs coil scan cycles 1104 in round robin fashion for each of the coils to scan for transponders.

The method 1400 may terminate at 1412 until started again. The method 1400 may continually repeat when the interrogation and detection system is in the Scan Mode. Alternatively or additionally, the method 1400 may run concurrently with other methods or processes.

FIG. 15 shows a method 1500 of operating an interrogation and detection system to execute one or more instrument scan cycles 1102 (FIG. 11), according to one illustrated implementation. The method 1500 may be implemented by any of the interrogation and detection system implementations discussed above. The method 1500 may be used to collect subsamples by performing subsample scan cycles using the interrogation cycles illustrated in FIGS. 10 and 12.

The method 1500 begins at 1502. At 1504 the interrogation and detection system may receive a scan mode selection from a user (e.g., via the controller 110). In some implementations, a graphical user interface of the controller 110 may present a prompt to the user requesting a selection of a scan mode. In some implementations, the system may automatically select a scan mode for the user. In this implementation, the interrogation and detection system is configured to provide at least two different types of instrument scan cycles: a static scan and a dynamic scan. During a static scan, the user maintains the probe 112 in a substantially fixed position relative to the patient 108. For example, in a child delivery medical setting, the user may position the probe 112 near the top of the patient's pelvic bone when the patient is in the lithotomy position to scan for detection of objects (e.g., retained sponges). During a dynamic scan, the user may move the probe 112 to various locations to scan for detection of objects. For example, in the dynamic instrument scan cycle mode, the user may move the probe 112 near a trash can, near portions of the patient's body, near a drape bag, and/or near other areas in a medical facility to scan for objects (e.g., so that such objects may be counted).

If the user has selected a static scan (i.e., decision 1506=YES), the interrogation and detection system executes one or more static instrument scan cycles at 1508. If the user has selected a dynamic scan (i.e., decision 1510=YES), the interrogation and detection system executes one or more dynamic instrument scan cycles at 1512.

The static instrument scan cycle and the dynamic instrument scan cycle differ by the number of subsamples obtained. The time available for the dynamic instrument scan cycle is less than the time available for the static instrument cycle because, in the dynamic scan cycle mode, the user is constantly moving the probe 112 relative to a transponder that is to be detected. Thus, to provide a relatively fast scan, in some implementations only a single frequency specific sample cycle 1108 (FIGS. 11B and 11C) with four subsample scan cycles 1112 (FIGS. 11C and 11D) are executed in the dynamic instrument scan cycle mode. This is in contrast to the static instrument scan cycle, which in some implementations utilizes two or more frequency specific sample cycles 1108 and seven or more subsample scan cycles 1112 per frequency specific sample cycle.

In operation, the medical provider 102 may operate the interrogation and detection system in both instrument scan cycle modes after a medical procedure. For example, the user may operate the interrogation and detection system in the static scan cycle mode to first detect whether any objects are retained in the patient, and then operate the system in the dynamic scan cycle mode to detect whether any objects are located in surrounding areas (e.g., trash cans, drape bags, etc.).

As discussed above, in some implementations the dynamic scan mode includes a single frequency specific sample cycle 1108 (FIGS. 11B and 11C) that includes four subsample scan cycles 1112. Thus, the instrument scan cycle 1102 in the dynamic mode includes sequentially performing a coil scan cycle 1104 (FIG. 11A) for each of the three orthogonal coils 338a, 338b, and 338c, where each coil scan cycle includes one frequency specific sample cycle 1108 that includes four subsample scan cycles 1112.

In some implementations, the static scan mode includes two frequency specific sample cycles 1108 that each include seven subsample scan cycles 1112. Thus, the instrument scan cycle 1102 in the static mode includes sequentially performing a coil scan cycle 1104 for each of the three orthogonal coils 338a, 338b, 338c of the two coil sets, where each coil scan cycle includes two frequency specific sample cycles 1108 that each include seven subsample scan cycles 1112.

In some implementations, a single subsample scan cycle 1112 may have a duration of approximately 216 milliseconds. Continuing with the example discussed above, a single dynamic instrument scan cycle may have a duration of about 2.6 seconds (i.e., 216 milliseconds per subsample scan cycle, 4 subsample scan cycles per frequency specific sample scan, 1 frequency specific sample scan per coil, and 3 orthogonal coils). A single static instrument scan cycle may have a duration of approximately 9.1 seconds (i.e., 216 milliseconds per subsample scan cycle, 7 subsample scan cycles per frequency specific sample scan, 2 frequency specific sample scans per coil, and 3 orthogonal coils). The durations of the static and dynamic instrument scan cycles may be modified to suit a particular application, recognizing the tradeoff between scan time and the number of samples collected.

The method 1500 terminates at 1514 until started again. The method 1500 may start again, for example, when the user makes a selection of one of the dynamic scan cycle mode or the static scan cycle mode.

FIG. 16 shows a method 1600 of operating an interrogation and detection system, according to one illustrated implementation.

At 1602, the interrogation and detection system determines the presence or absence of a transponder based at least in part on at least one of the subsamples obtained by performing the method 1300 and/or the method 1400 discussed above (FIGS. 13 and 14).

As discussed above, the signal ADC 128 (FIG. 5) converts the signal received from the transponder, if any, from analog to digital. Such conversion may, for example, be performed at a sampling rate of 1 MHz with a 12-bit data resolution. In the example shown in FIG. 12, subsample scan cycles 1-7 each include 250 interrogation cycles, and the signal ADC 128 obtains 512 measurements per interrogation cycle. The sampled ADC data for each subsample scan cycle may be accumulated together or integrated to compute the total summed response signal received from the transponder 116, if any, for each subsample.

In some implementations, the accumulated or integrated received signal for each subsample is matched filtered with both in-phase and quadrature reference signals to determine the signal magnitude. The received response signal may be matched filtered with a plurality of reference signals, for example with the seven reference signals, for instance as shown in Table 1 above. Some implementations may employ matched filtering before accumulating or integrating the received signal.

For each subsample collected, the maximum value for the matched filters (e.g., seven matched filters) with active transmit may be compared with an adjusted detection threshold. If the maximum value is greater than the detection threshold for one or more subsamples, then a response signal from a transponder is considered as having been detected, and appropriate action is taken, such as discussed above with reference to FIG. 7. In some implementations, a value greater than the detection threshold for two or more subsamples is required before a transponder is considered to have been detected.

The above description of illustrated implementations, including what is described in the Abstract, is not intended to be exhaustive or to limit the implementations to the precise forms disclosed. Although specific implementations of and examples are described herein for illustrative purposes, various equivalent modifications can be made without departing from the spirit and scope of the disclosure, as will be recognized by those skilled in the relevant art. The teachings provided herein of the various implementations can be applied to other transponders and interrogation and detection systems, not necessarily the exemplary surgical object transponders and interrogation and detection systems generally described above.

For instance, the foregoing detailed description has set forth various implementations of the devices and/or processes via the use of block diagrams, schematics, and examples. Insofar as such block diagrams, schematics, and examples contain one or more functions and/or operations, it will be understood by those skilled in the art that each function and/or operation within such block diagrams, flowcharts, or examples can be implemented, individually and/or collectively, by a wide range of hardware, software, firmware, or virtually any combination thereof. In one implementation, the present subject matter may be implemented via Application Specific Integrated Circuits (ASICs). However, those skilled in the art will recognize that the implementations disclosed herein, in whole or in part, can be equivalently implemented in standard integrated circuits, as one or more computer programs running on one or more computers (e.g., as one or more programs running on one or more computer systems), as one or more programs running on one or more controllers (e.g., microcontrollers) as one or more programs running on one or more processors (e.g., microprocessors), as firmware, or as virtually any combination thereof, and that designing the circuitry and/or writing the code for the software and or firmware would be well within the skill of one of ordinary skill in the art in light of this disclosure.

In addition, those skilled in the art will appreciate that the mechanisms of taught herein are capable of being distributed as a program product in a variety of forms, and that an illustrative implementation applies equally regardless of the particular type of signal bearing media used to actually carry out the distribution. Examples of signal bearing media include, but are not limited to, the following: recordable type media such as floppy disks, hard disk drives, CD ROMs, digital tape, and computer memory; and transmission type media such as digital and analog communication links using TDM or IP based communication links (e.g., packet links).

The various implementations described above can be combined to provide further implementations. U.S. Provisional Patent Application Ser. No. 61/056,787, filed May 28, 2008; U.S. Provisional Patent Application Ser. No. 61/091,667, filed Aug. 25, 2008; U.S. Provisional Patent Application No. 60/811,376 filed Jun. 6, 2006; U.S. Pat. No. 6,026,818, issued Feb. 22, 2000; U.S. Patent Publication No. US 2004/0250819, published Dec. 16, 2004; U.S. provisional patent application Ser. No. 60/811,376, filed Jun. 6, 2006; U.S. non-provisional patent application Ser. No. 11/743,104, filed May 1, 2007; U.S. provisional patent application Ser. No. 61/972,826, filed Mar. 31, 2014; U.S. provisional patent application Ser. No. 61/972,832, filed Mar. 31, 2014; U.S. non-provisional patent application Ser. No. 14/327,208, filed Jul. 9, 2014; and U.S. non-provisional patent application Ser. No. 14/327,208, filed Jul. 9, 2014, and international PCT patent application Serial No. US2014/070547, filed Dec. 16, 2014, are incorporated herein by reference, in their entirety. Aspects of the implementations can be modified, if necessary, to employ systems, circuits and concepts of the various patents, applications and publications to provide yet further implementations.

These and other changes can be made to the implementations in light of the above-detailed description. In general, in the following claims, the terms used should not be construed to limit the claims to the specific implementations disclosed in the specification and the claims, but should be construed to include all possible implementations along with the full scope of equivalents to which such claims are entitled. Accordingly, the claims are not limited by the disclosure.

The invention claimed is:

1. A transponder detection device to detect surgical objects in a work area, the surgical objects marked by respective resonant tag elements that produce return signals in response to energization, the transponder detection device comprising:
   a hand-held probe comprising:
      a housing having a cavity therein; and
      a first coil assembly and a second coil assembly received within the cavity of the housing spaced from each other, wherein each of the first and the second coil assemblies respectively includes:
         a substantially spherically shaped coil form that includes three coil support channels, each of the three coil support channels which define an outer coil support surface;
         a first antenna element comprising a first electrical conductor wound around the outer coil support surface of a first one of the three coil support channels, the first antenna element arranged to transmit and receive signals generally in a first coordinate direction;
         a second antenna element comprising a second electrical conductor wound around the outer coil support surface of a second one of the three coil support channels over the first electrical conductor, the second antenna element arranged to transmit and receive signals generally in a second coordinate direction orthogonal to the first coordinate direction; and
         a third antenna element comprising a third electrical conductor wound around the outer coil support surface of a third one of the three coil support channels over the first electrical conductor and the second electrical conductor, the third antenna element arranged to transmit and receive signals generally in a third coordinate direction orthogonal to the first coordinate direction and the second coordinate direction;
   a processor operatively coupled to the respective first antenna elements, the second antenna elements, and the third antenna elements of the first and the second coil assemblies; and
   a nontransitory processor-readable medium communicatively coupled to the processor and that stores at least one of instructions or data executable by the processor, which cause the processor to:
      control each of the first antenna elements, the second antenna elements and the third antenna elements of the first and the second coil assemblies to emit wideband interrogation signals;
      receive any of the return signals from any of the resonant tag elements; and
      determine from a receipt of any of the return signals whether any of the resonant tag elements are present in the work area.

2. The transponder detection device of claim 1 wherein the cavity of the housing is defined by a first body portion that receives the first coil assembly, a second body portion that receives the second coil assembly, and a handle portion disposed between the first body portion and the second body portion.

3. The transponder detection device of claim 2 wherein the handle portion is disposed between the first body portion and the second body portion to allow the first body portion and the second body portion to at least partially surround a human joint during use.

4. The transponder detection device of claim 1 wherein at least one of the first, the second or the third antenna elements of the first coil assembly is arranged to transmit and receive signals generally in a coordinate direction which is the same as a coordinate direction in which at least one of the first, the second or the third antenna elements of the second coil assembly is arranged to transmit and receive signals.

5. The transponder detection device of claim 1 wherein each of the first, the second and the third antenna elements of the first coil assembly is arranged to transmit and receive signals generally in a coordinate direction which is the same as a coordinate direction in which a different one of the first, the second or the third antenna elements of the second coil assembly is arranged to transmit and receive signals.

6. The transponder detection device of claim 1 wherein at least one of the first, the second or the third antenna elements of the first coil assembly is coplanar with at least one of the first, the second or the third antenna elements of the second coil assembly.

7. The transponder detection device of claim 1 wherein, for each of the respective coil forms of the first and the second coil assemblies, each of the three coil support channels is shaped as a spherical zone of a virtual sphere.

8. The transponder detection device of claim 7 wherein, for each of the respective coil forms of the first and the second coil assemblies, each of the three coil support channels is shaped as a spherical zone of a virtual sphere centered on a great circle of the virtual sphere.

9. The transponder detection device of claim 1 wherein, for each of the respective coil forms of the first and the second coil assemblies, the three coil support channels are shaped as a spherical zone of the substantially spherically shaped coil form centered on respective orthogonal great circles of the coil form.

10. The transponder detection device of claim 1, further comprising:
a light source coupled to the housing that provides a visual indication of at least a status of the transponder detection device.

11. The transponder detection device of claim 1 wherein the processor:
controls each of the respective first antenna elements, the second antenna elements and the third antenna elements of the first and the second coil assemblies to emit wideband interrogation signals in time-wise succession during a transmit portion of respective transmit and receive cycles, and controls each of the first antenna elements, the second antenna elements and the third antenna elements of the first and the second coil assemblies to not emit wideband interrogation signals during a receive portion of respective transmit and receive cycles.

12. The transponder detection device claim 1 wherein the processor further:
receives a selection of at least one of a dynamic scan mode and a static scan mode;
in response to receiving a selection of the static scan mode, controls each of the first antenna elements, the second antenna elements and the third antenna elements to emit wideband interrogation signals according to a static instrument scan cycle having a static instrument scan cycle duration; and
in response to receiving a selection of the dynamic scan mode, controls each of the first antenna elements, the second antenna elements and the third antenna elements to emit wideband interrogation signals according to a dynamic instrument scan cycle having a dynamic instrument scan cycle duration that is less than the static instrument scan cycle duration.

13. The transponder detection device of claim 12 wherein, in response to receiving a selection of the static scan mode, the processor controls each of the first antenna elements, the second antenna elements and the third antenna elements to emit wideband interrogation signals centered on a first frequency, and further controls each of the first antenna elements, the second antenna elements and the third antenna elements to emit wideband interrogation signals centered on a second frequency, the second frequency different from the first frequency.

14. The transponder detection device claim 1 wherein the processor further:
determines from a receipt of any of the return signals whether any of the resonant tag elements are present in the work area based at least in part on a frequency of the return signals received being within a defined frequency range.

15. The transponder detection device of claim 1 wherein the processor further:
determines whether any of the resonant tag elements are present in the work area based at least in part on a Q value of the return signals received.

16. The transponder detection device of claim 1 wherein the processor further:
receives electromagnetic signals during a noise detection portion;
determines a noise value indicative of a noise level that corresponds to a number of measurements of the electromagnetic signals received during the noise detection portion;
adjusts a signal detection threshold based at least in part on the determined noise value; and
determines whether any of the resonant tag elements are present in the work area based at least in part on a number of measurements of the return signals received and the adjusted signal detection threshold.

17. A method to detect surgical objects in a work area, the surgical objects marked by respective resonant tag elements that produce return signals in response to energization, the method comprising:
providing a transponder detection device that includes a hand-held probe comprising a housing having a cavity therein; a first coil assembly and a second coil assembly received within the cavity of the housing spaced from each other, wherein each of the first and the second coil assemblies respectively includes: a substantially spherically shaped coil form that includes three coil support channels, each of the three coil support channels which define an outer coil support surface; a first antenna element comprising a first electrical conductor wound around the outer coil support surface of a first one of the three coil support channels, the first antenna element arranged to transmit and receive signals generally in a first coordinate direction;
a second antenna element comprising a second electrical conductor wound around the outer coil support surface of a second one of the three coil support channels over the first electrical conductor, the second antenna element arranged to transmit and receive signals generally in a second coordinate direction orthogonal to the first coordinate direction; and a third antenna element comprising a third electrical conductor wound around the outer coil support surface of a third one of the three coil support channels over the first electrical conductor and the second electrical conductor, the third antenna element arranged to transmit and receive signals generally in a third coordinate direction orthogonal to the first coordinate direction and the second coordinate direction;

emitting wideband interrogation signals via the respective first antenna elements, the second antenna elements and the third antenna elements of the first and the second coil assemblies;

receiving any of the return signals from any of the resonant tag elements via at least one of the respective first antenna elements, the second antenna elements and the third antenna elements of the first and the second coil assemblies; and determining from a receipt of any of the return signals whether any of the resonant tag elements are present in the work area, wherein emitting wideband interrogation signals and receiving any of the return signals comprises controlling each of the first antenna elements, the second antenna elements and the third antenna elements to emit wideband interrogation signals in time-wise succession during a transmit portion of respective transmit and receive cycles and controlling each of the first antenna elements, the second antenna elements and the third antenna elements to not emit wideband interrogation signals during a receive portion of respective transmit and receive cycles.

18. A method to detect surgical objects in a work area, the surgical objects marked by respective resonant tag elements that produce return signals in response to energization, the method comprising:

providing a transponder detection device that includes a hand-held probe comprising a housing having a cavity therein; a first coil assembly and a second coil assembly received within the cavity of the housing spaced from each other, wherein each of the first and the second coil assemblies respectively includes: a substantially spherically shaped coil form that includes three coil support channels, each of the three coil support channels which define an outer coil support surface; a first antenna element comprising a first electrical conductor wound around the outer coil support surface of a first one of the three coil support channels, the first antenna element arranged to transmit and receive signals generally in a first coordinate direction; a second antenna element comprising a second electrical conductor wound around the outer coil support surface of a second one of the three coil support channels over the first electrical conductor, the second antenna element arranged to transmit and receive signals generally in a second coordinate direction orthogonal to the first coordinate direction; and a third antenna element comprising a third electrical conductor wound around the outer coil support surface of a third one of the three coil support channels over the first electrical conductor and the second electrical conductor, the third antenna element arranged to transmit and receive signals generally in a third coordinate direction orthogonal to the first coordinate direction and the second coordinate direction;

controlling each of the first antenna elements, the second antenna elements and the third antenna elements to emit wideband interrogation signals according to a static instrument scan cycle having a static instrument scan cycle duration;

controlling each of the first antenna elements, the second antenna elements and the third antenna elements to emit wideband interrogation signals according to a dynamic instrument scan cycle having a dynamic instrument scan cycle duration that is less than the static instrument scan cycle duration;

receiving any of the return signals from any of the resonant tag elements via at least one of the respective first antenna elements, the second antenna elements and the third antenna elements of the first and the second coil assemblies; and determining from a receipt of any of the return signals whether any of the resonant tag elements are present in the work area.

\* \* \* \* \*